(12) United States Patent
Klosin et al.

(10) Patent No.: US 9,862,734 B2
(45) Date of Patent: Jan. 9, 2018

(54) METAL-LIGAND COMPLEX, OLEFIN POLYMERIZATION CATALYST DERIVED THEREFROM, AND OLEFIN POLYMERIZATION METHOD UTILIZING THE CATALYST

(71) Applicant: DOW Global Technologies LLC, Midland, MI (US)

(72) Inventors: Jerzy Klosin, Midland, MI (US); Philip P. Fontaine, Houston, TX (US); Ruth Figueroa, Midland, MI (US); David M. Pearson, Lake Jackson, TX (US); Todd D. Senecal, Midland, MI (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 0 days.

(21) Appl. No.: 15/032,150

(22) PCT Filed: Nov. 11, 2014

(86) PCT No.: PCT/US2014/064931
§ 371 (c)(1),
(2) Date: Apr. 26, 2016

(87) PCT Pub. No.: WO2015/094513
PCT Pub. Date: Jun. 25, 2015

(65) Prior Publication Data
US 2016/0311837 A1   Oct. 27, 2016

Related U.S. Application Data

(60) Provisional application No. 61/918,309, filed on Dec. 19, 2013.

(51) Int. Cl.
| | | |
|---|---|---|
| C08F 4/76 | (2006.01) | |
| C08F 4/64 | (2006.01) | |
| C07F 7/00 | (2006.01) | |
| B01J 31/00 | (2006.01) | |
| C07F 7/28 | (2006.01) | |
| C08F 110/14 | (2006.01) | |

(52) U.S. Cl.
CPC ............ *C07F 7/00* (2013.01); *B01J 31/00* (2013.01); *C07F 7/006* (2013.01); *C07F 7/28* (2013.01); *C08F 110/14* (2013.01)

(58) Field of Classification Search
CPC .... C07F 7/00; C07F 7/28; C07F 11/00; C08F 4/64044
See application file for complete search history.

(56) References Cited

U.S. PATENT DOCUMENTS

| | | | |
|---|---|---|---|
| 5,064,802 A | 11/1991 | Stevens et al. | |
| 5,153,157 A | 10/1992 | Hlatky et al. | |
| 5,296,433 A | 3/1994 | Siedle et al. | |
| 5,321,106 A | 6/1994 | LaPointe | |
| 5,350,723 A | 9/1994 | Neithamer et al. | |
| 5,425,872 A | 6/1995 | Devore et al. | |
| 5,625,087 A | 4/1997 | Devore et al. | |
| 5,721,185 A | 2/1998 | LaPointe et al. | |
| 5,783,512 A | 7/1998 | Jacobsen et al. | |
| 5,866,704 A | 2/1999 | Nickias et al. | |
| 5,883,204 A | 3/1999 | Spencer et al. | |
| 5,919,983 A | 7/1999 | Rosen et al. | |
| 5,959,047 A | 9/1999 | Nickias et al. | |
| 6,103,657 A | 8/2000 | Murray | |
| 6,147,172 A | † 11/2000 | Brown | |
| 6,268,444 B1 | 7/2001 | Klosin et al. | |
| 6,515,155 B1 | 2/2003 | Klosin et al. | |
| 6,696,379 B1 | 2/2004 | Carnahan et al. | |
| 7,163,907 B1 | 1/2007 | Canich et al. | |
| 7,547,751 B2 | 6/2009 | Ijepij et al. | |
| 8,202,954 B2 | 6/2012 | Klosin et al. | |
| 2004/0192541 A1 | 9/2004 | Kretschmer | |
| 2012/0095158 A1 | 4/2012 | Patel et al. | |

FOREIGN PATENT DOCUMENTS

| | | |
|---|---|---|
| WO | 9323412 A1 | 11/1993 |
| WO | 9400050 A1 | 1/1994 |

(Continued)

OTHER PUBLICATIONS

Tamm, M.; Randoll, S.; Herdtweck, E.; Kleigrewe, N.; Kehr, G.; Erker, G.; Rieger, B. Dalton Trans. 2006, 459-467.*
Akzonobel "MMAO-3A/Heptane Solutions" Product Data Sheet, OMS 667231.11/Aug. 2010 (2 pages).
Haas, et al., "A Highly Efficient Titanium Catalyst for the Synthesis of Ultrahigh-Molecular-Weight Polyethylene UHMWPE)", Chemistry—A European Journal, vol. 19, No. 28, Jul. 8, 2013, pp. 9132-9136.
International Search Report dated Mar. 12, 2015; International Application No. PCT/US2014/064931; International Filing Date Nov. 11, 2014 (7 pages).

(Continued)

*Primary Examiner* — Rip A Lee
(74) *Attorney, Agent, or Firm* — Cantor Colburn LLP

(57) ABSTRACT

A metal-ligand complex has formula (I): wherein J, L, M, $R^1$, $R^2$, $R^3$, $R^4$, X, p, q, and r are defined herein. The metal-ligand complex is useful as a catalyst or catalyst precursor for olefin polymerization.

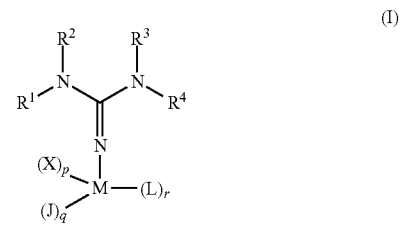

17 Claims, No Drawings

(56) References Cited

FOREIGN PATENT DOCUMENTS

| WO | 2005014665 A1 | 2/2005 |
|---|---|---|
| WO | 2014139861 A1 | 9/2014 |

OTHER PUBLICATIONS

Kretschmer, et al., "A Highly Efficient Titanium-based Olefin Polymerisation Catalyst With a Monoanionic Iminoimidazolidide n-donor Anicallary Ligand", Chem. Commun., 2002, pp. 608-209.

Randoll, et al., "Chromium Complexes with Me2Si-Bridged Cyclopentadienyl-imidazolin-2-imine Ligands: Synthesis, Structure, and Use in Ethylene Polymerization Catalysis", Organometallics 2008, vol. 27, pp. 3232-3239.

Sharma, et al., "Bis(1,3-di-tert-butylimidazolin-2-iminato) Titanium Complexes as Effective Catalysts for the Monodisperse Polymerization of Propylene" Journal of the American Chemical Society, vol. 134, No. 41, Oct. 17, 2012, pp. 17234-17244.

Shoken, et al., "Mono(imidazolin-2-iminato) Titanium Complexes for Ethylene Polymerization at Low Amounts of Methylaluminoxane", Journal of the American Chemical Society, 2013, vol. 135, No. 34, pp. 12592-12595.

Tamm, et al., "Efficient Direct Synthesis of Tropidinyl Titanium and Zirconium Complexes by Allylic CH-Activation of 8-Methyl-8-azabicyclo[3.2.1]oct-2-ene (Tropidine)" Organometallics 2007, vol. 26, pp. 761-764.

Tamm, et al., "Imidazolin-2-iminato titanium complexes: synthesis, structure and use in ethylene polymerization catalysis", Dalton Transactions, No. 3, Jan. 1, 2006, pp. 459-467.

Tamm, et al., "Titanium Complexes With Imidazolin-2-iminato Ligands", Chem. Commun., 2004, pp. 876-877.

Trambitas, et al., "Bis(imidazolin-2-iminato) Rare Earth Metal Complexes: Synthesis, Structural Characterization, and Catalytic Application" Inorg. Chem. 2012, vol. 51, pp. 6753-6761.

Written Opinion dated Mar. 12, 2015; International Application No. PCT/US2014/064931; International Filing Date Nov. 11, 2014 (8 pages).

Haas et al., "A Highly Efficient Titanium Catalyst for the Synthesis of Ultrahigh-Molecular-Weight Polyethylane (UHMWPE)", Wiley-VCH Verlag, pp. 9132-9136, May 28, 2013, online.†

\* cited by examiner
† cited by third party

METAL-LIGAND COMPLEX, OLEFIN POLYMERIZATION CATALYST DERIVED THEREFROM, AND OLEFIN POLYMERIZATION METHOD UTILIZING THE CATALYST

CROSS-REFERENCE TO RELATED APPLICATIONS

This application is a National Stage application of PCT/US2014/064931, filed 11/11/2014, which claims the benefit of U.S. Provisional Application No. 61/918,309, filed 12/19/2013, both of which are incorporated by reference herein in their entirety.

FIELD

The present invention generally relates to metal-ligand complexes, catalysts comprising or prepared from the metal-ligand complexes, and processes of catalyzing olefin polymerization reactions with the catalysts to prepare polyolefins.

INTRODUCTION

D. Shoken et al. "Mono(imidazolin-2-iminato) Titanium Complexes for Ethylene Polymerization at Low Amounts of Methylaluminoxane", *Journal of the American Chemical Society*, 2013, volume 135, number 34, pages 12592-12595, describes ethylene polymerization using catalyst precursors of the type Im=N—Ti(Cl)$_m$(CH$_3$)$_{3-m}$, where Im=N— is an imidazolin-2-iminato ligand, and m is 1, 2, or 3.

M. Sharma et al., "Bis(1,3-di-tert-butylimidazolin-2-iminato) Titanium Complexes as Effective Catalysts for the Monodisperse Polymerization of Propylene", *Journal of the American Chemical Society*, 2012, volume 134, number 41, pages 17234-17244, describes propylene polymerization using catalyst precursors of the type (Im=N—)$_2$Ti(CH$_3$)$_2$, where Im=N— is an imidazolin-2-iminato ligand.

Chemical industry desires new metal-ligand catalysts and catalyst precursors with improved stability under olefin polymerization reaction conditions. Preferably, the new catalysts would be useful for improving reaction yields, providing alternative substrate selectivities (e.g., providing a new relative selectivity for a monomer and co-monomer in making a polyolefin copolymer), exhibiting good thermal stability at high various reactor temperatures, producing polymers with high molecular weight, reducing manufacturing costs, improving process safety, or a combination thereof.

SUMMARY

One embodiment is a metal-ligand complex of formula (I):

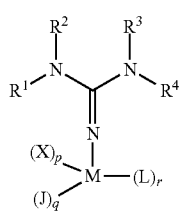

wherein J is a monoanionic moiety selected from $(R^K)(R^L)(R^X)P=N$—, $(R^K)(R^L)C=N$—, $(R^K)(R^L)(R^X)N)C=N$—, $(R^K)(R^L)B$—O—, $R^KO$—, $R^KS$—, $R^KS(O)$—, $(R^K)(R^L)N$—, $(R^KN=C(R^L)$—$N(R^X)$—, $(R^K)(R^L)NO$—, $R^KC(O)O$—, $R^KC(O)NH$—, and $(R^K)(R^L)P$—, wherein each $R^K$, $R^L$, and $R^X$ is independently is hydrogen, $(C_1-C_{40})$hydrocarbyl-, $((C_1-C_{15})$hydrocarbyl)$_3$Si—, $((C_1-C_{15})$hydrocarbyl)$_2$N—, or $(C_1-C_{40})$heterohydrocarbyl-; L is independently at each occurrence halogen, hydrogen, $((C_1-C_{40})$hydrocarbyl)C(O)N(H)—, $((C_1-C_{40})$hydrocarbyl)C(O)N(H)(C_1-C_{20})$hydrocarbyl-, $((C_1-C_{40})$hydrocarbyl)C(O)O—, $(C_1-C_{40})$hydrocarbyl-, $(C_1-C_{40})$heterohydrocarbyl-, $R^K(R^L)N$—, $R^LO$—, $R^LS$—, or $R^K(R^L)P$—, wherein each of $R^K$ and $R^L$ independently is as defined above; and each occurrence of L is a monoanionic moiety that is bonded to M; M is a metal of any one of Groups 3, 4, 5, and 6 of a Periodic Table of the Elements, the metal being in a formal oxidation state of +2, +3, +4, +5, or +6; $R^1$, $R^2$, $R^3$, and $R^4$ are independently at each occurrence hydrogen, $(C_1-C_{40})$hydrocarbyl-, $((C_1-C_{40})$hydrocarbyl)O—, $((C_1-C_{40})$hydrocarbyl)S—, $((C_1-C_{40})$hydrocarbyl)$_3$Si—, or $(C_1-C_{40})$heterohydrocarbyl-; X is a neutral Lewis base group selected from $R^XN(R^K)(R^L)$, $R^X=N(R^K)$, $R^KO(R^L)$, $R^KS(R^L)$, and $R^XP(R^K)(R^L)$, wherein each of $R^K$, $R^L$, and $R^X$ independently is as defined above; p is 0, 1, 2, or 3 (specifically 0 or 1), and q is 0 or 1, provided that the sum of p and q is at least 1; r is 2 or 3; two occurrences of L are optionally taken together to form a $(C_2-C_{40})$hydrocarbylene or $(C_1-C_{40})$heterohydrocarbylene, or $(R^D)_2C=C(R^D)$—$C(R^D)=C(R^D)_2$, wherein each $R^D$ independently is hydrogen, unsubstituted $(C_1-C_6)$alkyl, phenyl, or naphthyl; J and one of $R^1$, $R^2$, $R^3$, and $R^4$ are optionally taken together to form $(C_2-C_{40})$hydrocarbylene or $(C_1-C_{40})$heterohydrocarbylene; one occurrence of L and one of $R^1$, $R^2$, $R^3$, and $R^4$ are optionally taken together to form $(C_2-C_{40})$hydrocarbylene or $(C_1-C_{40})$heterohydrocarbylene; one occurrence of X and one of $R^1$, $R^2$, $R^3$, and $R^4$ are optionally taken together to form $(C_1-C_{40})$heterohydrocarbylene; any two of $R^1$, $R^2$, $R^3$, and $R^4$ are optionally taken together to form a $(C_2-C_{40})$hydrocarbylene or $(C_1-C_{40})$heterohydrocarbylene; X and J are optionally taken together to form a monoanionic bidentate moiety X-J, provided that when X-J is bound to M to form a fragment having the structure

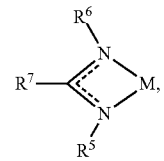

then $R^5$, $R^6$, and $R^7$ are each independently hydrogen, $(C_1-C_{40})$hydrocarbyl-, $((C_1-C_{40})$hydrocarbyl)O—, $((C_1-C_{40})$hydrocarbyl)S—, $((C_1-C_{40})$hydrocarbyl)$_3$Si—, or $(C_1-C_{40})$heterohydrocarbyl-; and provided that when X-J is bound to M via an anionic nitrogen and a Lewis base nitrogen, X-J and M form a four-membered metallocycle or a six-membered metallocycle; and each of the above-mentioned $(C_1-C_{40})$hydrocarbyl, $(C_1-C_{40})$heterohydrocarbyl, $(C_2-C_{40})$hydrocarbylene, and $(C_1-C_{40})$heterohydrocarbylene independently is the same or different and is unsubstituted or substituted with one or more substituents $R^S$ selected from halogen, unsubstituted $(C_1-C_{18})$hydrocarbyl, $F_3C$—, $FCH_2O$—, $F_2HCO$—, $F_3CO$—, oxo, $R_3Si$—, $RO$—, $RS$—, $RS(O)$—, $RS(O)_2$—, $R_2P$—, $R_2N$—, $R_2C=N$—, NC—, RC(O)O—, ROC(O)—, RC(O)N(R)—, and $R_2$NC(O)—, wherein each R independently is an unsubstituted $(C_1-C_{18})$hydrocarbyl.

Another embodiment is a catalyst comprising, or comprising the reaction product of, one or more metal-ligand complexes of the preceding paragraph, and one or more activating cocatalysts, wherein a ratio of total number of moles of the one or more metal-ligand complexes to total number of moles of the one or more activating cocatalyst is 1:10,000 to 100:1. Another embodiment is a process for preparing a polyolefin, the process comprising contacting at least one polymerizable olefin with the aforementioned catalyst under conditions sufficient to polymerize at least some of the at least one polymerizable olefin, thereby producing a polyolefin.

These and other embodiments are described in detail below.

DETAILED DESCRIPTION

As summarized previously, the present invention generally relates to metal-ligand complexes, catalysts comprising or prepared from the metal-ligand complexes, processes of catalyzing olefin polymerization reactions with the catalysts to prepare polyolefins. The present inventors have determined that the metal-ligand complexes described herein are precursors to active catalysts for olefin polymerization. Preferably, the catalyst comprises, or is prepared from, three or fewer, more preferably two, and still more preferably one metal-ligand complex of formula (I). Preferred catalysts show beneficial catalyst efficiencies (e.g., higher grams of polymer produced per gram of metal-ligand complex of formula (I)) and produce polyolefins, including polyolefin copolymers, having beneficially high weight average molecular weights ($M_w$), number average molecular weights ($M_n$), or both.

One embodiment is a metal-ligand complex of formula (I):

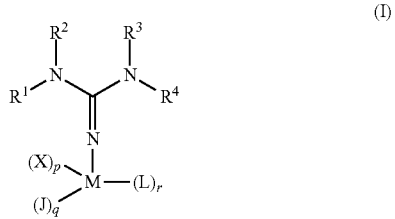

wherein J is a monoanionic moiety selected from $(R^K)(R^L)(R^X)P=N$—, $(R^K)(R^L)C=N$—, $(R^K)(R^L)(R^X)N)C=N$—, $(R^K)(R^L)B$—O—, $R^KO$—, $R^KS$—, $R^KS(O)$—, $(R^K)(R^L)N$—, $(R^KN=C(R^L))$—N($R^X$)—, $(R^K)(R^L)NO$—, $R^KC(O)O$—, $R^KC(O)NH$—, and $(R^K)(R^L)P$—, wherein each $R^K$, $R^L$, and $R^X$ is independently is hydrogen, $(C_1-C_{40})$hydrocarbyl-, $((C_1-C_{15})$hydrocarbyl$)_3$Si—, $((C_1-C_{15})$hydrocarbyl$)_2$N—, or $(C_1-C_{40})$heterohydrocarbyl-; L is independently at each occurrence halogen, hydrogen, $((C_1-C_{40})$hydrocarbyl$)C(O)N(H)$—, $((C_1-C_{40})$hydrocarbyl$)C(O)N(H)(C_1-C_{20})$hydrocarbyl-, $((C_1-C_{40})$hydrocarbyl$)C(O)O$—, $(C_1-C_{40})$hydrocarbyl-, $(C_1-C_{40})$heterohydrocarbyl-, $R^K(R^L)N$—, $R^LO$—, $R^LS$—, or $R^K(R^L)P$—, wherein each of $R^K$ and $R^L$ independently is as defined above; and each occurrence of L is a monoanionic moiety that is bonded to M; M is a metal of any one of Groups 3, 4, 5, and 6 of a Periodic Table of the Elements, the metal being in a formal oxidation state of +2, +3, +4, +5, or +6; $R^1$, $R^2$, $R^3$, and $R^4$ are independently at each occurrence hydrogen, $(C_1-C_{40})$hydrocarbyl-, $((C_1-C_{40})$hydrocarbyl$)O$—, $((C_1-C_{40})$hydrocarbyl$)S$—, $((C_1-C_{40})$hydrocarbyl$)_3$Si—, or $(C_1-C_{40})$heterohydrocarbyl-; X is a neutral Lewis base group selected from $R^XN(R^K)(R^L)$, $R^X=N(R^K)$, $R^KO(R^L)$, $R^KS(R^L)$, and $R^XP(R^K)(R^L)$, wherein each of $R^K$, $R^L$, and $R^X$ independently is as defined above; p is 0, 1, 2, or 3 (specifically 0 or 1), and q is 0 or 1, provided that the sum of p and q is at least 1; r is 2 or 3; two occurrences of L are optionally taken together to form a $(C_2-C_{40})$hydrocarbylene or $(C_1-C_{40})$heterohydrocarbylene, or $(R^D)_2C=C(R^D)$—$C(R^D)=C(R^D)_2$, wherein each $R^D$ independently is H, unsubstituted $(C_1-C_6)$alkyl, phenyl, or naphthyl; J and one of $R^1$, $R^2$, $R^3$, and $R^4$ are optionally taken together to form $(C_2-C_{40})$hydrocarbylene or $(C_1-C_{40})$heterohydrocarbylene; one occurrence of L and one of $R^1$, $R^2$, $R^3$, and $R^4$ are optionally taken together to form $(C_2-C_{40})$hydrocarbylene or $(C_1-C_{40})$heterohydrocarbylene; one occurrence of X and one of $R^1$, $R^2$, $R^3$, and $R^4$ are optionally taken together to form $(C_1-C_{40})$heterohydrocarbylene; any two of $R^1$, $R^2$, $R^3$, and $R^4$ are optionally taken together to form a $(C_2-C_{40})$hydrocarbylene or $(C_1-C_{40})$heterohydrocarbylene; X and J are optionally taken together to form a monoanionic bidentate moiety X-J, provided that when X-J is bound to M to form a fragment having the structure

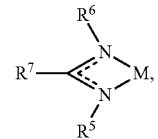

then $R^5$, $R^6$, and $R^7$ are each independently hydrogen, $(C_1-C_{40})$hydrocarbyl-, $((C_1-C_{40})$hydrocarbyl$)O$—, $((C_1-C_{40})$hydrocarbyl$)S$—, $((C_1-C_{40})$hydrocarbyl$)_3$Si—, or $(C_1-C_{40})$heterohydrocarbyl-; and provided that when X-J is bound to M via an anionic nitrogen and a Lewis base nitrogen, X-J and M form a four-membered metallocycle or a six-membered metallocycle; and each of the above-mentioned $(C_1-C_{40})$hydrocarbyl, $(C_1-C_{40})$heterohydrocarbyl, $(C_2-C_{40})$hydrocarbylene, and $(C_1-C_{40})$heterohydrocarbylene independently is the same or different and is unsubstituted or substituted with one or more substituents $R^S$ selected from halogen, unsubstituted $(C_1-C_{18})$hydrocarbyl, $F_3C$—, $FCH_2O$—, $F_2HCO$—, $F_3CO$—, oxo, $R_3Si$—, RO—, RS—, RS(O)—, $RS(O)_2$—, $R_2P$—, $R_2N$—, $R_2C=N$—, NC—, RC(O)O—, ROC(O)—, RC(O)N(R)—, and $R_2NC(O)$—, wherein each R independently is an unsubstituted $(C_1-C_{18})$hydrocarbyl.

As used herein, the term "$(C_1-C_{40})$hydrocarbyl" means a hydrocarbon radical of 1 to 40 carbon atoms and the term "$(C_1-C_{40})$hydrocarbylene" means a hydrocarbon diradical of from 1 to 40 carbon atoms, wherein each hydrocarbon radical and diradical independently is aromatic or non-aromatic, saturated or unsaturated, straight chain or branched chain, cyclic (including mono- and poly-cyclic, fused and non-fused polycyclic) or acyclic, or a combination of two or more of the foregoing; and each hydrocarbon radical and diradical is the same as or different from another hydrocarbon radical and diradical, respectively, and independently is unsubstituted or substituted by one or more $R^S$.

Preferably, a $(C_1-C_{40})$hydrocarbyl independently is an unsubstituted or substituted $(C_1-C_{40})$alkyl, $(C_3-C_{40})$cycloalkyl, $(C_3-C_{20})$cycloalkyl-$(C_1-C_{20})$alkylene, $(C_6-C_{40})$aryl, or $(C_6-C_{20})$aryl-$(C_1-C_{20})$alkylene. More preferably, a ($C_1$-$C_{40}$)hydrocarbyl independently is an unsubstituted or substituted ($C_1$-$C_{20}$)hydrocarbyl, e.g., ($C_1$-$C_{20}$)alkyl, ($C_3$-$C_{20}$)cycloalkyl, ($C_3$-$C_{10}$)cycloalkyl-($C_1$-$C_{10}$)alkylene, ($C_6$-$C_{20}$)aryl, or ($C_6$-$C_{18}$)aryl-($C_1$-$C_{10}$)alkylene. Still more preferably, a ($C_1$-$C_{40}$)hydrocarbyl independently is an unsubstituted or substituted ($C_1$-$C_{18}$)hydrocarbyl, e.g., ($C_1$-$C_{18}$)alkyl, ($C_3$-$C_{18}$)cycloalkyl, ($C_3$-$C_{12}$)cycloalkyl-($C_1$-$C_6$)alkylene, ($C_6$-$C_{18}$)aryl, or ($C_6$-$C_{12}$)aryl-($C_1$-$C_6$)alkylene. Preferably, any ($C_3$-$C_{18}$)cycloalkyl independently is an unsubstituted or substituted ($C_3$-$C_{10}$)cycloalkyl.

The term "($C_1$-$C_{40}$)alkyl" means a saturated straight or branched hydrocarbon radical of from 1 to 40 carbon atoms that is unsubstituted or substituted by one or more $R^S$. Examples of unsubstituted ($C_1$-$C_{40}$)alkyl are unsubstituted ($C_1$-$C_{20}$)alkyl; unsubstituted ($C_1$-$C_{10}$)alkyl; unsubstituted ($C_1$-$C_5$)alkyl; methyl; ethyl; 1-propyl; 2-propyl; 1-butyl; 2-butyl; 2-methylpropyl; 1,1-dimethylethyl; 1-pentyl; 1-hexyl; 1-heptyl; 1-nonyl; and 1-decyl. Examples of substituted ($C_1$-$C_{40}$)alkyl are substituted ($C_1$-$C_{20}$)alkyl, substituted ($C_1$-$C_{10}$)alkyl, trifluoromethyl, and ($C_{45}$)alkyl. Preferably, each ($C_1$-$C_5$)alkyl independently is methyl, trifluoromethyl, ethyl, 1-propyl, or 2-methylethyl.

The term "($C_1$-$C_{20}$)alkylene" means a saturated straight or branched chain diradical of from 1 to 20 carbon atoms that is unsubstituted or substituted by one or more $R^S$. Preferably, ($C_1$-$C_{20}$)alkylene, together with atoms of formula (I) through which the ($C_1$-$C_{20}$)alkylene is bonded, comprise a 5- or 6-membered ring. Examples of unsubstituted ($C_1$-$C_{20}$)alkylene are unsubstituted ($C_1$-$C_{10}$)alkylene, including unsubstituted 1,2-($C_1$-$C_{10}$)alkylene; —$CH_2$—, —$CH_2CH_2$—, —($CH_2$)$_3$—, —($CH_2$)$_4$—, —($CH_2$), —, —($CH_2$)$_6$—, —($CH_2$)$_7$—, —($CH_2$)$_8$—, and —($CH_2$)$_4$C(H)(CH$_3$)—. Examples of substituted ($C_1$-$C_{20}$)alkylene are substituted ($C_1$-$C_{10}$)alkylene, —$CF_2$—, —C(O)—, and —($CH_2$)$_{14}$C(CH$_3$)$_2$(CH$_2$)$_5$-(i.e., a 6,6-dimethyl substituted normal-1,20-eicosylene).

The term "($C_6$-$C_{40}$)aryl" means an unsubstituted or substituted (by one or more $R^S$) mono-, bi- or tricyclic aromatic hydrocarbon radical of from 6 to 40 total carbon atoms, of which at least from 6 to 14 carbon atoms are ring carbon atoms, and the mono-, bi- or tricyclic radical comprises 1, 2 or 3 rings (first, second, and third rings, respectively), wherein any second or third ring independently is fused or non-fused to a first ring or each other, and the first ring is aromatic and, preferably, at least one of any second or third rings is aromatic. Examples of unsubstituted ($C_6$-$C_{40}$)aryl are unsubstituted ($C_6$-$C_{20}$)aryl; unsubstituted ($C_6$-$C_{18}$)aryl; unsubstituted ($C_6$-$C_{12}$)aryl; phenyl; fluorenyl; tetrahydrofluorenyl; indacenyl; hexahydroindacenyl; indenyl; dihydroindenyl; naphthyl; tetrahydronaphthyl; and phenanthrene. Examples of substituted ($C_6$-$C_{40}$)aryl are substituted ($C_6$-$C_{20}$)aryl; substituted ($C_6$-$C_{18}$)aryl; substituted ($C_6$-$C_{12}$)aryl; 2-($C_1$-$C_5$)alkyl-phenyl; 2,4-bis($C_1$-$C_5$)alkyl-phenyl; 2,4-bis[($C_{20}$)alkyl]-phenyl; polyfluorophenyl; pentafluorophenyl; and fluoren-9-one-1-yl. A preferred substituted ($C_6$-$C_{12}$)aryl is a substituted ($C_6$)aryl, more preferably 2,6-bis(1-methylethyl)phenyl.

The term "($C_3$-$C_{40}$)cycloalkyl" means a saturated cyclic hydrocarbon radical of from 3 to 40 carbon atoms that is unsubstituted or substituted by one or more $R^S$. Examples of unsubstituted ($C_3$-$C_{40}$)cycloalkyl are unsubstituted ($C_3$-$C_{20}$)cycloalkyl, unsubstituted ($C_3$-$C_{10}$)cycloalkyl, cyclopropyl, cyclobutyl, cyclopentyl, cyclohexyl, cycloheptyl, cyclooctyl, cyclononyl, and cyclodecyl. Examples of substituted ($C_3$-$C_{40}$)cycloalkyl are substituted ($C_3$-$C_{20}$)cycloalkyl, substituted ($C_3$-$C_{10}$)cycloalkyl, cyclopentanon-2-yl, and 1-fluorocyclohexyl.

Examples of ($C_1$-$C_{40}$)hydrocarbylene are unsubstituted or substituted ($C_6$-$C_{40}$)arylene, ($C_3$-$C_{40}$)cycloalkylene, and ($C_1$-$C_{40}$)alkylene (e.g., ($C_1$-$C_{20}$)alkylene). In some embodiments, the diradicals are on adjacent carbon atoms (i.e., 1,2-diradicals), or spaced apart by one, two, or more intervening carbon atoms (e.g., respective 1,3-diradicals, 1,4-diradicals, etc.). Preferred is a 1,2-, 1,3-, 1,4-, or an alpha, omega-diradical (i.e., having maximum spacing between the radical carbons), more preferably a 1,2-diradical. More preferred are 1,2-diradical versions of ($C_6$-$C_{18}$)arylene, ($C_3$-$C_{20}$)cycloalkylene, and ($C_2$-$C_{20}$)alkylene.

The term "($C_1$-$C_{40}$)heterohydrocarbyl" means a heterohydrocarbon radical of from 1 to 40 carbon atoms and one or more heteroatoms N (when comprising —N═, as in certain nitrogen containing heteroaryl groups, e.g., an isoxazolyl); O; S; S(O); S(O)$_2$; Si($R^C$)$_2$; P($R^P$); and N($R^N$), wherein independently each $R^c$ is unsubstituted ($C_1$-$C_{18}$)hydrocarbyl, each $R^P$ is unsubstituted ($C_1$-$C_{18}$)hydrocarbyl; and each $R^N$ is unsubstituted ($C_1$-$C_{18}$)hydrocarbyl. The term "($C_1$-$C_{40}$)heterohydrocarbylene" means a heterohydrocarbon diradical of from 1 to 40 carbon atoms and one or more heteroatoms Si($R^C$)$_2$, P($R^P$), N($R^N$), N, O, S, S(O), and S(O)$_2$ as defined above. The heterohydrocarbon radical and each of the heterohydrocarbon diradicals independently are on a carbon atom or heteroatom thereof. Each heterohydrocarbon radical and diradical independently is unsubstituted or substituted (by one or more $R^S$), aromatic or non-aromatic, saturated or unsaturated, straight chain or branched chain, cyclic (including mono- and poly-cyclic, fused and non-fused polycyclic) or acyclic, or a combination of two or more thereof; and each heterohydrocarbon is the same as or different from another heterohydrocarbon radical and diradical, respectively.

Preferably, a ($C_1$-$C_{40}$)heterohydrocarbyl independently is unsubstituted or substituted ($C_1$-$C_{40}$)heteroalkyl, ($C_2$-$C_{40}$)heterocycloalkyl, ($C_2$-$C_{40}$)heterocycloalkyl-($C_1$-$C_{20}$)alkylene, ($C_3$-$C_{40}$)cycloalkyl-($C_1$-$C_{20}$)heteroalkylene, ($C_2$-$C_{40}$)heterocycloalkyl-($C_1$-$C_{20}$)heteroalkylene, ($C_1$-$C_{40}$)heteroaryl, ($C_1$-$C_{20}$)heteroaryl-($C_1$-$C_{20}$)alkylene, ($C_6$-$C_{20}$)aryl-($C_1$-$C_{20}$)heteroalkylene, or ($C_1$-$C_{20}$)heteroaryl-($C_1$-$C_{20}$)heteroalkylene. More preferably, a ($C_1$-$C_{40}$)heterohydrocarbyl independently is unsubstituted or substituted ($C_1$-$C_{20}$)heterohydrocarbyl, e.g., ($C_1$-$C_{20}$)heteroalkyl, ($C_2$-$C_{20}$)heterocycloalkyl, ($C_2$-$C_{20}$)heterocycloalkyl-($C_1$-$C_{20}$)alkylene, ($C_3$-$C_{20}$)cycloalkyl-($C_1$-$C_{20}$)heteroalkylene, ($C_2$-$C_{20}$)heterocycloalkyl-($C_1$-$C_{20}$)heteroalkylene, ($C_1$-$C_{20}$)heteroaryl, ($C_1$-$C_{20}$)heteroaryl-($C_1$-$C_{20}$)alkylene, ($C_6$-$C_{20}$)aryl-($C_1$-$C_{20}$)heteroalkylene, or ($C_1$-$C_{20}$)heteroaryl-($C_1$-$C_{20}$)heteroalkylene. Still more preferably, a ($C_1$-$C_{40}$)heterohydrocarbyl independently is unsubstituted or substituted ($C_1$-$C_{18}$)heterohydrocarbyl, e.g., ($C_1$-$C_{18}$)heteroalkyl, ($C_2$-$C_{18}$)heterocycloalkyl, ($C_2$-$C_{12}$)heterocycloalkyl-($C_1$-$C_6$)alkylene, ($C_3$-$C_{12}$)cycloalkyl-($C_1$-$C_6$)heteroalkylene, ($C_2$-$C_{12}$)heterocycloalkyl-($C_1$-$C_6$)heteroalkylene, ($C_1$-$C_{12}$)heteroaryl, ($C_1$-$C_{12}$)heteroaryl-($C_1$-$C_6$)alkylene, ($C_6$-$C_{18}$)aryl-($C_1$-$C_6$)heteroalkylene, or ($C_1$-$C_{12}$)heteroaryl-($C_1$-$C_6$)heteroalkylene. Preferably, any ($C_2$-$C_{18}$)heterocycloalkyl independently is unsubstituted or substituted ($C_2$-$C_9$)heterocycloalkyl.

Examples of ($C_1$-$C_{40}$)heteroalkyl and ($C_1$-$C_{20}$)heteroalkylene are saturated straight or branched chain radical or diradical, respectively, of from 1 to 40 or 1 to 20 carbon atoms, respectively, and one or more of the heteroatoms Si($R^C$)$_2$, P($R^P$), N($R^N$), N, O, S, S(O), and S(O)$_2$ as defined above, wherein the ($C_1$-$C_{40}$)heteroalkyl and ($C_1$-$C_{20}$)heteroalkylene independently are unsubstituted or substituted by one or more $R^S$.

Examples of unsubstituted $(C_2\text{-}C_{40})$heterocycloalkyl are unsubstituted $(C_2\text{-}C_{20})$heterocycloalkyl, unsubstituted $(C_2\text{-}C_{10})$heterocycloalkyl, aziridin-1-yl, oxetan-2-yl, tetrahydrofuran-3-yl, pyrrolidin-1-yl, tetrahydrothiophen-S,S-dioxide-2-yl, morpholin-4-yl, 1,4-dioxan-2-yl, hexahydroazepin-4-yl, 3-oxa-cyclooctyl, 5-thia-cyclononyl, and 2-azacyclodecyl.

Examples of unsubstituted $(C_1\text{-}C_{40})$heteroaryl are unsubstituted $(C_1\text{-}C_{20})$heteroaryl, unsubstituted $(C_1\text{-}C_{10})$heteroaryl, pyrrol-1-yl; pyrrol-2-yl; furan-3-yl; thiophen-2-yl; pyrazol-1-yl; isoxazol-2-yl; isothiazol-5-yl; imidazol-2-yl; oxazol-4-yl; thiazol-2-yl; 1,2,4-triazol-1-yl; 1,3,4-oxadiazol-2-yl; 1,3,4-thiadiazol-2-yl; tetrazol-1-yl; tetrazol-2-yl; tetrazol-5-yl; pyridine-2-yl; pyrimidin-2-yl; pyrazin-2-yl; indol-1-yl; benzimidazole-1-yl; quinolin-2-yl; and isoquinolin-1-yl.

The terms "halogen" and "halogen atom" mean a fluoro (F), chloro (Cl), bromo (Br), or iodo (I) radical. Preferably, halogen or halogen atom is fluoro or chloro, more preferably fluoro.

Preferably, in the metal-ligand complex of formula (I), there are no O—O, S—S, or O—S bonds, other than O—S bonds in an S(O) or S(O)$_2$ diradical functional group.

Preferably, in the metal-ligand complex of formula (I), M is Ti, Zr, or Hf.

In some embodiments of the metal-ligand complex of formula (I), one of $R^1$ and $R^2$ and one of $R^3$ and $R^4$ are taken together to form

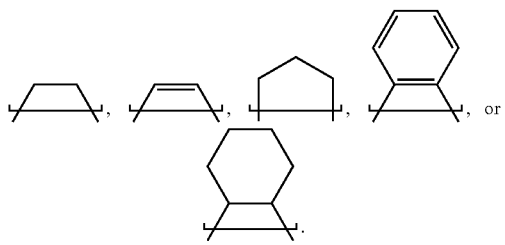

In some embodiments of formula (I), two occurrences of L are taken together to form a $(C_2\text{-}C_{40})$hydrocarbylene or $(C_1\text{-}C_{40})$heterohydrocarbylene, or $(R^D)_2C{=}C(R^D){-}C(R^D){=}C(R^D)_2$, wherein each $R^D$ independently is H, unsubstituted $(C_1\text{-}C_6)$alkyl, phenyl, or naphthyl.

In some embodiments of formula (I), J and one of $R^1$, $R^2$, $R^3$, and $R^4$ are taken together to form $(C_2\text{-}C_{40})$hydrocarbylene or $(C_1\text{-}C_{40})$heterohydrocarbylene.

In some embodiments of formula (I), one occurrence of L and one of $R^1$, $R^2$, $R^3$, and $R^4$ are optionally taken together to form $(C_2\text{-}C_{40})$hydrocarbylene or $(C_1\text{-}C_{40})$heterohydrocarbylene.

In some embodiments of formula (I), one occurrence of X and one of $R^1$, $R^2$, $R^3$, and $R^4$ are optionally taken together to form $(C_1\text{-}C_{40})$heterohydrocarbylene.

In some embodiments of formula (I), X and J are taken together to form a monoanionic bidentate moiety X-J, provided that when X-J is bound to M to form a fragment having the structure

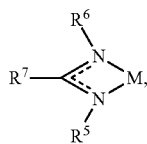

then $R^5$, $R^6$, and $R^7$ are each independently hydrogen, $(C_1\text{-}C_{40})$hydrocarbyl-, $((C_1\text{-}C_{40})$hydrocarbyl)O—, $((C_1\text{-}C_{40})$hydrocarbyl)S—, $((C_1\text{-}C_{40})$hydrocarbyl)$_3$Si—, or $(C_1\text{-}C_{40})$heterohydrocarbyl-. In these embodiments, X-J can be bound to one of $R^1$, $R^2$, $R^3$, or $R^4$ via one of $R^5$, $R^6$, or $R^7$. Thus, one of $R^1$, $R^2$, $R^3$, $R^4$ is optionally taken together with one of $R^5$, $R^6$, and $R^7$ to form a $(C_2\text{-}C_{40})$hydrocarbylene or $(C_1\text{-}C_{40})$heterohydrocarbylene. Also, when X and J are taken together to form the monoanionic bidentate moiety X-J, and X-J is bound to M via an anionic nitrogen and a Lewis base nitrogen, then X-J and M form a four-membered metallocycle (for example, that shown above in this paragraph) or a six-membered metallocycle (not a five-membered metallocycle).

In some embodiments, the metal-ligand complex has formula (II)

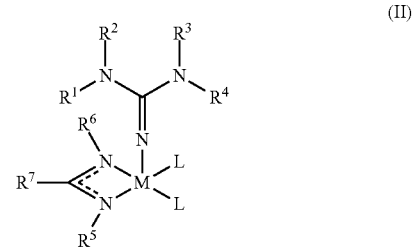

wherein L, M, $R^1$, $R^2$, $R^3$, and $R^4$ are as defined as for formula (I); $R^5$, $R^6$, and $R^7$ are each independently hydrogen, $(C_1\text{-}C_{40})$hydrocarbyl-, $((C_1\text{-}C_{40})$hydrocarbyl)O—, $((C_1\text{-}C_{40})$hydrocarbyl)S—, $((C_1\text{-}C_{40})$hydrocarbyl)$_3$Si—, or $(C_1\text{-}C_{40})$heterohydrocarbyl-; one occurrence of L and any one of $R^1$, $R^2$, $R^3$, and $R^4$ are optionally taken together to form $(C_2\text{-}C_{40})$hydrocarbylene or $(C_1\text{-}C_{40})$heterohydrocarbylene; any two of $R^1$, $R^2$, $R^3$, and $R^4$ are optionally taken together to form a $(C_2\text{-}C_{40})$hydrocarbylene or $(C_1\text{-}C_{40})$heterohydrocarbylene; one of $R^5$, $R^6$, and $R^7$ is optionally taken together with one of $R^1$, $R^2$, $R^3$, $R^4$, and L to form a $(C_2\text{-}C_{40})$hydrocarbylene or $(C_1\text{-}C_{40})$heterohydrocarbylene; and the two occurrences of L are optionally taken together to form a $(C_2\text{-}C_{40})$hydrocarbylene or $(C_1\text{-}C_{40})$heterohydrocarbylene, or $(R^D)_2C{=}C(R^D){-}C(R^D){=}C(R^D)_2$, wherein each $R^D$ independently is H, unsubstituted $(C_1\text{-}C_6)$alkyl, phenyl, or naphthyl.

Specific examples of metal-ligand complexes of formula (II) include

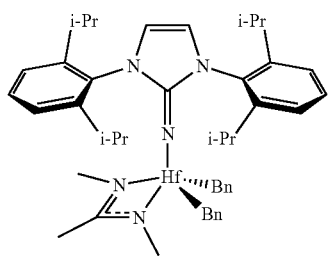

-continued
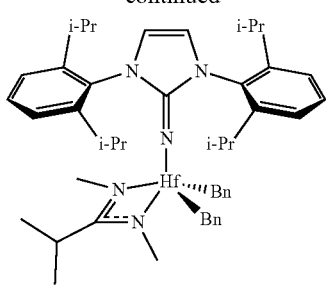
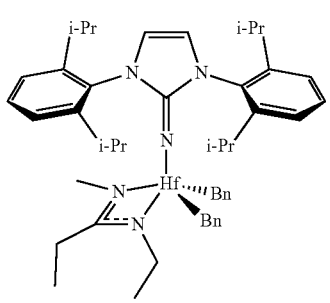
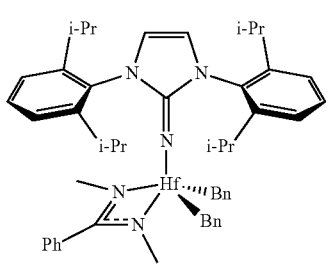
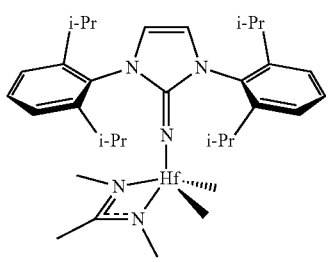
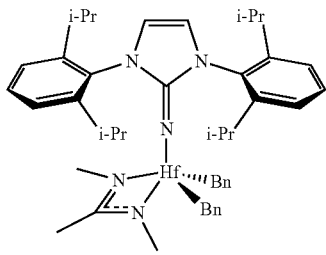
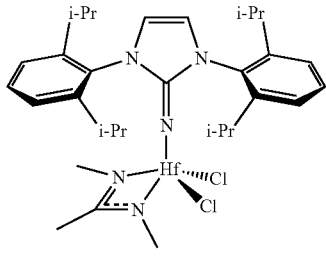
-continued
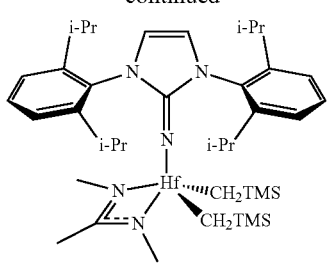
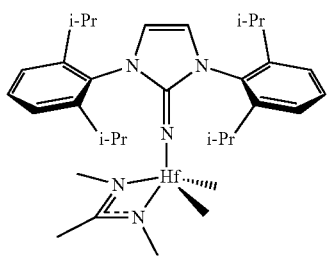
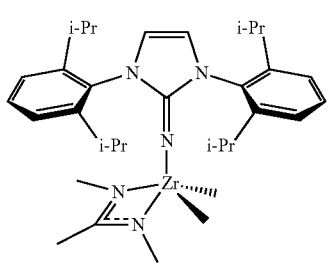
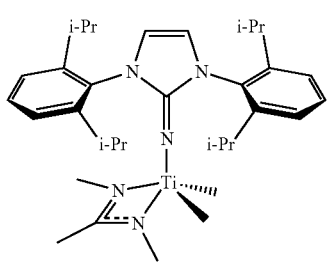
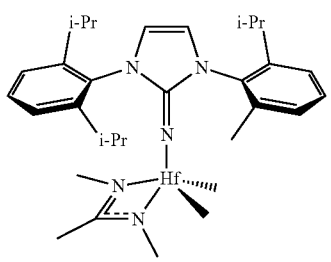
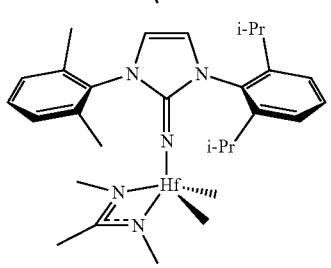

11
-continued
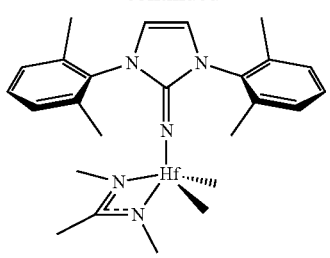
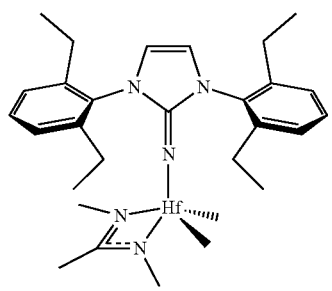
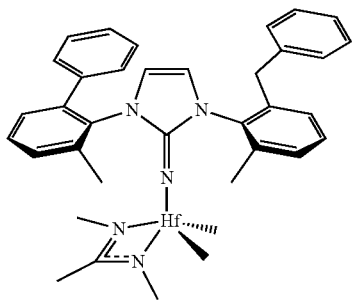
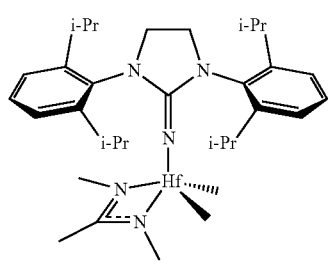
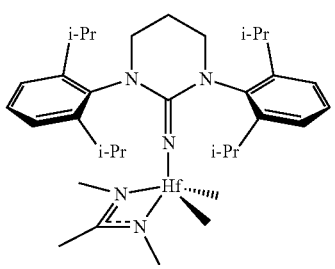
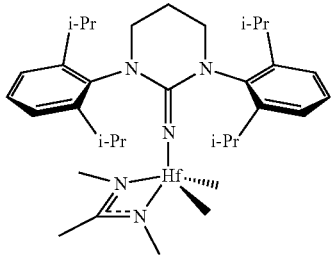
12
-continued
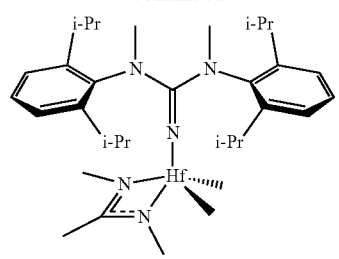
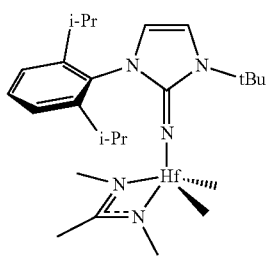
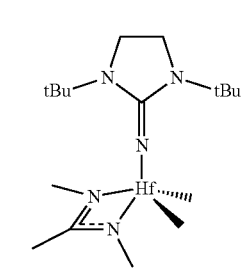
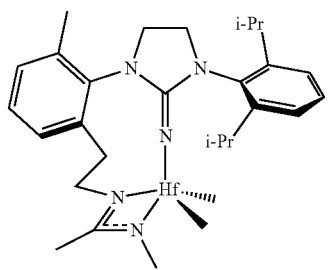
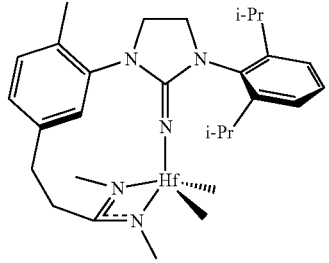
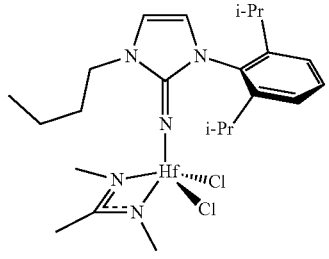

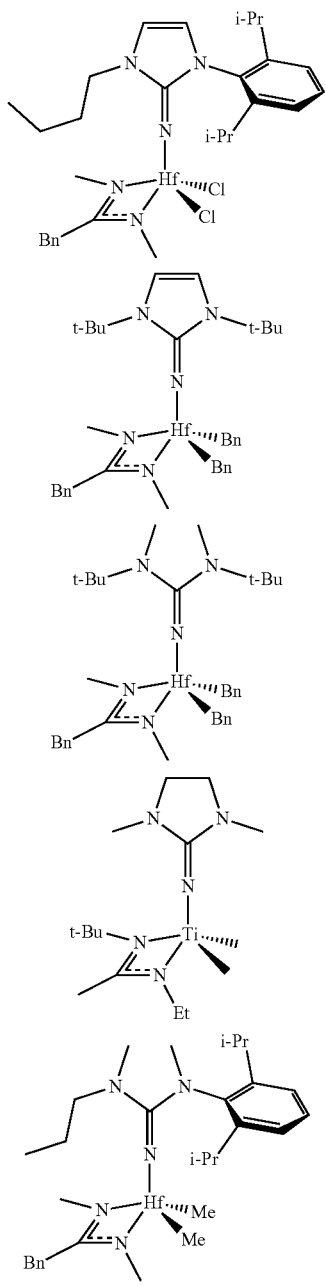

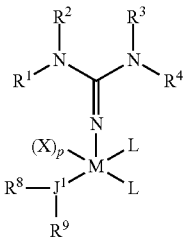

(III)

wherein L, M, p, $R^1$, $R^2$, $R^3$, $R^4$, and X are defined as for formula (I); $J^1$ is N or P; $R^8$ and $R^9$ are each independently hydrogen, $(C_1\text{-}C_{40})$hydrocarbyl-, $((C_1\text{-}C_{40})$hydrocarbyl)O—, $((C_1\text{-}C_{40})$hydrocarbyl)S—, $((C_1\text{-}C_{40})$hydrocarbyl)$_3$Si—, or $(C_1\text{-}C_{40})$heterohydrocarbyl-; one occurrence of L and any one of $R^1$, $R^2$, $R^3$, and $R^4$ are optionally taken together to form $(C_2\text{-}C_{40})$hydrocarbylene or $(C_1\text{-}C_{40})$heterohydrocarbylene; the two occurrences of L are optionally taken together to form a $(C_2\text{-}C_{40})$hydrocarbylene or $(C_1\text{-}C_{40})$heterohydrocarbylene, or $(R^D)_2C=C(R^D)\text{—}C(R^D)=C(R^D)_2$, wherein each $R^D$ independently is H, unsubstituted $(C_1\text{-}C_6)$alkyl, phenyl, or naphthyl; any two of $R^1$, $R^2$, $R^3$, and $R^4$ optionally are taken together to form a $(C_2\text{-}C_{40})$hydrocarbylene or $(C_1\text{-}C_{40})$heterohydrocarbylene; $R^8$ and $R^9$ are optionally taken together to form $(C_2\text{-}C_{40})$hydrocarbylene or $(C_1\text{-}C_{40})$heterohydrocarbylene; $R^8$ and $R^9$ are optionally taken together to form a group double bonded to $J^1$; one of $R^8$ and $R^9$ is optionally taken together with one of $R^1$, $R^2$, $R^3$, $R^4$, and L to form a $(C_2\text{-}C_{40})$hydrocarbylene or $(C_1\text{-}C_{40})$heterohydrocarbylene; one of $R^8$ and $R^9$ is optionally covalently bonded to X; and X and any one of $R^1$, $R^2$, $R^3$, and $R^4$ are optionally taken together to form $(C_1\text{-}C_{40})$heterohydrocarbylene.

Specific examples of metal-ligand complexes of formula (III) include

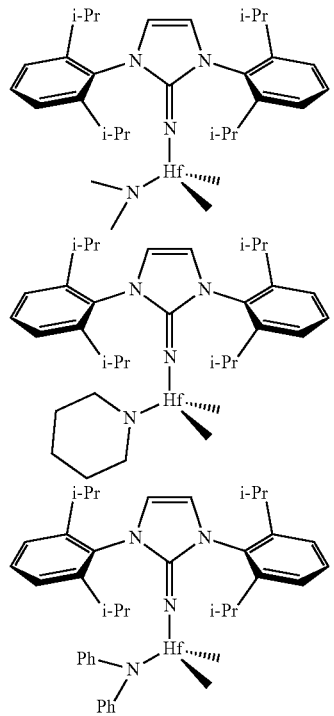

and combinations thereof, wherein Bn is benzyl, Et is ethyl, iPr is isopropyl, t-Bu is t-butyl, and TMS is trimethylsilyl.

In some embodiments, the metal-ligand complex has formula (III)

-continued
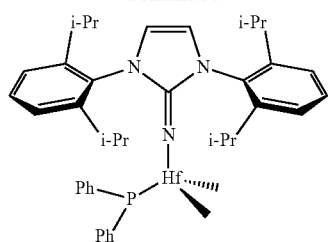
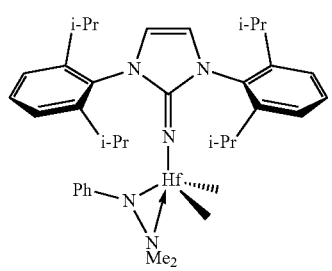
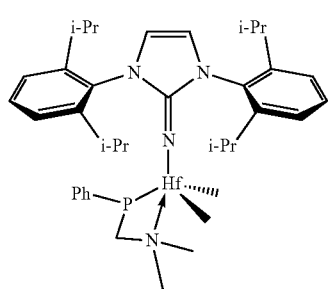
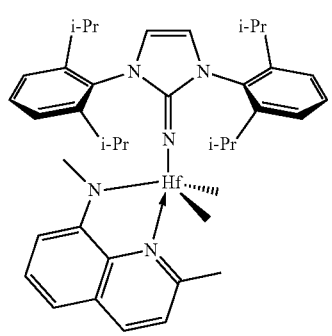
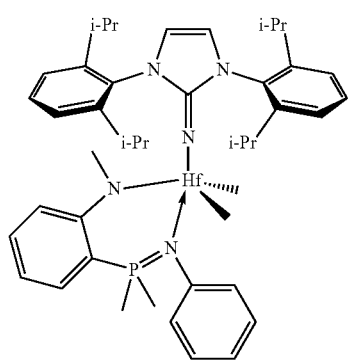
-continued
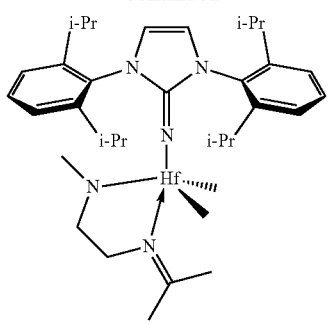
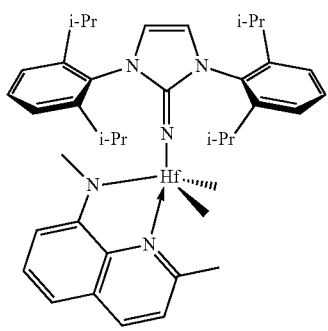
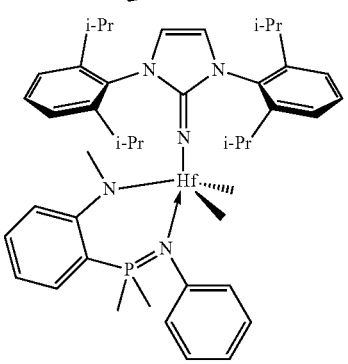
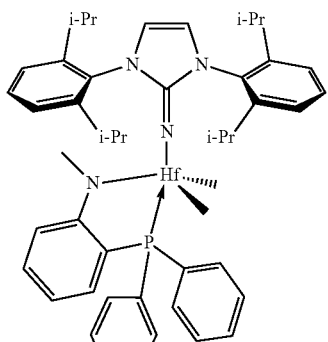
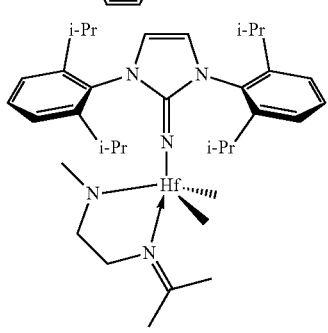

-continued
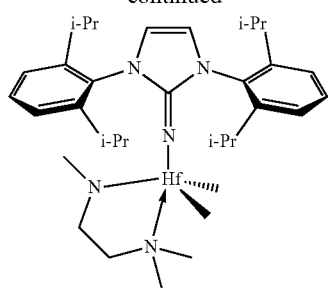
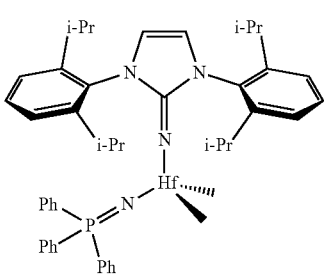
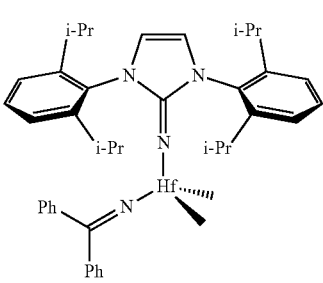
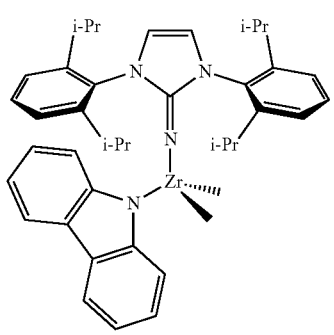
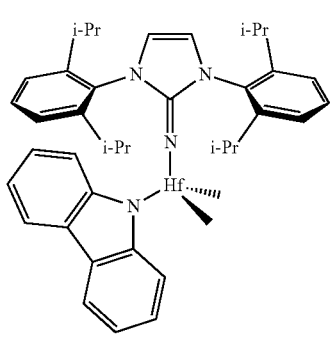
-continued
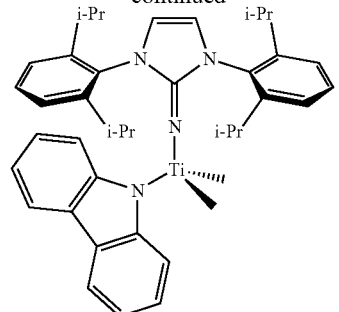
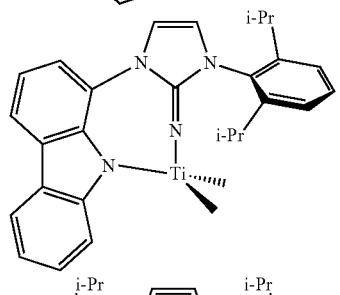
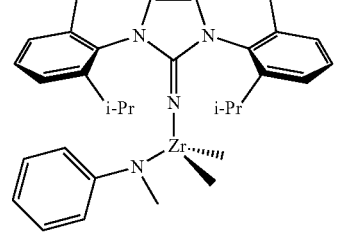
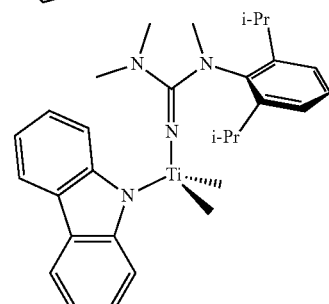
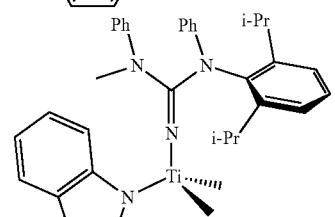
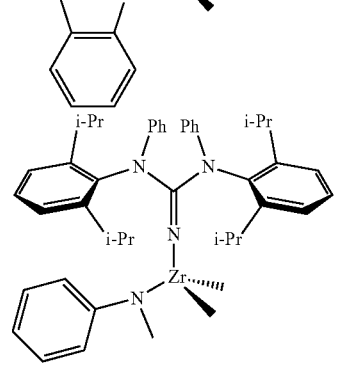
and combinations thereof.

In some embodiments, the metal-ligand complex has formula (IV)

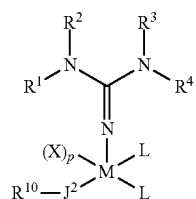
(IV)

wherein L, M, p, $R^1$, $R^2$, $R^3$, $R^4$, and X are as defined as for formula (I); $J^2$ is O or S; and $R^{10}$ is $(C_1-C_{40})$hydrocarbyl-, $((C_1-C_{40})$hydrocarbyl$)_3$Si—, or $(C_1-C_{40})$heterohydrocarbyl-; one occurrence of L and any one of $R^1$, $R^2$, $R^3$, and $R^4$ are optionally taken together to form $(C_2-C_{40})$hydrocarbylene or $(C_1-C_{40})$heterohydrocarbylene; any two of $R^1$, $R^2$, $R^3$, and $R^4$ optionally are taken together to form a $(C_2-C_{40})$ hydrocarbylene or $(C_1-C_{40})$heterohydrocarbylene; X and any one of $R^1$, $R^2$, $R^3$, and $R^4$ are optionally taken together to form $(C_1-C_{40})$heterohydrocarbylene; and $R^{10}$ is optionally taken together with one of $R^1$, $R^2$, $R^3$, $R^4$, and L to form a $(C_1-C_{40})$heterohydrocarbylene; and $R^{10}$ is optionally covalently bonded to X.

Specific examples of metal-ligand complexes of formula (IV) include

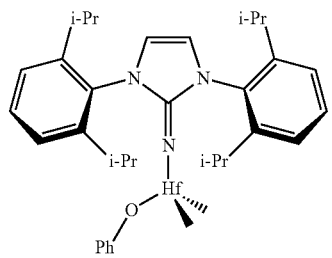

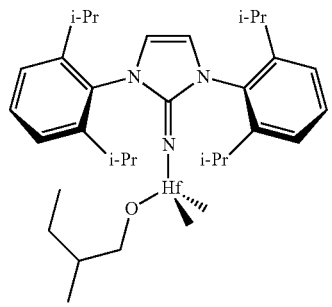

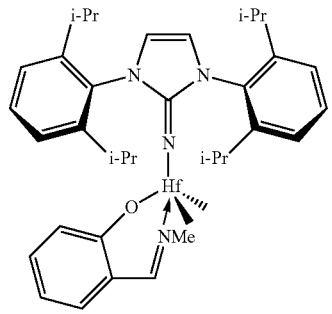

-continued

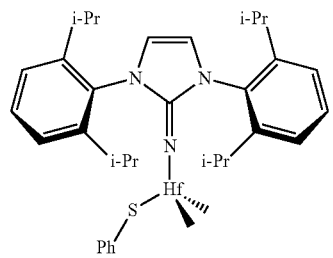

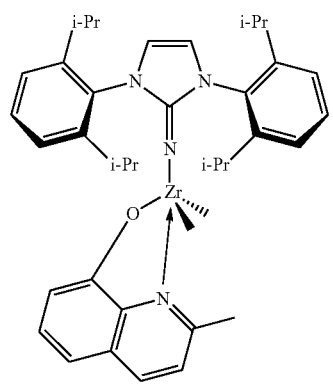

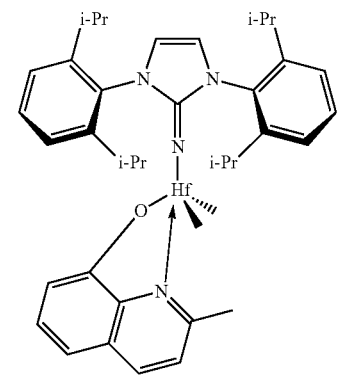

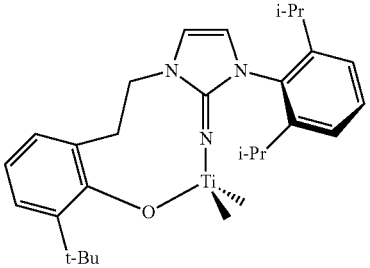

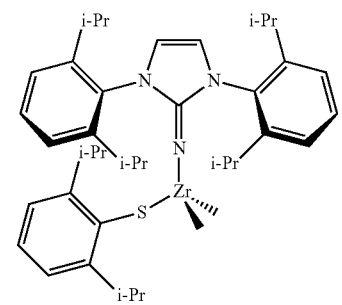

-continued

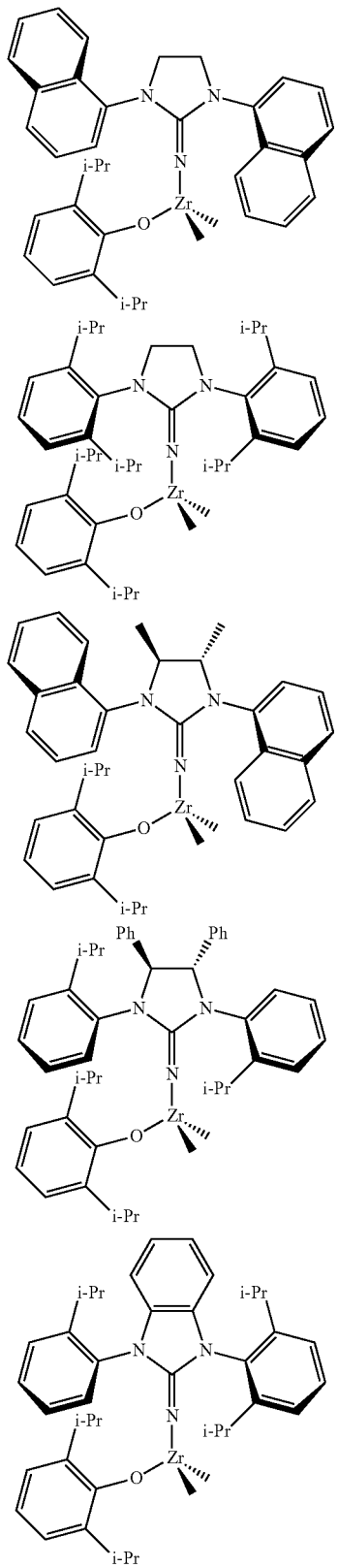

and combinations thereof.

In some embodiments, the metal-ligand complex has formula (V)

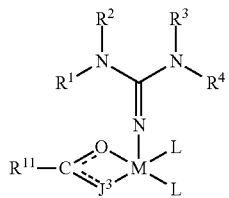

wherein L, M, $R^1$, $R^2$, $R^3$, and $R^4$ are as defined for formula (I); $J^3$ is O or $NR^{12}$; $R^{11}$ and $R^{12}$ are each independently hydrogen, $(C_1-C_{40})$hydrocarbyl-, $((C_1-C_{40})$hydrocarbyl)O—, $((C_1-C_{40})$hydrocarbyl)S—, $((C_1-C_{40})$hydrocarbyl)$_3$Si—, or $(C_1-C_{40})$heterohydrocarbyl-; $R^{11}$ and $R^{12}$ are optionally taken together to form $(C_2-C_{40})$hydrocarbylene or $(C_1-C_{40})$heterohydrocarbylene; one of $R^{11}$ and $R^{12}$ is optionally taken together with one of $R^1$, $R^2$, $R^3$, $R^4$, and L to form a $(C_2-C_{40})$hydrocarbylene or $(C_1-C_{40})$heterohydrocarbylene; two occurrences of L are optionally taken together to form a $(C_2-C_{40})$hydrocarbylene or $(C_1-C_{40})$heterohydrocarbylene, or $(R^D)_2C=C(R^D)-C(R^D)=C(R^D)_2$, wherein each $R^D$ independently is H, unsubstituted $(C_1-C_6)$alkyl, phenyl, or naphthyl; one occurrence of L and one of $R^1$, $R^2$, $R^3$, and $R^4$ are optionally taken together to form $(C_2-C_{40})$hydrocarbylene or $(C_1-C_{40})$heterohydrocarbylene; and any two of $R^1$, $R^2$, $R^3$, and $R^4$ are optionally taken together to form a $(C_2-C_{40})$hydrocarbylene or $(C_1-C_{40})$heterohydrocarbylene.

Specific examples of metal-ligand complexes of formula (V) include

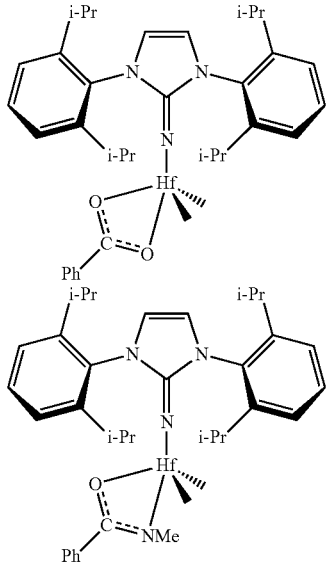

and combinations thereof.

In some embodiments, the metal-ligand complex has formula (VI)

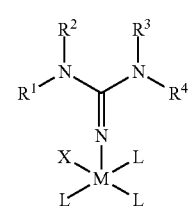

wherein L, M, R¹, R², R³, R⁴, and X are as defined for formula (I); two occurrences of L are optionally taken together to form a $(C_2-C_{40})$hydrocarbylene or $(C_1-C_{40})$heterohydrocarbylene, or $(R^D)_2C=C(R^D)-C(R^D)=C(R^D)_2$, wherein each $R^D$ independently is H, unsubstituted $(C_1-C_6)$alkyl, phenyl, or naphthyl; one occurrence of L and one of R¹, R², R³, and R⁴ are optionally taken together to form $(C_2-C_{40})$hydrocarbylene or $(C_1-C_{40})$heterohydrocarbylene; X and one of R¹, R², R³, and R⁴ are optionally taken together to form $(C_1-C_{40})$heterohydrocarbylene; and any two of R¹, R², R³, and R⁴ are optionally taken together to form a $(C_2-C_{40})$hydrocarbylene or $(C_1-C_{40})$heterohydrocarbylene.

Specific examples of metal-ligand complexes of formula (VI) include

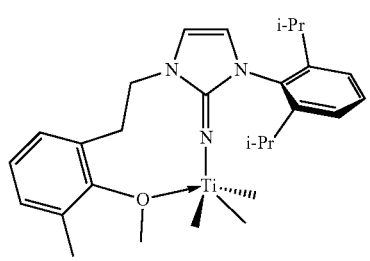

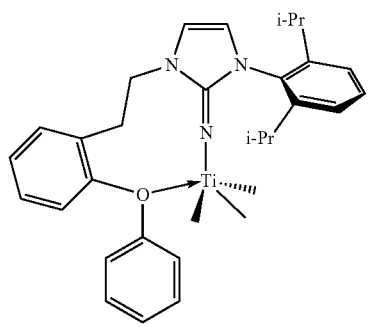

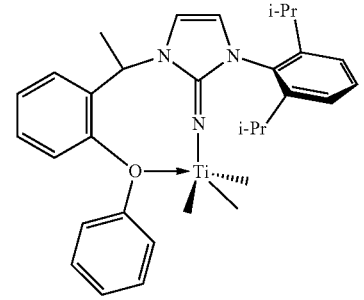

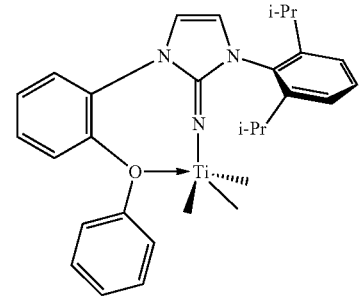

-continued

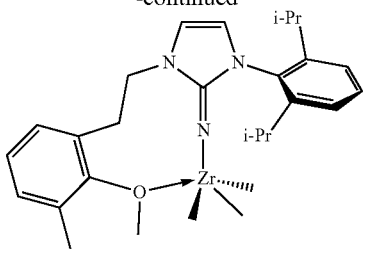

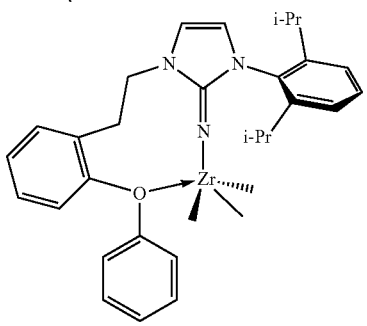

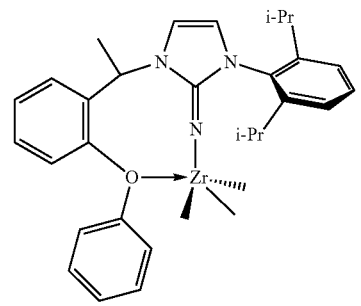

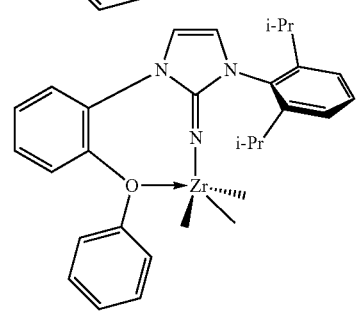

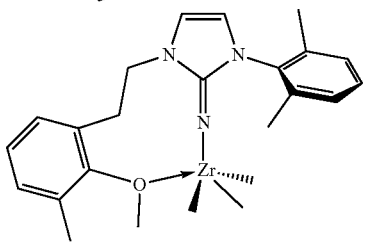

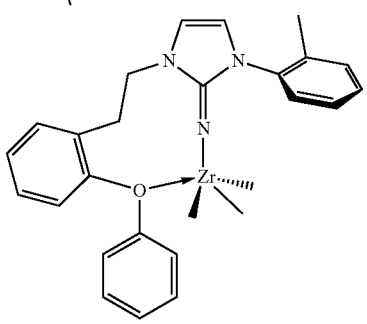

-continued
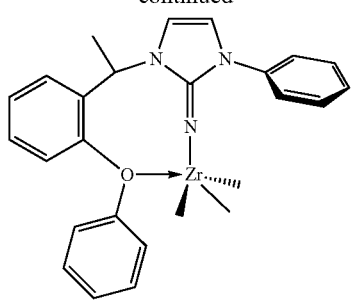
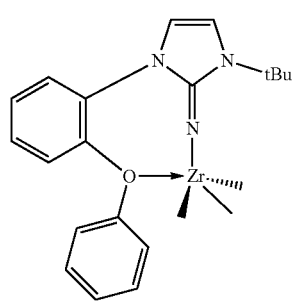
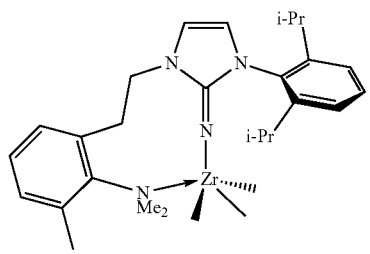
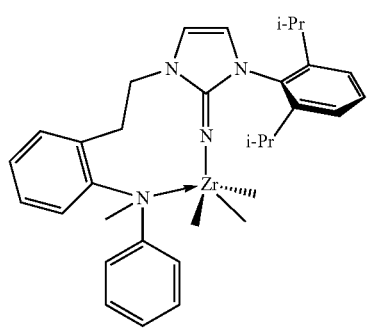
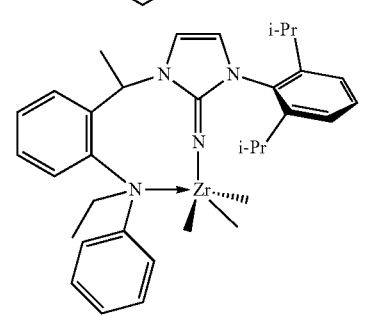
-continued
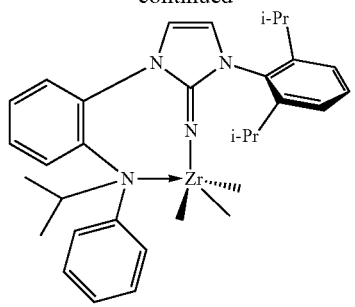
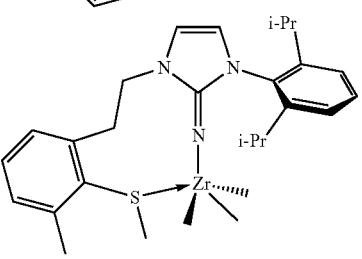
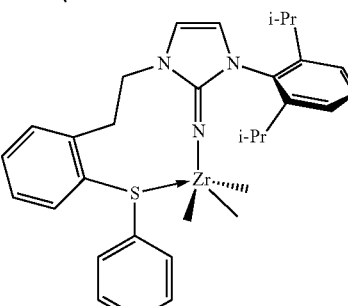
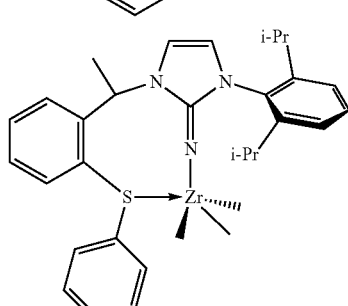
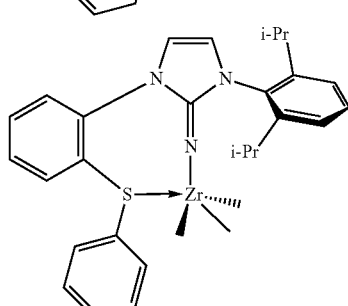
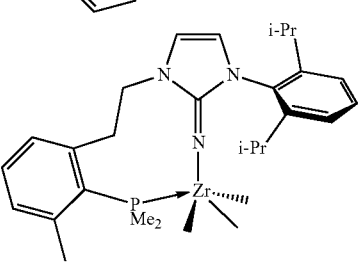

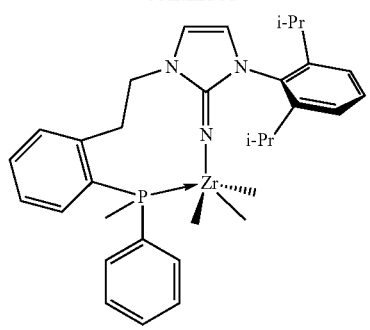
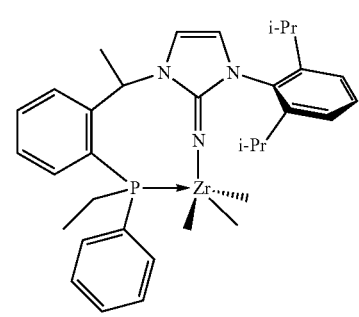
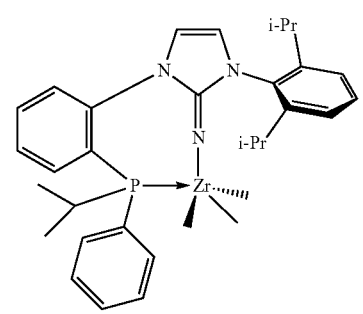
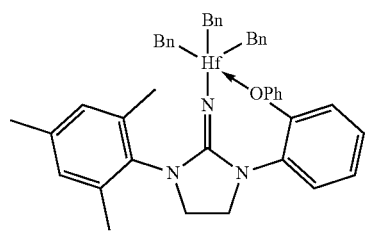
or a combination thereof.
In some embodiments, the metal-ligand complex comprises
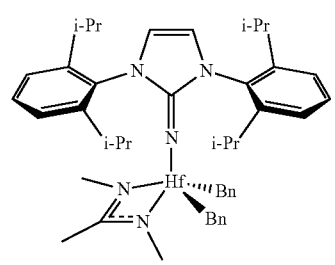
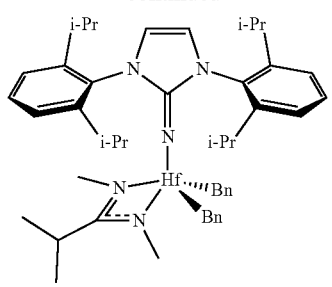
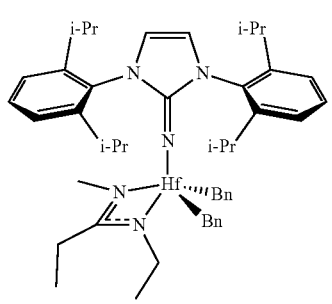
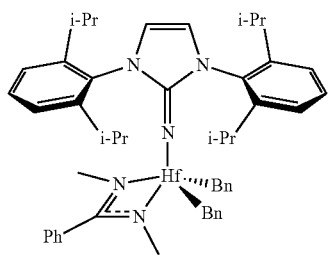
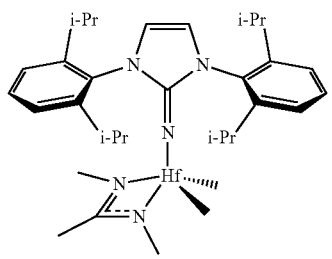
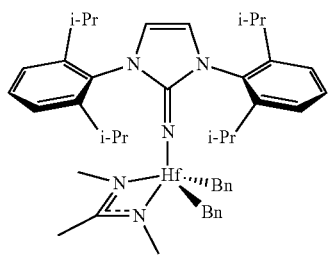
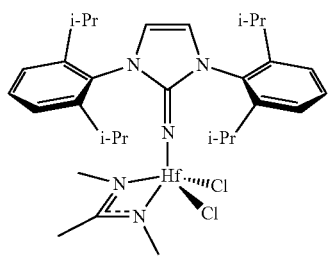

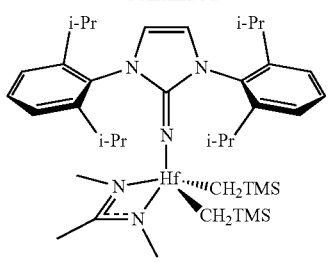
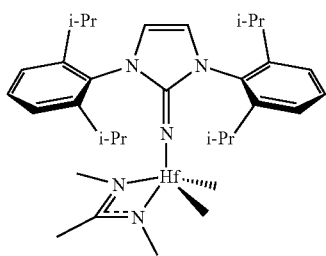
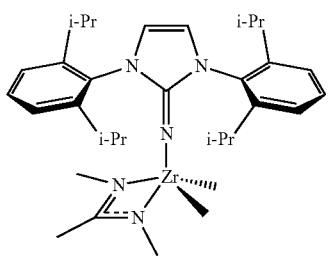
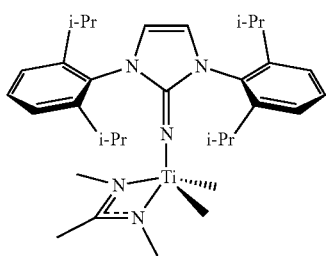
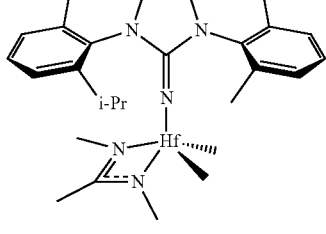
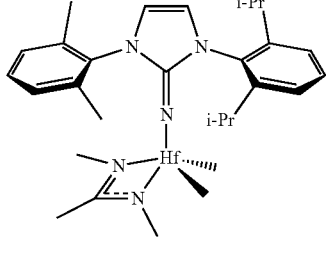
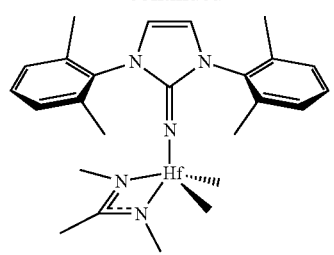
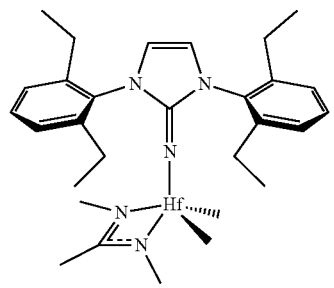
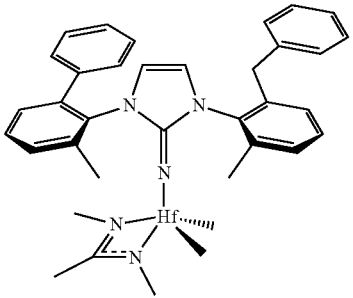
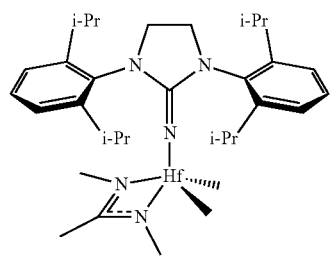
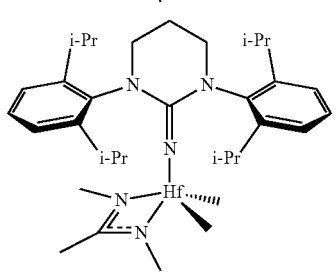
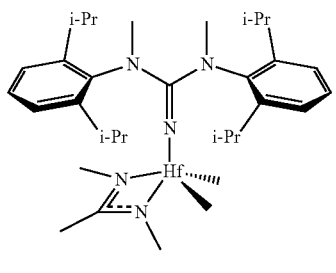

31
-continued
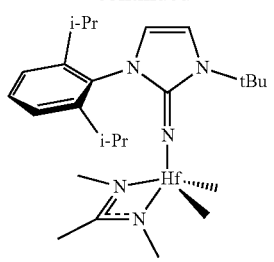
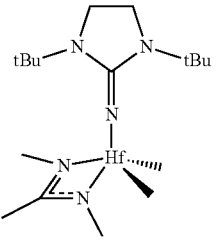
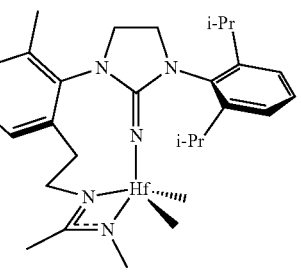
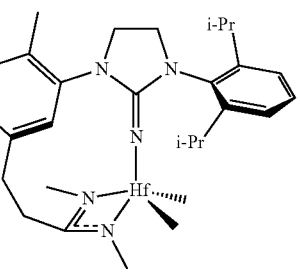
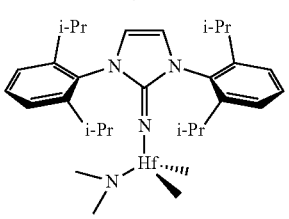
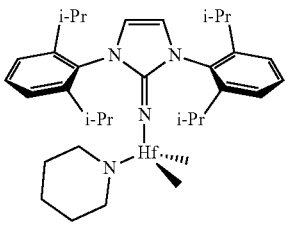
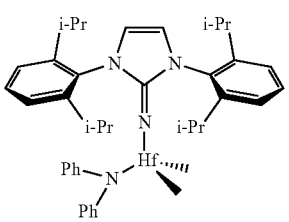
32
-continued
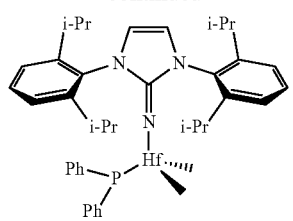
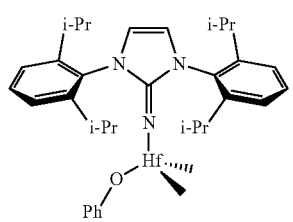
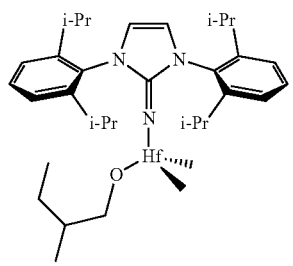
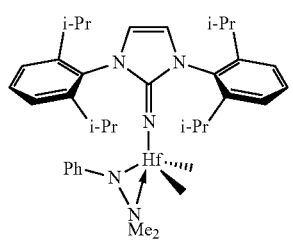
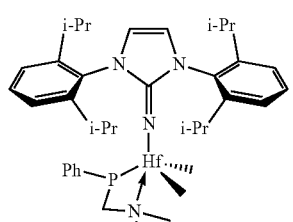
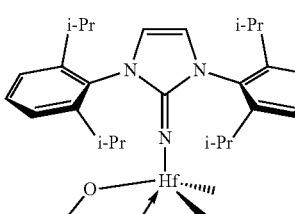

-continued
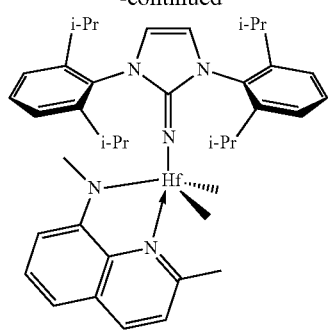
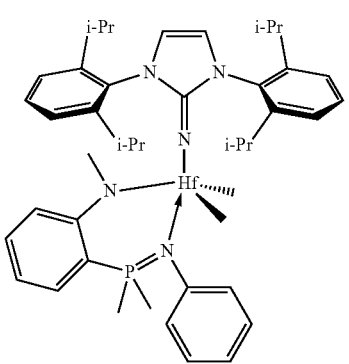
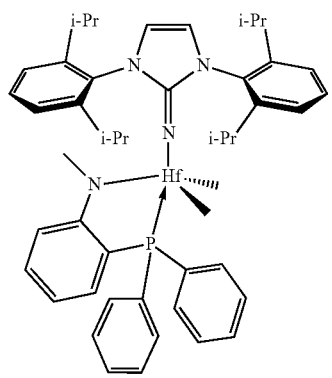
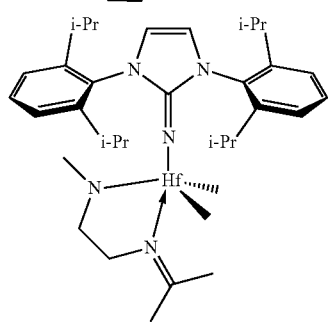
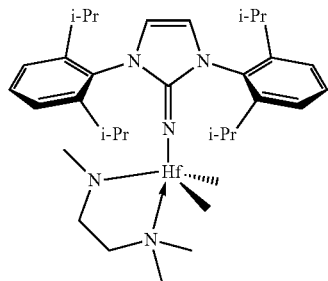
-continued
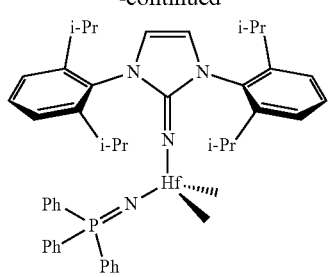
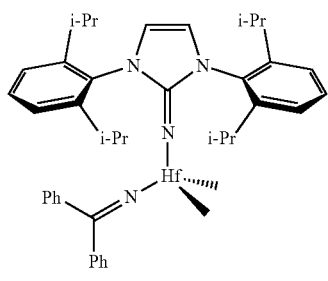
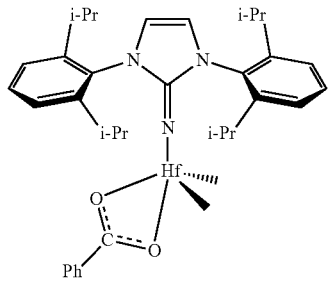
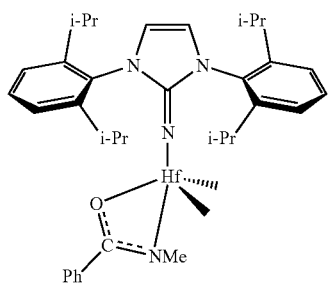
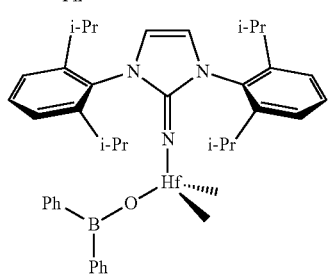
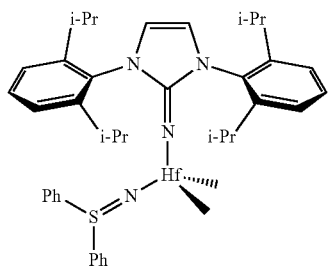

-continued
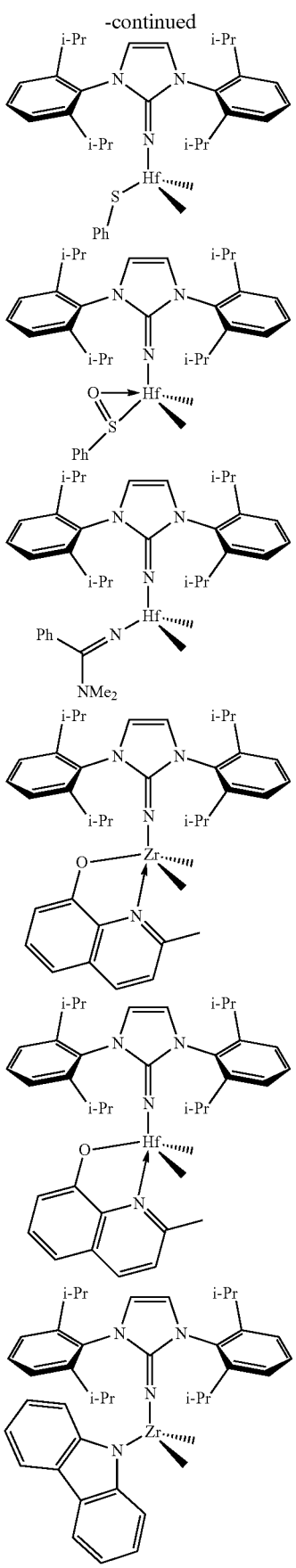
-continued
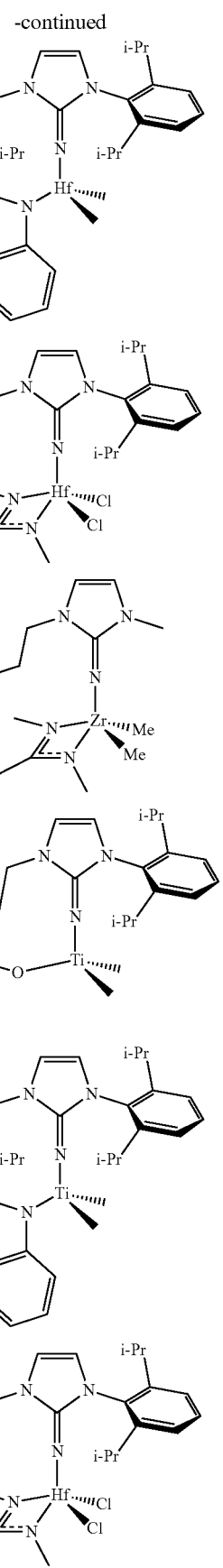

-continued
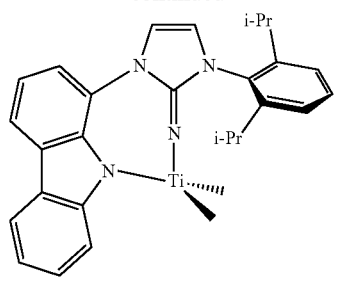
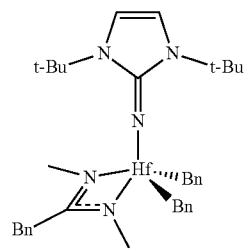
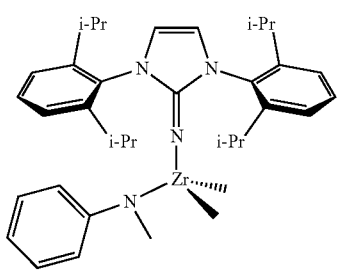
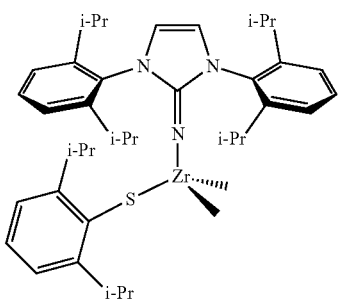
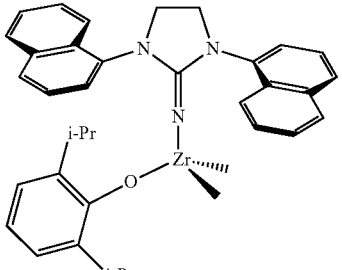
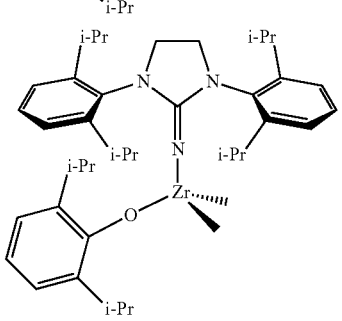
-continued
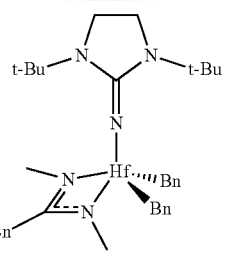
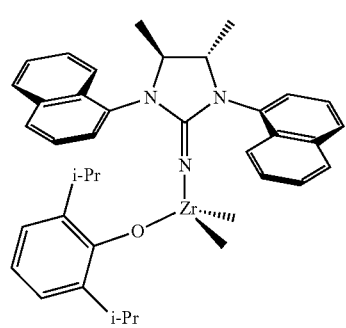
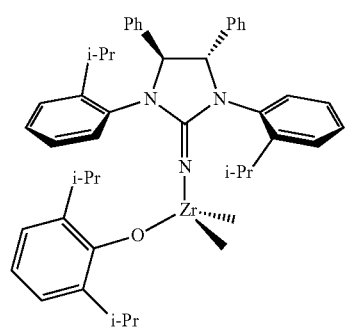
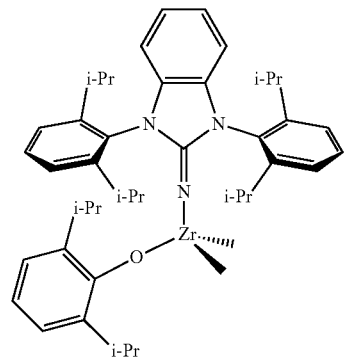
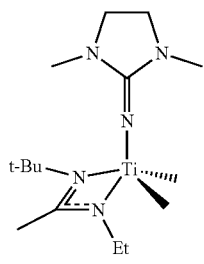

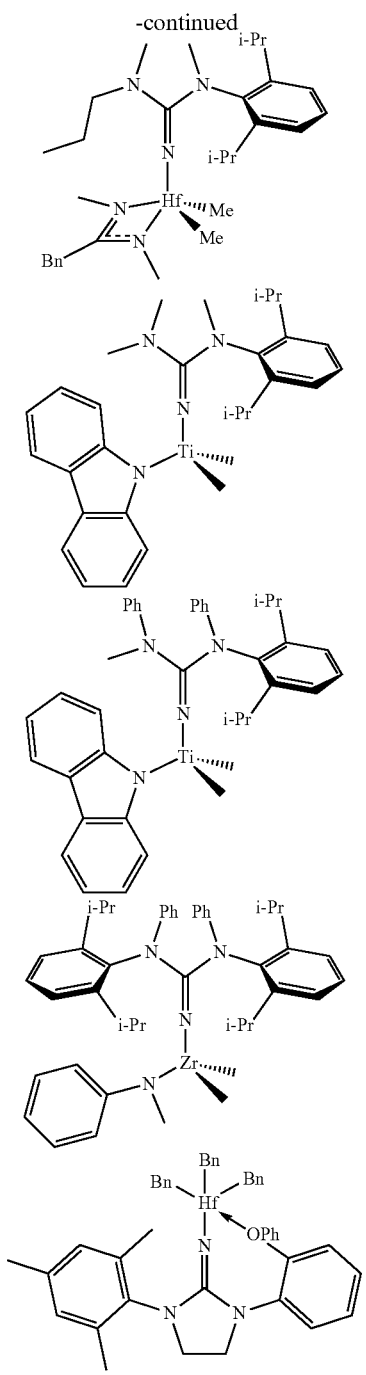

or a combination thereof.

The invention includes a catalyst comprising, or comprising the reaction product of, one or more metal-ligand complexes of any of formulae (I), (II), (III), (IV), (V), and (VI), and one or more activating cocatalysts, wherein a ratio of total number of moles of the one or more metal-ligand complexes to total number of moles of the one or more activating cocatalysts is 1:10,000 to 100:1.

The invention further includes a process for preparing a polyolefin, the process comprising contacting at least one polymerizable olefin with the catalyst of the previous paragraph under conditions sufficient to polymerize at least some of the at least one polymerizable olefin, thereby producing a polyolefin.

The term "polymerizable olefin" means a carbon-carbon double or triple bond-containing monomer or carbon-carbon double or triple bond-containing oligomer or polyolefin prepared therefrom and independently has from 2 to 100,000 carbon atoms, preferably 50,000 carbon atoms or less, more preferably 10,000 carbon atoms or less. Preferably there is at least one carbon-carbon double bond in the polymerizable olefin, and more preferably the polymerizable olefin is a carbon-carbon double bond-containing monomer. Thus, polymerizable olefins include long chain macromolecular alpha-olefin units that are vinyl terminated polymeric remnants formed in situ during polymerization reactions. In some aspects of the polymer-forming process, such long chain macromolecular alpha-olefin units are readily polymerized along with ethylene and other short chain olefin monomers to give a polyolefin having long chain branching.

Preferably, the polyolefin prepared by the process is an ethylene homopolymer, an ethylene/alpha-olefin interpolymer (e.g., copolymer), or an ethylene/alpha-olefin/diene interpolymer (e.g., terpolymer). In some embodiments, the polyolefin is a copolymer of ethylene and 1-octene.

In some embodiments, the polyolefin-forming process further employs another polymerizable olefin (i.e., an olefin comonomer) so as to employ both an olefin monomer and olefin comonomer, a chain shuttling agent, and an associated olefin polymerization catalyst (which may be an invention catalyst, or a non-invention catalyst described later), the preferred process giving the polyolefin wherein the polyolefin comprises a poly(olefin monomer-olefin comonomer) interpolymer (e.g., copolymer), more preferably a poly (olefin monomer-olefin comonomer) block copolymer (i.e., an OBC), and in some embodiments a poly(ethylene/alpha-olefin) block copolymer. The poly(ethylene/alpha-olefin) block copolymer preferably comprises an ethylene-derived hard segment and a soft segment comprising residuals from the alpha-olefin and ethylene. The term "poly(ethylene/alpha-olefin) block copolymer" is used interchangeably herein with the terms "olefin block copolymer," "OBC," "ethylene/α-olefin block interpolymer," and "ethylene/α-olefin block copolymer". The terms "alpha-olefin" and "α-olefin" are used interchangeably herein.

Preferably, the polyolefin-forming process employs a solvent. The term "solvent" means a liquid, preferably aprotic, that is compatible with the polyolefin-forming process. Suitable solvents include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; benzene and $(C_1-C_5)$alkyl-substituted benzenes such as toluene and xylenes; $(C_1-C_5)$alkyl-O—$(C_1-C_5)$alkyl; $(C_4-C_5)$heterocycloalkyl such as tetrahydrofuran, tetrahydropyran, and 1,4-dioxane; $(C_1-C_5)$alkyl ethers of (poly) alkylene glycols; and mixtures of the foregoing. In these embodiments, the catalyst preferably comprises a homogeneous catalyst.

In some embodiments, the catalyst further comprises, or is further prepared from, an inorganic or organic particulated solid support, wherein the catalyst is in supporting operative contact with the particulated solid support to give a particulated solid-supported catalyst. In these embodiments, the invention particulated solid-supported catalyst comprises a heterogeneous catalyst.

The particulated solid support is any material that is capable of supporting the catalyst and allows the resulting invention particulated solid-supported catalyst to catalyze polymerization of a polymerizable olefin. Examples of particulated solids are silica, alumina, clays, expanded clays (aerogels), aluminosilicates, trialkylaluminum compounds, and organic or inorganic polymeric materials, especially polyolefins such as, for example, a poly(tetrafluoroethylene). More preferably, the catalyst and solid support are employed in the invention particulated solid-supported catalyst in amounts that provide a ratio of (weight of the catalyst based on metal M):(weight of the solid support) of from $1:10^6$ to $1:10^3$, more preferably from $1:10^6$ to $1:10^4$.

The metal-ligand complexes of formula (I) are rendered catalytically active by contacting them to, or combining them with, an activating cocatalyst or by using an activating technique such as those that are known in the art for use with metal (e.g., Group 4) olefin polymerization reactions. The present invention contemplates replacing one or more of the activating cocatalysts with the activating technique, although use of activating cocatalysts is preferred. Suitable activating cocatalysts for use herein include alkyl aluminums; polymeric or oligomeric alumoxanes (also known as aluminoxanes); neutral Lewis acids; and non-polymeric, non-coordinating, ion-forming compounds (including the use of such compounds under oxidizing conditions). A suitable activating technique is bulk electrolysis. Combinations of one or more of the foregoing activating cocatalysts and techniques are also contemplated. The term "alkyl aluminum" means a monoalkyl aluminum dihydride or monoalkylaluminum dihalide, a dialkyl aluminum hydride or dialkyl aluminum halide, or a trialkylaluminum. Aluminoxanes and their preparations are known at, for example, U.S. Pat. No. 6,103,657. Examples of preferred polymeric or oligomeric alumoxanes are methylalumoxane, triisobutyl-aluminum-modified methylalumoxane, and isobutylalumoxane.

Preferred Lewis acid activating cocatalysts are Group 13 metal compounds containing from 1 to 3 hydrocarbyl substituents as described herein. More preferred Group 13 metal compounds are tri(hydrocarbyl)-substituted-aluminum or tri(hydrocarbyl)-boron compounds, still more preferred are tri(($C_1$-$C_{10}$)alkyl)aluminum or tri(($C_6$-$C_{18}$)aryl)boron compounds and halogenated (including perhalogenated) derivatives thereof, even more especially tris(fluoro-substituted phenyl)boranes, still even more especially tris(pentafluorophenyl)borane.

Preferred combinations of neutral Lewis acid activating cocatalysts include mixtures comprising a combination of a tri(($C_1$-$C_4$)alkyl)aluminum and a halogenated tri(($C_6$-$C_{18}$)aryl)boron compound, especially a tris(pentafluorophenyl)borane. Also preferred are combinations of such neutral Lewis acid mixtures with a polymeric or oligomeric alumoxane, and combinations of a single neutral Lewis acid, especially tris(pentafluorophenyl)borane with a polymeric or oligomeric alumoxane. Preferred ratios of numbers of moles of (metal-ligand complex):(tris(pentafluorophenyl) borane):(alumoxane) [e.g., (Group 4 metal-ligand complex): (tris(pentafluorophenyl)borane):(alumoxane)] are from 1:1:1 to 1:10:30, more preferably from 1:1:1.5 to 1:5:10.

Many activating cocatalysts and activating techniques have been previously taught with respect to different metal-ligand complexes in the following U.S. Pat. Nos. 5,064,802; 5,153,157; 5,296,433; 5,321,106; 5,350,723; 5,425,872; 5,625,087; 5,721,185; 5,783,512; 5,883,204; 5,919,983; 6,696,379; and 7,163,907. Examples of suitable hydrocarbyloxides are disclosed in U.S. Pat. No. 5,296,433. Examples of suitable Bronsted acid salts for addition to polymerization catalysts are disclosed in U.S. Pat. Nos. 5,064,802; 5,919,983; 5,783,512. Examples of suitable salts of a cationic oxidizing agent and a non-coordinating, compatible anion as activating cocatalysts for addition polymerization catalysts are disclosed in U.S. Pat. No. 5,321,106. Examples of suitable carbenium salts as activating cocatalysts for addition polymerization catalysts are disclosed in U.S. Pat. No. 5,350,723. Examples of suitable silylium salts as activating cocatalysts for addition polymerization catalysts are disclosed in U.S. Pat. No. 5,625,087. Examples of suitable complexes of alcohols, mercaptans, silanols, and oximes with tris(pentafluorophenyl)borane are disclosed in U.S. Pat. No. 5,296,433. Some of these catalysts are also described in U.S. Pat. No. 6,515,155 B1.

In some embodiments, one or more of the foregoing activating cocatalysts are used in combination with each other. An especially preferred combination is a mixture of a tri(($C_1$-$C_4$)hydrocarbyl)aluminum, tri(($C_1$-$C_4$)hydrocarbyl) borane, or an ammonium borate with an oligomeric or polymeric alumoxane compound.

The ratio of total number of moles of one or more metal-ligand complexes of formula (I) to total number of moles of one or more activating cocatalyst is from 1:10,000 to 100:1. Preferably, the ratio is at least 1:5000, more preferably at least 1:1000; and 10:1 or less, more preferably 1:1 or less. When an alumoxane alone is used as an activating cocatalyst, preferably the number of moles of the alumoxane that are employed is at least 5 times the number of moles of the metal-ligand complex of formula (I). When tris(pentafluorophenyl)borane alone is used as an activating cocatalyst, preferably the ratio of the number of moles of the tris(pentafluorophenyl)borane that are employed to the total number of moles of one or more metal-ligand complexes of formula (I) is 0.5:1 to 10:1, more preferably from 1:1 to 6:1, still more preferably from 1:1 to 5:1. The remaining activating cocatalysts are generally employed in approximately mole quantities equal to the total mole quantities of one or more metal-ligand complexes of formula (I).

In some embodiments, a reducing agent is also employed so as to produce lower oxidation state forms (e.g., +2) of the metal-ligand complexes of formula (I) from higher oxidation state forms (e.g., +4) of the metal-ligand complexes of formula (I). As used herein, the term "reducing agent" means a metal-containing substance or compound, organic reductant, or technique (e.g., electrolysis) which, under reducing conditions, causes the metal, M, to be reduced from a higher to a lower oxidation state (e.g., from a +6 formal oxidation state to a +4 formal oxidation state). Examples of suitable reducing agents are alkali metals, alkaline earth metals, aluminum and zinc, and alloys of alkali metals or alkaline earth metals such as sodium/mercury amalgam and sodium/potassium alloy. Examples of other suitable reducing agents are sodium naphthalenide, potassium graphite, lithium alkyls, lithium or potassium alkadienyls, and Grignard reagents (e.g., alkyl magnesium halides). Most preferred reducing agents are the alkali metals or alkaline earth metals, especially lithium and magnesium metal. Suitable techniques that may be adapted by an ordinarily skilled artisan for preparing the metal-ligand complexes of the present invention are known and preferably are derived from techniques taught, for example, in U.S. Pat. Nos. 5,866,704; 5,959,047; and 6,268,444.

The term "olefin-polymerizing conditions" means reaction parameters such as, for example, temperature, pressure, concentration of olefin monomer(s), solvent(s), if any, reaction time, and reaction atmosphere sufficient to produce at least 5 mole percent yield of a polyolefin. In some embodiments, polymerization of olefins is accomplished using known conditions for Ziegler-Natta or Kaminsky-Sinn type olefin polymerization reactions. The process occurs under olefin-polymerizing conditions sufficient to polymerize at least some of the at least one polymerizable olefin and produce a polyolefin therefrom. The process can be performed at or with any temperature, pressure, or other condition (e.g., solvent, atmosphere, and absolute and relative amounts of ingredients) at which the polymerization reaction occurs. Preferably the conditions comprise a temperature of about −100° C. to about 300° C. Within this range, the temperature is preferably at least about 0° C., more preferably at least about 20° C., still more preferably at least about 50° C. Also within this range, the temperature is preferably about 250° C. or less, more preferably about 200° C. or less, still more preferably about 150° C. or less. Preferably the conditions include a pressure of about 0.5 atmosphere (50 kilopascals (kPa)) to 10,000 atmospheres (1,010,000 kPa). Within this range, the pressure is preferably at least about 1 atmosphere (101 kPa), more preferably at least about 10 atmospheres (1010 kPa). Also within this range, the pressure is preferably 1000 atmospheres (101,000 kPa) or less, more preferably 500 atmospheres (50,500 kPa) or less. The conditions preferably include a substantially inert atmosphere (e.g., a dry (i.e., substantially free from water) atmosphere consisting essentially of nitrogen gas, a noble gas (e.g., argon gas and helium gas), or a mixture of two or more thereof), with mixing (e.g., agitating, stirring, or shaking) for a time sufficient to produce the polyolefin (e.g., as determined by assaying an aliquot of a reaction mixture).

In some embodiments, the polymer-forming process employs one or more of the inventive catalysts and at least one additional homogeneous or heterogeneous polymerization catalyst, which may be a same or different inventive catalyst or a prior art olefin polymerization catalyst such as that referenced previously, either in the same reactor or in separate reactors, preferably connected in series or in parallel, to prepare polymer blends having desirable properties. A general description of such a process is disclosed in PCT International Patent Application Publication Number WO 94/00500.

Polyolefins prepared by the process are useful, among other things, as synthetic lubricants (synthetic motor oils) and as materials for use in manufacturing foams, films, coatings, fibers, fabrics, extruded articles, and molded articles.

EXAMPLES

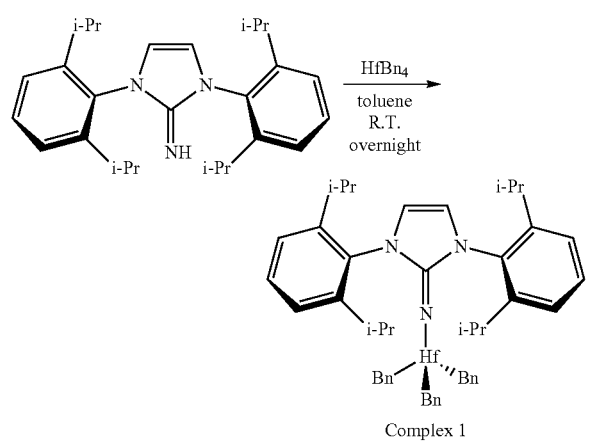

Complex 1

Preparation of Complex 1. In a glovebox under a nitrogen atmosphere, a glass jar was charged with a magnetic stirbar, HfBn$_4$ (0.600 g, 1.11 mmol) and toluene (10 mL). The resulting solution was cooled to −40° C., and then 1,3-bis (2,6-diisopropylphenyl)-1H-imidazol-2(3H)-imine (0.446 g, 1.11 mmol) was added to the cold solution. The resulting solution was allowed warm to room temperature, and stirred overnight. The solvent volume was reduced to about 5 mL. Hexane (5 mL) was then added to the solution, which was cooled to −40° C. After 1 day, crystals were collected and dried, providing the desired species in high purity (0.91 g, 97%). $^1$H NMR (400 MHz, C$_6$D$_6$) δ 7.25 (dd, J=8.5, 6.9 Hz, 2H), 7.18-7.12 (m, 4H), 7.06 (t, J=7.6 Hz, 6H), 6.89 (m, 3H), 6.38 (dd, J=7.6, 1.3 Hz, 6H), 5.95 (s, 2H), 3.13 (sp, J=6.9 Hz, 4H), 1.40 (d, J=6.9 Hz, 12H), 1.21 (s, 6H), 1.15 (d, J=6.9 Hz, 12H).

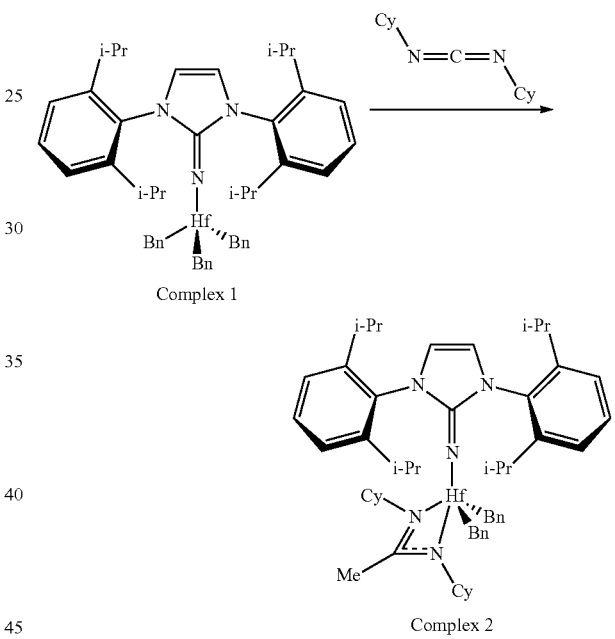

Complex 1

Complex 2

Preparation of Complex 2. Complex 1 (0.500 g, 0.585 mmol) and N,N'-dicyclohexylcarbodiimide (0.121 g, 0.585 mmol) were combined in a small vial. Toluene (10 mL) was added and the reaction was allowed to stir overnight. The reaction mixture was concentrated and hexane was added until approximately a 1:2 ratio (toluene:hexane) was reached and the vial was placed in the freezer to induce crystallization. The resulting off white solid was isolated by filtration yielding the desired compound (0.148 g, 22%). $^1$H NMR (400 MHz, C$_6$D$_6$) δ 7.27-7.19 (m, 6H), 7.17-7.15 (m, 6H), 7.14-7.07 (m, 2H), 7.07-6.97 (m, 5H), 6.90 (tt, J=7.3, 1.3 Hz, 2H), 5.96 (s, 2H), 3.52 (s, 2H), 3.31 (p, J=6.8 Hz, 4H), 2.81 (td, J=10.8, 5.3 Hz, 2H), 2.26 (d, J=10.8 Hz, 2H), 1.88 (d, J=10.8 Hz, 2H), 1.54-1.46 (m, 4H), 1.43 (d, J=6.8 Hz, 12H), 1.30-1.21 (m, 2H), 1.18 (d, J=6.8 Hz, 12H), 1.11-0.82 (m, 14H).

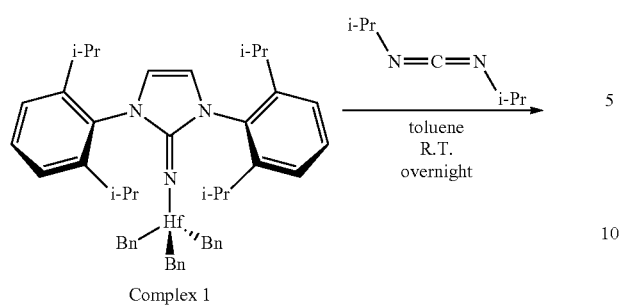
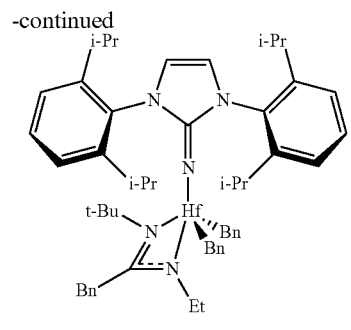

Complex 1 → Complex 4

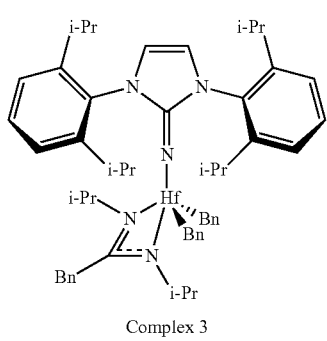

Complex 3

Preparation of Complex 3. In a glovebox under a nitrogen atmosphere, a glass jar was charged with a magnetic stirbar, complex 1 (0.505 g, 0.591 mmol) and toluene (10 mL). The resulting solution was cooled to −40° C., and then 1,3-diisopropyl-carbodiimide (0.097 mL, 0.621 mmol) was added to the cold solution. The resulting solution was stirred and allowed warm to room temperature. After 1 h the solvent volume was reduced to about 5 mL. Hexane (5 mL) was then added to the solution, which was cooled to −40° C. After 1 day, yellow crystals were collected and dried, providing the desired species in high purity (0.47 g, 81%). $^1$H NMR (400 MHz, $C_6D_6$) δ 7.27-7.11 (m, 13H), 7.07 (dd, J=8.2, 1.4 Hz, 4H), 6.95-6.83 (m, 4H), 6.06 (s, 2H), 3.38 (sp, J=6.8 Hz, 4H), 3.35 (s, 2H), 3.32 (sp, J=6.5 Hz, 2H), 1.91 (d, J=11.4 Hz, 2H), 1.64 (d, J=11.4 Hz, 2H), 1.38 (d, J=6.8 Hz, 12H), 1.18 (d, J=6.8 Hz, 12H), 0.70 (d, J=6.5 Hz, 12H). $^{13}$C NMR (101 MHz, $C_6D_6$) δ 176.04, 149.53, 147.49, 145.49, 135.93, 134.63, 129.79, 128.91, 128.47, 128.13, 126.66, 124.39, 120.70, 114.69, 73.67, 47.76, 32.60, 29.06, 25.42, 24.76, 23.37.

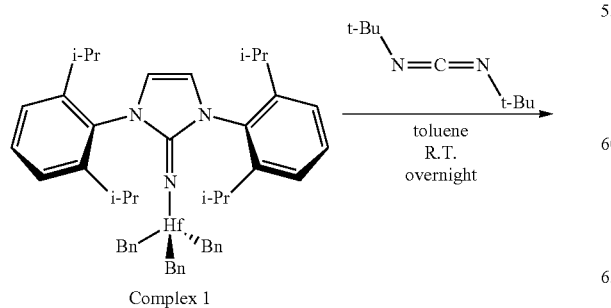

Complex 1

Preparation of Complex 4. In a glovebox under a nitrogen atmosphere, a glass jar was charged with a magnetic stirbar, complex 1 (0.250 g, 0.293 mmol) and toluene (10 mL). The resulting solution was cooled to −40° C., and then 1-tert-Butyl-3-ethylcarbodiimide (0.048 mL, 0.307 mmol) was added to the cold solution. The resulting solution was stirred and allowed warm to room temperature. After 1 h the solvent volume was reduced to about 5 mL. Hexane (5 mL) was then added to the solution, which was cooled to −40° C. After 1 day, off white colored crystals were collected and dried, providing the desired species in high purity (0.254 g, 89%). $^1$H NMR (400 MHz, $C_6D_6$) δ 7.30-7.06 (m, 13H), 7.02 (dd, J=8.1, 1.3 Hz, 2H), 6.87-6.77 (m, 6H), 5.97 (s, 2H), 3.47 (s, 2H), 3.25 (sp, J=6.8 Hz, 4H), 3.06 (q, J=7.0 Hz, 2H), 1.74 (d, J=11.5 Hz, 2H), 1.53 (d, J=11.5 Hz, 2H), 1.45 (d, J=6.8 Hz, 12H), 1.20 (d, J=6.8 Hz, 12H), 0.70 (t, J=7.0 Hz, 3H), 0.67 (s, 9H).

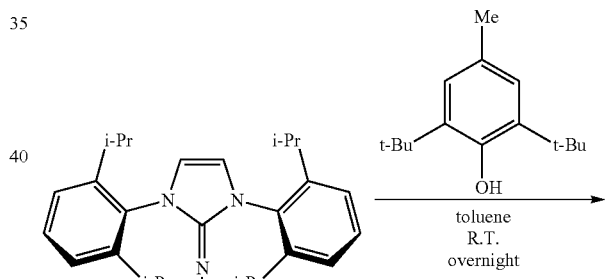
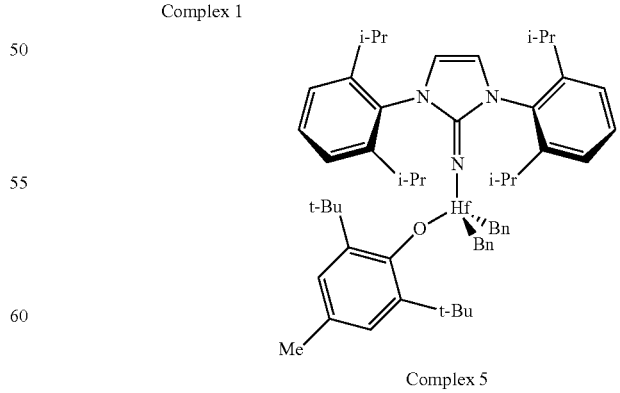

Preparation of Complex 5. In a glovebox under a nitrogen atmosphere, a glass jar was charged with a magnetic stirbar, complex 1 (0.250 g, 0.293 mmol) and toluene (10 mL). The resulting solution was cooled to −40° C., and then 2,6-di-tert-butyl-4-methylphenol (0.068 g, 0.307 mmol) was added to the cold solution. The resulting solution was stirred and allowed warm to room temperature. After 1 h the solvent volume was reduced to about 5 mL. Hexane (5 mL) was then added to the solution, which was cooled to −40° C. After 1 day, off-white colored crystals were collected and dried, providing the desired species in high purity (0.186 g, 65%). $^1$H NMR (400 MHz, C$_6$D$_6$) δ 7.21 (dd, J=8.4, 7.1 Hz, 2H), 7.18-7.08 (m, 8H), 7.05 (s, 2H), 6.87-6.76 (m, 6H), 5.82 (s, 2H), 3.03 (sp, J=6.9 Hz, 4H), 2.28 (s, 3H), 2.15 (d, J=12.1 Hz, 2H), 1.85 (d, J=12.1 Hz, 2H), 1.24 (s, 12H), 1.24 (d, J=6.9 Hz, 12H), 1.09 (d, J=6.9 Hz, 12H).

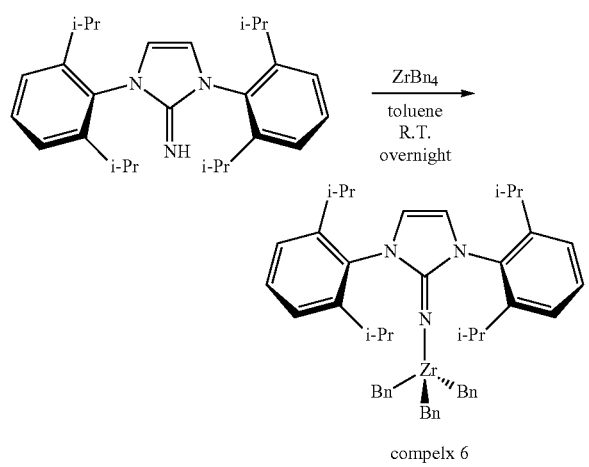

compelx 6

Preparation of Complex 6. To a vial containing 1,3-bis(2,6-diisopropylphenyl)-1H-imidazol-2(3H)-imine (0.172 g, 0.43 mmol) and ZrBn$_4$ (0.1942 g, 0.43 mmol) was added 2 mL of C$_6$D$_6$ which dissolved the components resulting in yellow-orange solution. Reaction mixture was stirred for 4 hr. To the reaction mixture was added 8 mL of hexane, solution was filtered through syringe filter and filtrate was put into freezer (−20° C.). Within minutes crystals appeared. After 24 hr in the freezer solution was decanted and yellow crystals were washed with hexane (2×3 mL) and dried under reduced pressure to give 0.268 mg of product. Yield 82%. $^1$H NMR (500 MHz, C$_6$D$_6$) δ 7.24 (dd, J=8.4, 7.1 Hz, 2H), 7.16 (d, J=7.3 Hz, 4H), 7.06-6.98 (m, 6H), 6.91-6.83 (m, 2H), 6.33-6.22 (m, 6H), 5.92 (s, 2H), 3.14 (hept, J=6.9 Hz, 4H), 1.41 (d, J=6.9 Hz, 12H), 1.35 (s, 6H), 1.15 (d, J=6.9 Hz, 12H). $^{13}$C NMR (126 MHz, C$_6$D$_6$) δ 147.38, 142.98, 142.55, 134.05, 130.18, 130.02, 127.27, 124.41, 121.92, 114.36, 60.28, 29.16, 24.46, 23.60.

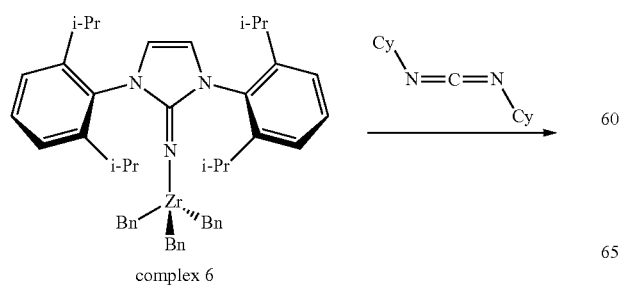

complex 6

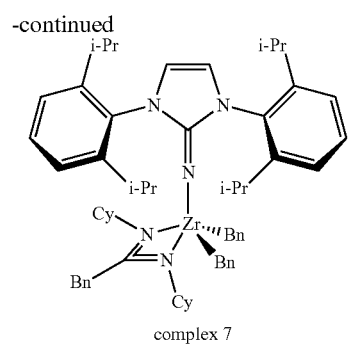

complex 7

Preparation of Complex 7. Complex 6 (0.500 g, 0.652 mmol) and N,N'-dicyclohexylcarbodiimide (0.134 g, 0.652 mmol) were combined in a small vial. Toluene (10 mL) was added and the reaction was allowed to stir overnight. The reaction mixture was concentrated and hexane was added until approximately a 1:2 ratio (toluene:hexane) was reached and the vial was placed in the freezer to induce crystallization. The resulting off white solid was isolated by filtration yielding the desired compound (0.444 g, 70%). $^1$H NMR (400 MHz, C$_6$D$_6$) δ 7.27-7.19 (m, 7H), 7.17 (s, 2H), 7.14-7.07 (m, 2H), 7.07-6.97 (m, 6H), 6.90 (tt, J=7.3, 1.3 Hz, 2H), 5.96 (s, 2H), 3.52 (s, 2H), 3.31 (p, J=6.8 Hz, 4H), 2.81 (td, J=10.8, 5.3 Hz, 2H), 2.26 (d, J=10.8 Hz, 2H), 1.88 (d, J=10.8 Hz, 2H), 1.54-1.46 (m, 5H), 1.43 (d, J=6.8 Hz, 15H), 1.30-1.21 (m, 2H), 1.18 (d, J=6.8 Hz, 12H), 1.11-0.82 (m, 14H).

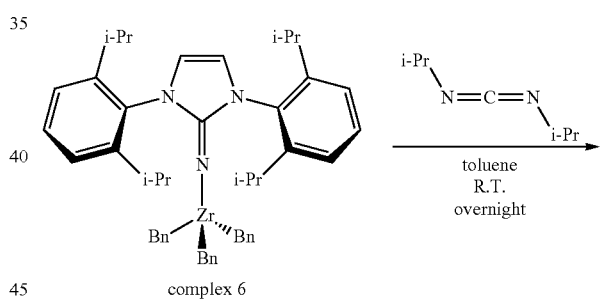

complex 6

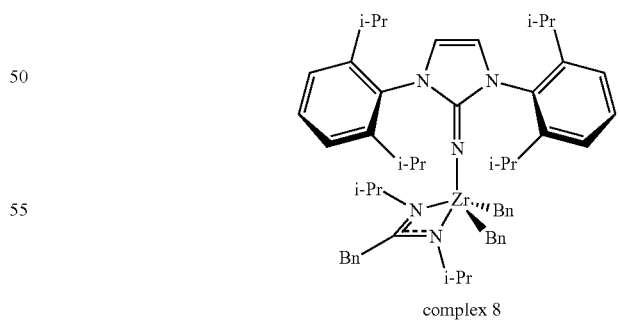

complex 8

Preparation of Complex 8. In a glovebox under a nitrogen atmosphere, a glass jar was charged with a magnetic stirbar, complex 6 (0.525 g, 0.684 mmol) and toluene (10 mL). The resulting solution was cooled to −40° C., and then 1,3-diisopropyl-carbodiimide (0.107 mL, 0.684 mmol) was added to the cold solution. The resulting solution was stirred and allowed warm to room temperature. After 1 h the solvent volume was reduced to about 5 mL. Hexane (5 mL) was then added to the solution, which was cooled to −40° C. After 1 day, yellow crystals were collected and dried, providing the desired species in high purity (0.45 g, 73%). $^1$H NMR (400 MHz, $C_6D_6$) δ 7.40-7.11 (m, 13H), 7.08-7.02 (m, 4H), 6.94-6.82 (m, 4H), 6.04 (s, 2H), 3.39 (sp, J=6.8 Hz, 4H), 3.36 (s, 2H), 3.19 (sp, J=6.4 Hz, 2H), 2.23 (d, J=10.5 Hz, 2H), 1.87 (d, J=10.5 Hz, 2H), 1.39 (d, J=6.8 Hz, 12H), 1.17 (d, J=6.8 Hz, 12H), 0.72 (d, J=6.4 Hz, 12H). $^{13}$C NMR (101 MHz, $C_6D_6$) δ 176.24, 149.04, 147.42, 141.94, 136.25, 134.57, 129.87, 128.88, 128.47, 128.39, 127.38, 126.59, 124.44, 120.44, 114.80, 65.83, 47.92, 32.23, 29.10, 25.47, 24.90, 23.38.

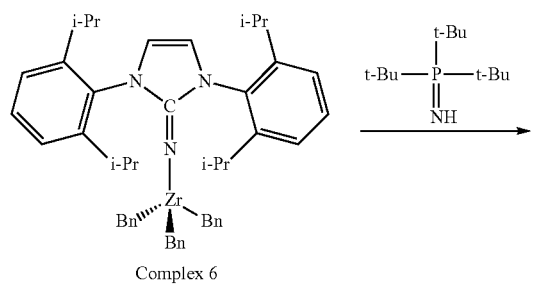

Complex 6

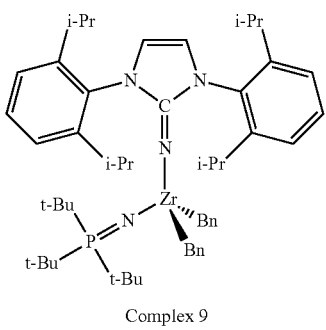

Complex 9

Preparation of Complex 9. To a vial containing 85 milligrams (mg) (0.11 mmol) of complex 6 and 24.1 mg (0.11 mmol) of t-Bu$_3$P=NH was added 1 mL of $C_6D_6$. Resulting yellow solution change color to virtually colorless within a few seconds. NMR taken after 10 min shows formation of the desired complex. Most of the solvent was removed under reduced pressure. To the residue (~100 microliters (μl)) was added 2 mL of hexane. Within seconds white crystals started to form. After 30 min solvent was decanted and remaining crystals were washed with 3 mL of hexane and then dried under reduced pressure to give 28 mg. The filtrate was put into freezer overnight. Solvent was decanted and formed crystals were washed with 2 mL of cold hexane and dried under reduced pressure to give 27 mg of product. Combined yield 55 mg, 55.6%. $^1$H NMR (500 MHz, $C_6D_6$) δ 7.26-7.21 (m, 2H), 7.21-7.17 (m, 4H), 7.13 (t, J=7.7 Hz, 4H), 6.85-6.78 (m, 6H), 5.97 (s, 2H), 3.31 (hept, J=6.8 Hz, 4H), 2.10 (d, J=10.1 Hz, 2H), 1.54 (d, J=10.1 Hz, 2H), 1.47 (d, J=6.9 Hz, 12H), 1.22 (d, J=6.9 Hz, 12H), 0.94 (d, J=12.6 Hz, 27H).

$^{13}$C NMR (126 MHz, $C_6D_6$) δ 149.67, 147.62, 135.33, 129.53, 128.53, 126.62, 124.29, 119.89, 114.04, 57.73, 39.60 (d, J=47.1 Hz), 29.70, 29.06, 24.43, 24.01. $^{31}$P NMR (202 MHz, $C_6D_6$) δ 32.27.

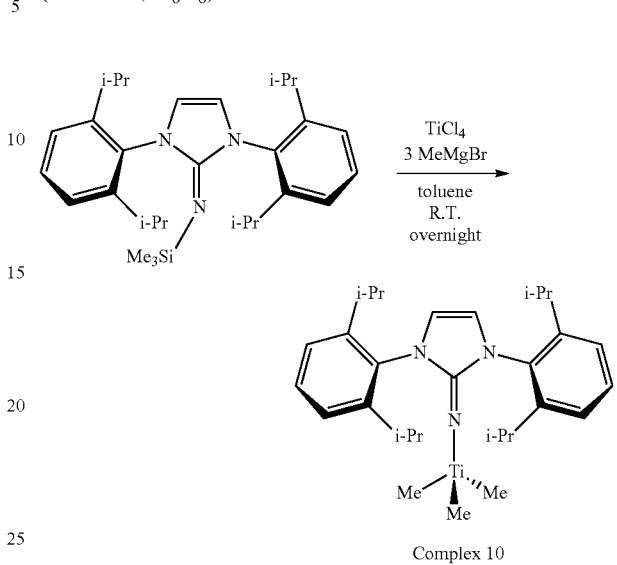

Complex 10

Preparation of Complex 10. In a glovebox under a nitrogen atmosphere, a solution of TiCl$_4$ (0.231 mL, 2.10 mmol) in toluene (10 mL) was treated with a solution of N-(1,3-bis(2,6-diisopropylphenyl)-1H-imidazol-2(3H)-ylidene)-1,1,1-trimethylsilanamine (1.00 g, 2.10 mmol) in toluene (5 mL). A dark orange precipitate formed immediately, and the resulting suspension was stirred for 0.5 h, at which point MeMgBr (4.20 mL of a 3M solution in diethyl ether, 6.73 mmol) was added and the reaction mixture was stirred overnight at ambient temperature. The volatiles were removed under vacuum, and the resulting brown residue was extracted with hexane (40 mL) and filtered. The filtrate was collected, concentrated to about 15 mL, and cooled to −40° C. After 1 day, yellow/brown crystals were collected and dried, providing the desired species in high purity (0.94 g, 90%). $^1$H NMR (500 MHz, $C_6D_6$) δ 7.20 (dd, J=8.4, 7.1 Hz, 2H), 7.11 (d, J=7.4 Hz, 4H), 5.91 (s, 2H), 3.11 (sp, J=6.9 Hz, 4H), 1.40 (d, J=6.9 Hz, 12H), 1.16 (d, J=6.9 Hz, 12H), 0.72 (s, 9H). $^{13}$C NMR (101 MHz, $C_6D_6$) δ 147.31, 140.62, 133.46, 130.21, 124.13, 113.80, 53.14, 29.22, 24.20, 23.76.

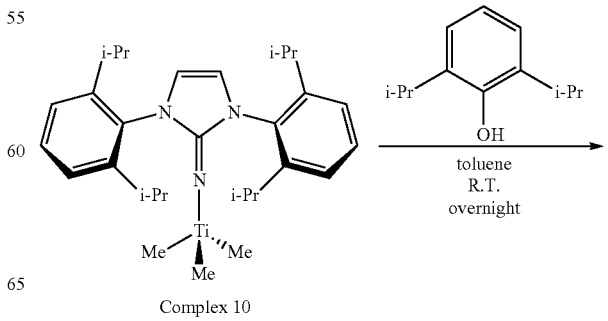

Complex 10

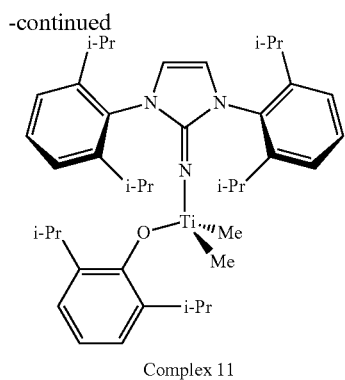

Complex 11

Preparation of Complex 11. In a glovebox under a nitrogen atmosphere, a glass jar was charged with a magnetic stirbar, complex 10 (0.200 gram (g), 0.404 millimole (mmol)) and toluene (5 milliliters (mL)). The resulting solution was stirred at ambient temperature, and then 2,6-diisopropylphenol (0.075 mL, 0.404 mmol) was added. The resulting solution was allowed to stir for 3 hours (h). The solvent volume was reduced to about 2 mL, and hexane (about 3 mL) was added and the mixture was cooled to −40° C. After 1 day, pale yellow crystals were collected, providing the desired species in high purity (0.130 g, 49%). $^1$H NMR (400 MHz, $C_6D_6$) δ 7.20 (dd, J=8.1, 7.1 Hz, 2H), 7.14 (d, J=7.6 Hz, 2H), 7.06 (d, J=7.6 Hz, 4H), 7.00 (dd, J=8.1, 7.1 Hz, 1H), 5.77 (s, 2H), 3.29 (sp, J=6.9 Hz, 2H), 3.04 (sp, J=6.9 Hz, 4H), 1.31 (d, J=6.9 Hz, 12H), 1.18 (d, J=6.9 Hz, 12H), 1.11 (d, J=6.9 Hz, 12H), 0.68 (s, 6H).

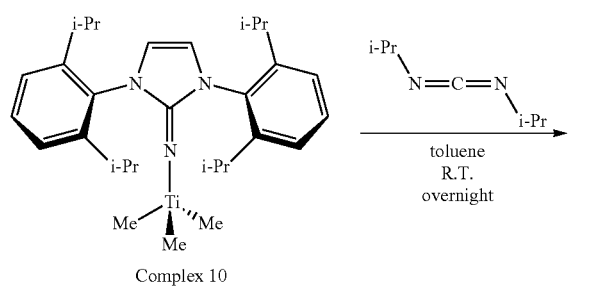

Complex 10

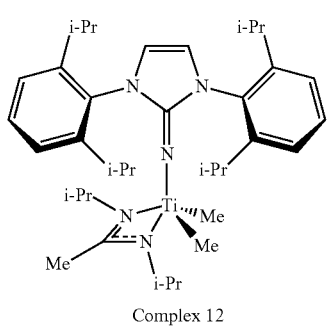

Complex 12

Preparation of Complex 12. In a glovebox under a nitrogen atmosphere, a glass jar was charged with a magnetic stirbar, complex 10 (0.045 g, 0.091 mmol) and toluene (2 mL). The resulting solution was stirred at ambient temperature, and then 1,3-diisopropyl-carbodiimide (0.017 mL, 0.109 mmol) was added. The resulting solution was allowed to stir for 0.5 h, at which point volatiles were removed under vacuum, affording desired species in high purity (0.056 g, 100%). $^1$H NMR (400 MHz, $C_6D_6$) δ 7.23 (dd, J=8.6, 6.7 Hz, 2H), 7.15 (d, J=7.0 Hz, 4H), 5.90 (d, J=0.6 Hz, 2H), 3.34 (sp, J=6.8 Hz, 4H), 3.28 (sp, J=6.4 Hz, 2H), 1.58 (s, 1H), 1.44 (d, J=6.8 Hz, 12H), 1.19 (d, J=6.8 Hz, 12H), 0.91 (d, J=6.4 Hz, 12H), 0.69 (s, 6H). $^{13}$C NMR (101 MHz, $C_6D_6$) δ 173.52, 147.47, 138.75, 134.65, 129.89, 124.19, 114.30, 54.84, 48.08, 29.09, 24.77, 24.60, 23.70, 10.35.

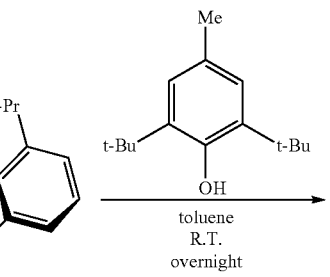

Complex 10

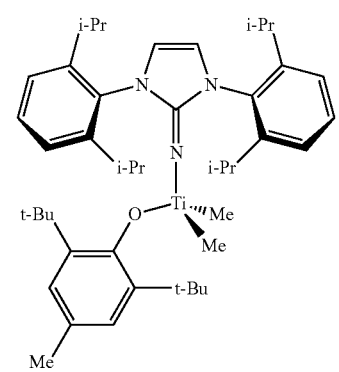

Complex 13

Preparation of Complex 13. In a glovebox under a nitrogen atmosphere, a glass jar was charged with a magnetic stirbar, complex 10 (0.030 g, 0.061 mmol) and toluene (5 mL). The resulting solution was stirred at ambient temperature, and then 2,6-di-tert-butyl-4-methylphenol (0.013 g, 0.061 mmol) was added. The resulting solution was allowed to stir for 0.5 h. The volatiles were removed under vacuum, and the residue was taken up in the minimal amount of hexane (ca. 1 mL). This solution was cooled to −40° C. After 1 day, pale yellow crystals were collected, providing the desired species in high purity (0.021 g, 50%). $^1$H NMR (400 MHz, $C_6D_6$) δ 7.21 (dd, J=8.3, 7.2 Hz, 2H), 7.14 (s, 2H), 7.07 (d, J=7.7 Hz, 4H), 5.76 (s, 2H), 3.12 (p, J=6.9 Hz, 4H), 2.30 (s, 3H), 1.39 (s, 18H), 1.27 (d, J=6.9 Hz, 12H), 1.09 (d, J=6.9 Hz, 12H), 0.83 (s, 6H).

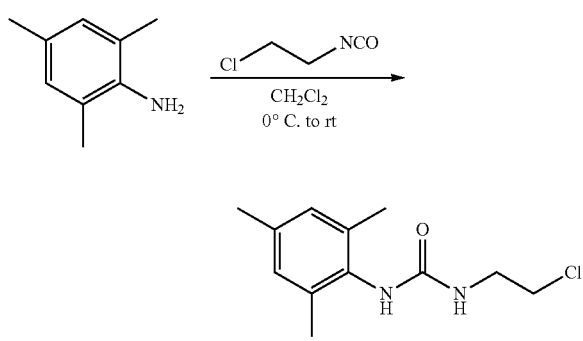

Preparation of 1-(2-chloroethyl)-3-mesitylurea. To a 500 mL round-bottom flask equipped with a magnetic stirbar was added dichloromethane (150 mL) and 2,4,6-trimethylaniline (10 mL, 71.2 mmol, 1 equiv.). The vessel was cooled to 0° C. in a water/ice bath, after which 2-chloroethyl isocyanate (7.3 mL, 85.7 mmol, 1.2 equiv.) was added to the stirring solution drop-wise via syringe. The water/ice bath was removed and the reaction was allowed to warm to room temperature, stirring for a total of 20 hours. During this time, a significant amount of white solid precipitated from solution. All volatiles were removed via rotary evaporation. The solid was triturated with cold 10:1 hexanes:diethyl ether (2×100 mL). The slurry was filtered, further washed with room temperature 10:1 hexanes:diethyl ether (2×100 mL), and dried in vacuo to afford the product as a white powder (16.7 g, 97% yield) $^1$H NMR (400 MHz, DMSO-d$_6$) δ 7.48 (s, 1H), 6.81 (s, 2H), 6.17 (br s, 1H), 3.57 (t, J=6.2 Hz, 2H), 3.32 (q, J=6.3 Hz, 2H), 2.17 (s, 3H), 2.07 (s, 6H). $^{13}$C NMR (101 MHz, DMSO-d$_6$) δ 156.48, 135.93, 135.13, 133.49, 128.70, 44.84, 41.93, 20.90, 18.52. HRMS (ESI-MS+) calcd. For $C_{12}H_{17}ClN_2O$: [M+H]$^+$: 241.1102. found: 241.1105.

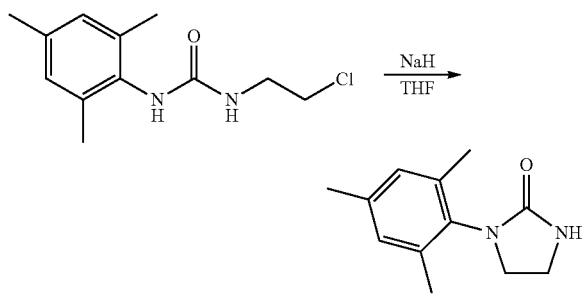

Preparation of 1-mesitylimidazolidin-2-one. In a nitrogen-filled glovebox, 1-(2-chloroethyl)-3-mesitylurea (4.81 g, 20 mmol, 1 equiv.) and tetrahydrofuran (50 mL) were added to a 250 mL round-bottom flask equipped with a magnetic stirbar. Dry sodium hydride (959 mg, 40 mmol, 2 equiv.) was added slowly to the stirring slurry, being careful to wait for hydrogen evolution to cease between additions. The sodium hydride vial was rinsed with tetrahydrofuran (5 mL), which was added to the reaction. By this point, all 1-(2-chloroethyl)-3-mesitylurea had dissolved in solution. The reaction was stirred at room temperature for 3 hours. The vessel was removed from the glove box, and water was slowly added. The solution was extracted with ethyl acetate (2×75 mL). The combined organic layers were washed with brine (1×75 mL), dried over MgSO$_4$, filtered, and concentrated via rotary evaporation to yield the product as a white solid (4.04 g, 99% yield). $^1$H NMR (400 MHz, Chloroform-d) δ 6.89 (s, 2H), 6.01 (br s, 1H), 3.71-3.62 (m, 2H), 3.60-3.53 (m, 2H), 2.25 (s, 3H), 2.23 (s, 6H). $^{13}$C NMR (101 MHz, Chloroform-d) δ 161.90, 137.60, 137.01, 132.88, 129.28, 46.41, 39.00, 20.93, 17.77. HRMS (ESI-MS+) calcd. For $C_{12}H_{16}N_2O$: [M+H]$^+$: 205.1335. found: 205.1343.

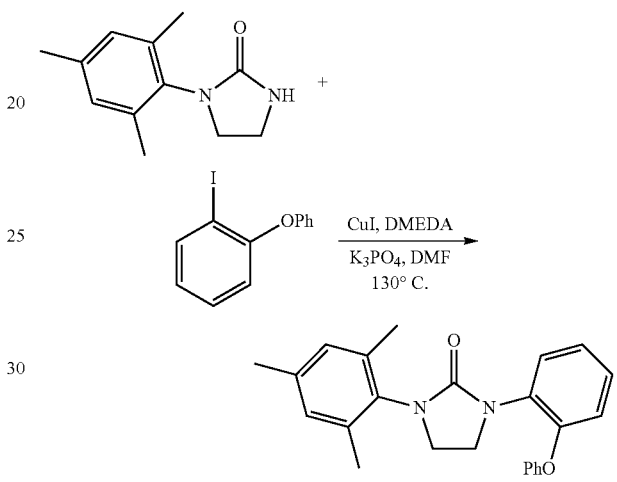

Preparation of 1-mesityl-3-(2-phenoxyphenyl)imidazolidin-2-one. To a 100 mL Schlenk flask equipped with a magnetic stirbar was added copper (I) iodide (0.520 g, 2.73 mmol, 0.3 equiv.), K$_3$PO$_4$ (3.86 g, 18.2 mmol, 2 equiv.), 1-iodo-2-phenoxybenzene (2.69 g, 9.09 mmol, 1 equiv.), and 1-mesitylimidazolidin-2-one (1.86 g, 9.09 mmol, 1 equiv.). The vessel was sealed with a septum and purged with nitrogen. Subsequently, N,N'-dimethylethylenediamine (0.59 mL, 5.46 mmol, 0.6 equiv.) and N,N-dimethylformamide (36 mL) were added via syringe. The reaction was placed into an aluminum heating block preheated to 130° C. and stirred for 18 hours. After cooling to room temperature, the material was poured onto diethyl ether (200 mL) and washed with water (2×200 mL). The combined organic layers were washed with brine (1×400 mL), dried over MgSO$_4$, and filtered. The filter cake was washed with benzene (1×50 mL). The solution was concentrated via rotary evaporation. Adsorption onto silica gel, purification via flash column chromatography (1:4 to 1:1 hexanes:ethyl acetate eluent gradient), and concentration via rotary evaporation yielded the product as a white solid (2.64 g, 78% yield). $^1$H NMR (400 MHz, Chloroform-d) δ 7.67-7.60 (m, 1H), 7.38-7.29 (m, 2H), 7.25-7.18 (m, 2H), 7.14-7.00 (m, 4H), 6.90 (s, 2H), 4.05-3.97 (m, 2H), 3.62-3.55 (m, 2H), 2.29 (s, 3H), 2.16 (s, 6H). $^{13}$C NMR (101 MHz, Chloroform-d) δ 157.32, 157.28, 151.45, 137.47, 137.03, 133.40, 131.83, 129.76, 129.23, 128.65, 127.32, 124.48, 122.97, 120.89, 117.59, 45.13, 44.14, 21.01, 17.77. HRMS (ESI-MS+) calcd. For $C_{24}H_{24}N_2O_2$: [M+H]$^+$: 373.1911. found 373.1914.

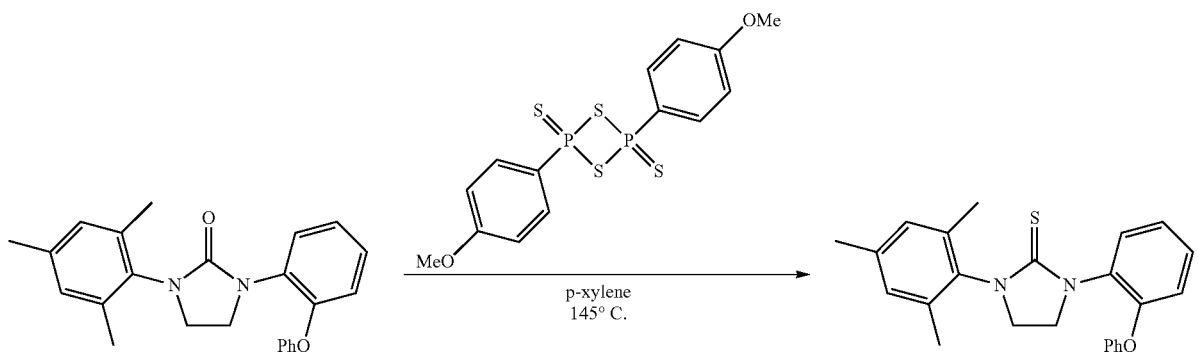 [SMILES: Cc1cc(C)c(N2CCN(c3ccccc3Oc3ccccc3)C2=O)c(C)c1 ; COc1ccc(P2(=S)SP(=S)(c3ccc(OC)cc3)S2)cc1 ; Cc1cc(C)c(N2CCN(c3ccccc3Oc3ccccc3)C2=S)c(C)c1]

Preparation of 1-mesityl-3-(2-phenoxyphenyl)imidazolidine-2-thione. To a 50 mL three-neck round-bottom flask equipped with a magnetic stirbar and a reflux condenser was added 1-mesityl-3-(2-phenoxyphenyl)imidazolidin-2-one (1.2 g, 3.22 mmol, 1 equiv.) and Lawesson's reagent (2.60 g, 6.44 mmol, 2 equiv.). The vessel was sealed with a septum. The vessel was evacuated and backfilled with nitrogen three times. P-xylene (13 mL) was added via syringe, the vessel was placed into an aluminum heating block preheated to 145° C., and stirred for 23 hours. Upon cooling to room temperature, methanol (20 mL) and 1 M aqueous HCl (5.5 mL) were added via syringe, and the biphasic mixture was stirred at room temperature for 64 hours. The mixture was poured onto toluene (20 mL) and washed with water (2×30 mL). The combined aqueous layers were extracted with toluene (2×15 mL). The combined organic layers were washed with brine (1×40 mL), dried over $MgSO_4$, and concentrated via rotary evaporation. Adsorption onto silica gel, purification via flash column chromatography (15:85 to 50:50 hexanes:ethyl acetate eluent gradient), and concentration via rotary evaporation yielded the product as a white solid (1.16 g, 92% yield). $^1H$ NMR (500 MHz, Chloroform-d) δ 7.65 (dd, J=7.8, 1.7 Hz, 1H), 7.36-7.30 (m, 3H), 7.27-7.21 (m, 1H), 7.13-7.07 (m, 3H), 7.05 (dd, J=8.2, 1.5 Hz, 1H), 6.91 (s, 2H), 4.16 (dd, J=10.2, 8.1 Hz, 2H), 3.83 (dd, J=10.2, 8.0 Hz, 2H), 2.29 (s, 3H), 2.11 (s, 6H). $^{13}C$ NMR (126 MHz, Chloroform-d) δ 182.36, 156.92, 152.79, 138.15, 136.53, 134.65, 132.29, 131.29, 129.73, 129.33, 129.15, 124.16, 123.28, 120.55, 118.09, 48.99, 47.82, 21.12, 17.65. HRMS (ESI-MS+) calcd. For $C_{24}H_{24}N_2OS$: $[M+H]^+$: 389.1682. found 389.1699.

Preparation of 2-chloro-3-mesityl-1-(2-phenoxyphenyl)-4,5-dihydro-1H-imidazol-3-ium chloride. To a 50-mL round-bottom flask equipped with a reflux condenser and a magnetic stirbar was added 1-mesityl-3-(2-phenoxyphenyl) imidazolidine-2-thione (1 g, 2.57 mmol, 1 equiv.). The vessel was evacuated and backfilled with nitrogen three times. Toluene (14 mL) and oxalyl chloride (2.1 mL, 23.2 mmol, 9 equiv.) were added via syringe. Upon addition of oxalyl chloride, the solution turned yellow. The vessel was placed into a room temperature aluminum heating block. The reaction was heated to 80° C. and stirred for 38 hours. The volatile were removed in vacuo to yield a light brown solid. The vessel was transferred to a nitrogen-filled glovebox. The solid was triturated with toluene (10 mL), filtered, and further washed with toluene (3×5 mL). Drying in vacuo afforded a white solid (0.961 g, 87% yield). $^1H$ NMR (400 MHz, Chloroform-d) 8.18 (dd, J=8.0, 1.7 Hz, 1H), 7.43-7.29 (m, 3H), 7.24-7.11 (m, 2H), 7.02-6.93 (m, 2H), 6.94-6.86 (m, 3H), 5.00 (br s, 2H), 4.67 (br s, 2H), 2.26 (br s, 3H), 2.23 (s, 6H). $^{13}C$ NMR (126 MHz, Chloroform-d) δ 157.31, 154.94, 152.12, 141.23, 135.67 (br), 132.25, 130.38, 130.30, 130.06, 129.57, 125.03, 124.88, 124.63, 118.80, 118.14, 53.33, 51.68, 21.03, 17.60 (br). HRMS (ESI-MS+) calcd. For $C_{24}H_{24}Cl_2N_2O$: $[M-Cl]^+$: 391.1572. found 391.1580.

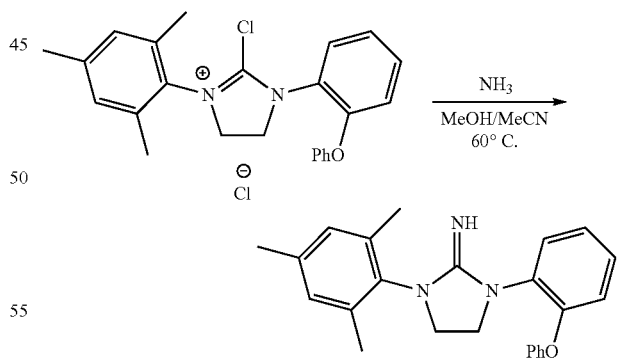

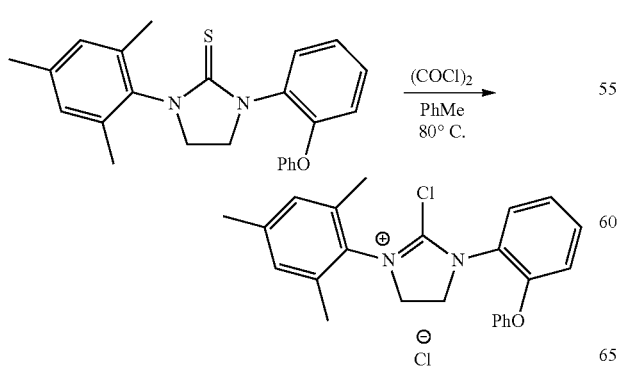

Preparation of 1-mesityl-3-(2-phenoxyphenyl)imidazolidin-2-imine. In a nitrogen-filled glovebox 2-chloro-3-mesityl-1-(2-phenoxyphenyl)-4,5-dihydro-1H-imidazol-3-ium chloride (0.9 g, 2.11 mmol, 1 equiv.) was added to a 25 mL round-bottom flask equipped with a magnetic stirbar. The vessel was sealed with a septum, removed from the glovebox, equipped with a reflux condenser, and the apparatus was evacuated and backfilled with nitrogen three times. Acetonitrile (6 mL) and 7 M ammonia in methanol (6 mL, 42 mmol, 20 equiv.) were added via syringe, and the reaction was placed in an aluminum block heated to 60° C. and stirred for 16 hours. The vessel was allowed to cool to room temperature and poured onto 30 mL water. The aqueous phase was extracted with $CH_2Cl_2$ (3×20 mL). The combined organic phases were washed with brine (1×40 mL), dried over $MgSO_4$, and concentrated via rotary evaporation to yield the product as a white solid (0.754 g, 96% yield). $^1H$ NMR (500 MHz, Chloroform-d) δ 7.32-7.25 (m, 1H), 7.14-7.04 (m, 2H), 6.90-6.85 (m, 1H), 6.83-6.77 (m, 2H), 6.77-6.72 (m, 1H), 6.69-6.64 (m, 1H), 6.60 (s, 2H), 4.60 (br s, 1H), 3.73 (t, J=7.9 Hz, 2H), 3.40 (t, J=7.9 Hz, 2H), 1.99 (s, 3H), 1.82 (s, 6H). $^{13}C$ NMR (101 MHz, Benzene-d$^6$) δ 157.54, 156.54, 152.16, 137.53, 137.43, 133.05, 132.33, 130.13, 129.60, 129.44, 127.77, 124.53, 122.64, 120.82, 117.80, 47.28, 45.87, 20.61, 17.43. HRMS (ESI-MS+) calcd. For $C_{24}H_{25}CN_3O$: $[M+H]^+$: 372.2070. found 372.2076.

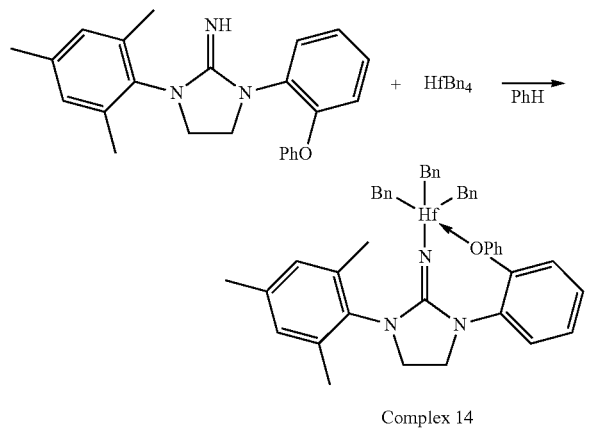

Complex 14

Preparation of Complex 14. In a nitrogen-filled glovebox, 1-mesityl-3-(2-phenoxyphenyl)imidazolidin-2-imine (40 mg, 0.108 mmol, 1 equiv.) and tetrabenzylhafnium (58.5 mg, 0.108 mol, 1 equiv.) were each separately dissolved in benzene-d$^6$ (0.7 mL) in a reaction vial equipped with a magnetic stirbar. The solution of 1-mesityl-3-(2-phenoxyphenyl)imidazolidin-2-imine was added drop-wise to the stirring solution of tetrabenzylhafnium, and the material was allowed to stir for 1.5 hours, during which time the mixture changed from yellow colored to a clear, colorless solution. All volatiles were removed in vacuo, and hexanes (5 mL) was layered onto the material, resulting in the precipitation of a white solid. All volatiles were once again removed in vacuo to yield the product as an off-white solid (45 mg, 51% yield). $^1H$ NMR (400 MHz, Benzene-d$_6$) δ 7.31 (ddd, J=7.8, 1.5, 0.6 Hz, 1H), 7.13-6.78 (m, 17H), 6.69 (s, 2H), 6.46 (dd, J=8.2, 1.2 Hz, 6H), 3.52-3.42 (m, 2H), 2.98-2.87 (m, 2H), 2.01 (s, 3H), 1.98 (s, 6H), 1.27 (s, 6H). $^{13}C$ NMR (101 MHz, Benzene-d$^6$) δ 157.70, 151.83, 149.97, 142.64, 137.65, 137.32, 134.46, 132.45, 131.08, 129.68, 129.20, 129.07, 128.05, 127.46, 124.99, 122.72, 122.15, 121.32, 117.01, 71.41, 45.44, 44.26, 20.54, 17.42.

Polymerization Procedure. A one gallon (3.79 L) stirred autoclave reactor was charged with ISOPAR™ E mixed alkanes solvent and the indicated amount of 1-octene (the total amount of ISOPAR™ E and 1-octene was 1.60 kg). The reactor was then heated to 140° C. and charged with hydrogen (if desired) followed by an amount of ethylene to bring the total pressure to ca 450 psig (2.95 MPa). The ethylene feed was passed through an additional purification column prior to entering the reactor. The catalyst composition was prepared in a drybox under inert atmosphere by mixing the desired pro-catalyst and a cocatalyst (a mixture of 1.2 equiv of $[HNMe(C_{18}H_{37})_2][B(C_6F_5)_4]$ and 50 equivalents of triisobutylaluminum modified alumoxane (MMAO-3A)) with additional solvent to give a total volume of about 17 mL. The activated catalyst mixture was then quick-injected into the reactor. The reactor pressure and temperature were kept constant by feeding ethylene during the polymerization and cooling the reactor as needed. After 10 minutes, the ethylene feed was shut off and the solution transferred into a nitrogen-purged resin kettle. The polymer was thoroughly dried in a vacuum oven, and the reactor was thoroughly rinsed with hot ISOPAR™ E between polymerization runs.

The results are summarized in the Table 1, where "Poly. (g)" is the polymer yield in grams, "Cat. Amt. (µmol)" is the catalyst amount in micromoles, "Eff. (MM g/g)" is catalyst efficiency expressed in units of millions of grams of catalyst per gram of metal in the catalyst, "Octene (g)" is the quantity of 1-octene co-monomer in grams, "$H_2$ (mmol)" is the quantity of dihydrogen in millimoles, "$T_M$ (° C.)" is the polymer melting temperature in degrees centigrade, as measured by differential scanning calorimetry, "Dens. (g/cc)" is the polymer density in grams per cubic centimeter, "Mn (g/mol)" is the number average molecular weight in grams per mole, "MWD" is the molecular weight dispersity (ratio of weight average molecular weight to number average molecular weight), and "Mw (g/mol)" is the weight average molecular weight in grams per mole. The results show that new catalysts compositions are capable of polymerizing olefins at high efficiency at industrially relevant reactor temperatures for solution process giving polyolefins with high molecular weight. Depending on particular substitution pattern polyolefin properties such as molecular weight and polydispersity (Mw/Mn) can be altered which is needed feature for commercial applications.

TABLE 1

| Metal Complex | Poly. (g) | Cat. Amt. (µmol) | Eff. (MM g/g) | Octene (g) | $H_2$ (mmol) | $T_M$ (° C.) | Dens. (g/cc) | Mn (g/mol) | MWD | Mw (g/mol) |
|---|---|---|---|---|---|---|---|---|---|---|
| 2 | 5.2 | 0.375 | 0.08 | 250 | 20 | 127.1 | 0.9233 | 83,085 | 2.44 | 202,894 |
| 2 | 4.0 | 0.31 | 0.07 | 250 | 40 | 116.4 | 0.9288 | 49,502 | 2.52 | 124,795 |
| 2 | 42.0 | 2.5 | 0.09 | 250 | 40 | 126.3 | 0.9262 | 48,405 | 2.44 | 117,842 |
| 2 | 54.4 | 2.5 | 0.12 | 250 | 0 | 124.3 | 0.9168 | 102,152 | 2.68 | 273,842 |
| 2 | 51.2 | 2.5 | 0.11 | 350 | 40 | 122.7 | 0.9243 | 44,581 | 2.63 | 117,322 |
| 2 | 54.7 | 2.5 | 0.12 | 450 | 40 | 121.5 | 0.9266 | 42,672 | 2.57 | 109,594 |
| 7 | 8.0 | 0.31 | 0.28 | 250 | 20 | 124.0 | 0.9294 | 6,185 | 14.92 | 92,293 |
| 7 | 5.1 | 0.24 | 0.23 | 250 | 40 | 123.1 | 0.9367 | 28,533 | 2.34 | 66,710 |
| 8 | 1.6 | 0.21 | 0.08 | 250 | 20 | 126.0 | 0.9372 | 7,480 | 10.67 | 79,819 |
| 8 | 7.6 | 0.25 | 0.33 | 250 | 20 | 125.8 | 0.9267 | 34,338 | 3.73 | 128,046 |

TABLE 1-continued

| Metal Complex | Poly. (g) | Cat. Amt. (µmol) | Eff. (MM g/g) | Octene (g) | $H_2$ (mmol) | $T_M$ (°C.) | Dens. (g/cc) | Mn (g/mol) | MWD | Mw (g/mol) |
|---|---|---|---|---|---|---|---|---|---|---|
| 8 | 3.4 | 0.24 | 0.16 | 250 | 40 | 93.7 | 0.9403 | 8,580 | 9.25 | 79,339 |
| 8 | 29.5 | 0.9 | 0.36 | 250 | 0 | 123.2 | 0.9247 | 8,406 | 26.76 | 224,972 |
| 11 | 39.8 | 7.5 | 0.11 | 250 | 40 | 116.6 | 0.9164 | 6,220 | 8.33 | 51,818 |
| 11 | 51.9 | 7.5 | 0.14 | 250 | 0 | 113.2 | 0.9133 | 25,333 | 6.54 | 165,629 |
| 11 | 54.6 | 5.0 | 0.23 | 250 | 0 | 111.3 | 0.9058 | 15,019 | 23.02 | 345,666 |
| 11 | 41.6 | 5.0 | 0.09 | 250 | 0 | 112.1 | 0.9055 | 18,021 | 11.16 | 201,026 |
| 12 | 33.8 | 3.75 | 0.19 | 350 | 40 | 113.7 | 0.9119 | 1,774 | 4.94 | 8,771 |
| 12 | 41.0 | 4.1 | 0.21 | 450 | 40 | 112.4 | 0.9042 | 1,829 | 5.32 | 9,733 |
| 12 | 47.7 | 4.25 | 0.23 | 250 | 0 | 115.1 | 0.9162 | 3,080 | 47.38 | 145,934 |
| 13 | 18.5 | 5.0 | 0.08 | 250 | 40 | 116.6 | 0.9133 | 3,137 | 20.08 | 62,992 |
| 13 | 38.4 | 7.5 | 0.11 | 250 | 0 | 112.6 | 0.9053 | 21,212 | 9.78 | 207,392 |

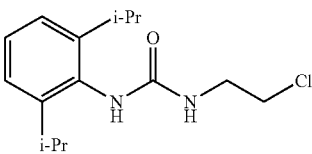 [SMILES: CC(C)c1cccc(C(C)C)c1NC(=O)NCCCl]

Synthesis of 1-(2-chloroethyl)-3-(2,6-diisopropylphenyl) urea: To a 500 mL round-bottom flask equipped with a magnetic stirbar was added dichloromethane (150 mL) and 2,6-di-iso-propylaniline (13 mL, 68.9 mmol, 1 equiv.). The vessel was cooled to 0° C. in a water/ice bath, after which 2-chloroethyl isocyanate (7.1 mL, 82.7 mmol, 1.2 equiv.) was added to the stirring solution drop-wise via syringe. The water/ice bath was removed and the reaction was allowed to warm to room temperature, stirring for a total of 16 h. During this time, a significant amount of white solid precipitated from solution. All volatiles were removed via rotary evaporation. The solid was triturated with cold 10:1 hexanes:diethyl ether (2×100 mL). The slurry was filtered, further washed with room temperature 10:1 hexanes:diethyl ether (2×100 mL), and dried in vacuo to afford the product as a white powder (18.9 g, 97% yield). The $^1$H NMR exhibited broad peaks at room temperature, but showed resolved peaks at 50° C. $^1$H NMR (500 MHz, Chloroform-d) δ 7.31 (t, J=7.7 Hz, 1H), 7.19 (d, J=7.7 Hz, 2H), 6.72 (br s, 1H), 4.65 (br s, 1H), 3.51 (t, J=5.6 Hz, 2H), 3.44 (t, J=5.6 Hz, 2H), 3.29 (hept, J=7.1 Hz, 2H), 1.21 (d, J=7.0 Hz, 12H). $^{13}$C NMR (126 MHz, Chloroform-d) δ 157.57, 147.96, 130.94, 128.88, 124.01, 44.29, 42.05, 28.36, 24.10 (br), 23.23 (br). HRMS (ESI) Calculated for $C_{15}H_{23}ClN_2O$ [M+H]$^+$: 283.1572. found: 283.1572.

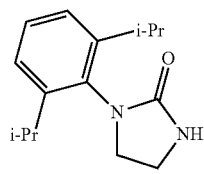

Synthesis of 1-(2,6-diisopropylphenyl)imidazolidin-2-one: In a nitrogen-filled glovebox, 1-(2-chloroethyl)-3-(2,6-diisopropylphenyl)urea (12.0 g, 42.4 mmol, 1 equiv.) and THF (100 mL) were added to a 250 mL round-bottom flask equipped with a magnetic stirbar. Dry sodium hydride (2.04 g, 84.9 mmol, 2 equiv.) was added slowly to the stirring slurry, being careful to wait for hydrogen evolution to cease between additions. The reaction was stirred at room temperature for 2 h. The vessel was removed from the glove box, and water (150 mL) was slowly added. The solution was extracted with ethyl acetate (2×100 mL). The combined organic layers were washed with brine (1×150 mL), dried over MgSO$_4$, filtered, and concentrated via rotary evaporation to yield the product as a white solid (10.3 g, 98% yield). $^1$H NMR (400 MHz, Chloroform-d) δ 7.32-7.26 (m, 1H), 7.17 (d, J=7.7 Hz, 2H), 5.80 (br s, 1H), 3.77-3.64 (m, 2H), 3.63-3.51 (m, 2H), 3.06 (hept, J=6.9 Hz, 2H), 1.24 (t, J=6.7 Hz, 12H). $^{13}$C NMR (101 MHz, Chloroform-d) δ 162.47, 148.07, 132.88, 128.72, 124.06, 49.00, 38.89, 28.52, 24.40, 24.32. HRMS (ESI) Calculated for $C_{15}H_{22}N_2O$: [M+H]$^+$: 247.1805. found: 247.1805.

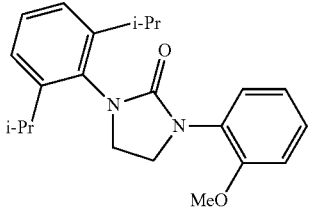 [SMILES: COc1ccccc1N1CCN(c2c(C(C)C)cccc2C(C)C)C1=O]

Synthesis of 1-(2,6-diisopropylphenyl)-3-(2-methoxyphenyl)imidazolidin-2-one: To a 200 mL Schlenk flask equipped with a magnetic stirbar was added copper (I) iodide (0.928 g, 4.87 mmol, 0.3 equiv.), K$_3$PO$_4$ (6.89 g, 32.5 mmol, 2 equiv.), 1-iodo-2-phenoxybenzene (2.11 mL, 16.2 mmol, 1 equiv.), and 1-(2,6-diisopropylphenyl)imidazolidin-2-one (4.0 g, 16.2 mmol, 1 equiv.). The vessel was sealed with a septum and purged with nitrogen. Subsequently, N,N'-dimethylethylenediamine (1.05 mL, 9.74 mmol, 0.6 equiv.) and N,N-dimethylacetamide (65 mL) were added via syringe. The reaction was placed into an aluminum heating block preheated to 130° C. and stirred for 24 h. After cooling to room temperature, the material was poured onto diethyl ether (250 mL) and washed with water (2×250 mL). The combined aqueous layers were back extracted with diethyl ether (1×250 mL), dried over MgSO$_4$, and filtered. The solution was concentrated via rotary evaporation. Adsorption onto silica gel, purification via flash column chromatography (ISCO, 220 g silica, 20-30% EtOAc in hexanes gradient), and concentration via rotary evaporation yielded the product as a white solid (5.03 g, 92% yield). $^1$H NMR (400 MHz, Chloroform-d) δ 7.44-7.38 (m, 1H), 7.31 (dd, J=8.3, 7.1 Hz, 1H), 7.23-7.16 (m, 3H), 7.00-6.93 (m, 2H), 4.01-3.91 (m, 2H), 3.87 (s, 3H), 3.79-3.65 (m, 2H), 3.16 (hept, J=6.9 Hz, 2H), 1.28 (d, J=6.1 Hz, 6H), 1.26 (d, J=6.1 Hz, 6H). $^{13}$C NMR (101 MHz, Chloroform-d) δ 158.72, 155.22, 148.25, 133.74, 129.23, 128.62, 128.54, 127.53, 123.97, 120.93, 112.33, 55.72, 46.73, 45.58, 28.62, 24.61, 24.27. HRMS (ESI) Calculated for C$_{22}$H$_{28}$N$_2$O$_2$: [M+H]$^+$: 353.2224. found 353.2229.

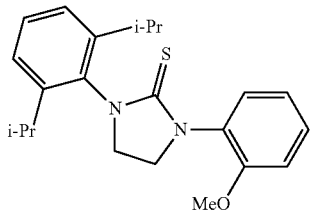 [SMILES: COc1ccccc1N1CCN(c2c(C(C)C)cccc2C(C)C)C1=S]

Synthesis of 1-(2,6-diisopropylphenyl)-3-(2-methoxyphenyl)imidazolidine-2-thione: To a 250 mL three-neck round-bottom flask equipped with a magnetic stirbar and a reflux condenser was added 1-(2,6-diisopropylphenyl)-3-(2-methoxyphenyl)imidazolidin-2-one (4.1 g, 11.6 mmol, 1 equiv.) and Lawesson's reagent (6.12 g, 15.2 mmol, 1.3 equiv.). The vessel was sealed with a septum. The vessel was evacuated and backfilled with nitrogen three times. P-xylene (50 mL) was added via syringe, the vessel was placed into an aluminum heating block preheated to 145° C., and stirred for 62 h. Upon cooling to room temperature, methanol (20 mL) and 1 M aqueous HCl (25 mL) were added via syringe, and the biphasic mixture was stirred at room temperature for 24 h. The mixture was poured onto toluene (75 mL) and washed with water (2×120 mL). The combined aqueous layers were extracted with toluene (3×75 mL). The combined organic layers were dried over MgSO$_4$, and concentrated via rotary evaporation. Adsorption onto silica gel, purification via flash column chromatography (ISCO, 330 g silica, 5-20% EtOAc in hexanes gradient), and concentration via rotary evaporation yielded the product as a white solid (2.96 g, 69% yield). $^1$H NMR (400 MHz, Chloroform-d) δ 7.44 (dd, J=7.6, 1.7 Hz, 1H), 7.40-7.28 (m, 2H), 7.26-7.19 (m, 2H), 7.05-6.97 (m, 2H), 4.15-4.03 (m, 2H), 4.01-3.91 (m, 2H), 3.89 (s, 3H), 3.10 (hept, J=6.9 Hz, 2H), 1.33 (d, J=6.8 Hz, 6H), 1.28 (d, J=7.0 Hz, 6H). $^{13}$C NMR (101 MHz, Chloroform-d) δ 184.86, 155.68, 147.49, 135.06, 130.70, 129.89, 129.32, 129.19, 124.37, 120.90, 112.57, 55.88, 50.72, 49.20, 28.66, 24.89, 24.55. HRMS (ESI) Calculated for C$_{22}$H$_{28}$N$_2$OS: [M+H]$^+$: 369.1995. found 369.1998.

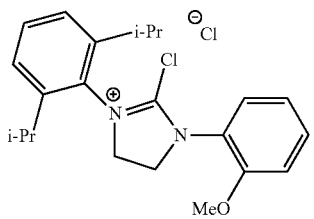 [SMILES: COc1ccccc1N1CC[N+](c2c(C(C)C)cccc2C(C)C)=C1Cl ; [Cl-]]

Synthesis of 2-chloro-3-(2,6-diisopropylphenyl)-1-(2-methoxyphenyl)-4,5-dihydro-1H-imidazol-3-ium chloride: To a 50-mL round-bottom flask equipped with a reflux condenser and a magnetic stirbar was added 1-(2,6-diisopropylphenyl)-3-(2-methoxyphenyl)imidazolidine-2-thione (2.8 g, 7.60 mmol, 1 equiv.). The vessel was evacuated and backfilled with nitrogen three times. Toluene (36 mL) and oxalyl chloride (5.40 mL, 60.8 mmol, 8 equiv.) were added via syringe. Upon addition of oxalyl chloride, the solution turned yellow. The vessel was placed into a room temperature aluminum heating block. The reaction was heated to 80° C. and stirred for 18 h. The volatile were removed in vacuo to yield a white solid. The vessel was transferred to a nitrogen-filled glovebox. The solid was triturated with toluene (10 mL), filtered, and further washed with toluene (3×5 mL). Drying in vacuo afforded a white solid (3.10 g, 87% yield). $^1$H NMR (400 MHz, Chloroform-d) δ 7.92 (dd, J=7.9, 1.7 Hz, 1H), 7.47-7.37 (m, 2H), 7.27-7.19 (m, 2H), 7.07-6.96 (m, 2H), 4.67 (br s, 2H), 3.85 (s, 3H), 3.07 (br s, 2H), 1.28 (d, J=6.8 Hz, 6H), 1.20 (d, J=6.8 Hz, 6H). $^{13}$C NMR (101 MHz, Chloroform-d) δ 157.88, 153.55, 146.48 (br), 132.42, 131.73, 129.48, 129.06, 125.26 (br), 122.78, 121.95, 111.94, 56.12, 54.05, 53.37, 28.76, 24.76, 24.30. HRMS (ESI) Calculated for C$_{22}$H$_{28}$ClN$_2$O$^+$: [M]$^+$: 371.1885. found 371.1885.

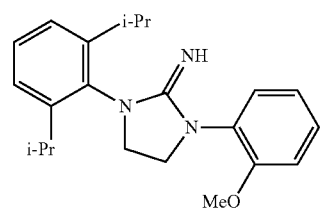 [SMILES: COc1ccccc1N1CCN(c2c(C(C)C)cccc2C(C)C)C1=N]

Synthesis of 1-(2,6-diisopropylphenyl)-3-(2-methoxyphenyl)imidazolidin-2-imine: In a nitrogen-filled glovebox 2-chloro-3-(2,6-diisopropylphenyl)-1-(2-methoxyphenyl)-4,5-dihydro-1H-imidazol-3-ium chloride (2.6 g, 6.38 mmol, 1 equiv.) was added to a 100 ml, round-bottom flask equipped with a magnetic stirbar. The vessel was sealed with a septum, removed from the glovebox, equipped with a reflux condenser, and the apparatus was evacuated and backfilled with nitrogen three times. Acetonitrile (18.2 mL) and 7 M ammonia in methanol (18.2 mL, 128 mmol, 20 equiv.) were added via syringe, and the reaction was placed in an aluminum block heated to 60° C. and stirred for 18 h. The vessel was allowed to cool to room temperature. All volatiles were removed in vacuo. The material was dissolved in CH$_2$Cl$_2$ (50 mL) and washed with water (90 mL). The aqueous phase was extracted with CH$_2$Cl$_2$ (3×50 mL). The combined organic phases were washed with brine (1×50 mL), dried over MgSO$_4$, and concentrated via rotary evaporation to yield the HCl salt as a white solid. The material was dissolved in EtOH (5 mL), and 1 M aqueous NaOH (20 mL) was added. The solution was stirred at room temperature for 5 min, then poured onto 1 M aqueous NaOH (100 mL). The aqueous phase was extracted with CH$_2$Cl$_2$ (4×50 mL). The combined organic phases were washed with brine (150 mL), dried over MgSO$_4$, filtered, and concentrated in vacuo to afford the free base as a white solid (2.14 g, 95% yield). $^1$H NMR (400 MHz, Chloroform-d) δ 7.30-7.18 (m, 2H), 7.01 (s, 2H), 6.93 (dd, J=7.7, 6.9 Hz, 3H), 4.78 (s, 1H), 3.84 (dd, J=9.2, 6.8 Hz, 2H), 3.80 (s, 3H), 3.73-3.66 (m, 2H), 2.99 (hept, J=6.8 Hz, 2H), 1.18 (d, J=6.9 Hz, 6H), 1.14 (d, J=6.8 Hz, 6H). $^{13}$C NMR (101 MHz, Chloroform-d) δ 159.48, 155.75, 148.78, 132.77 (br), 130.11, 129.06, 128.05 (br), 124.10, 121.06, 112.24, 55.60, 48.70, 47.68, 28.19, 24.69, 24.07. HRMS (ESI) Calculated for C$_{22}$H$_{29}$N$_3$O: [M+H]$^+$: 352.2383. found 352.2394.

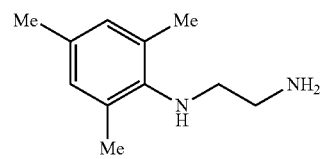 [SMILES: Cc1cc(C)c(NCCN)c(C)c1]

Synthesis of N¹-mesitylethane-1,2-diamine: In a 500 mL round-bottom flask, a suspension of 2-bromoethylamine hydrobromide (20.4 g, 99.7 mmol, 1 equiv.) and 2,4,6-trimethylaniline (28 mL, 199 mmol, 2 equiv.) was refluxed in toluene (150 mL) for 72 h. During the reaction, a significant amount of material crashed out of solution, forming a cake on the top of the liquid phase. The suspension was allowed to cool to room temperature, resulting in further precipitation of solid. Water (150 mL) was added, resulting in the majority of material dissolving in solution. A 50% w/w solution of NaOH in water (50 mL) was added slowly to the stirring biphasic mixture, causing all solids to dissolve. The organic phase was separated from the aqueous phase. The aqueous phase was further washed with toluene (2×100 mL). The combined organic phases were dried over MgSO₄, filtered, and concentrated in vacuo. Adsorption onto silica gel, purification via flash column chromatography (ISCO, 330 g silica, 100% EtOAc followed by 9:1:0.1 DCM:MeOH:Et₃N isocratic), and concentration via rotary evaporation yielded the product as an amber oil (13.9 g, 78% yield). $^1$H NMR (400 MHz, Chloroform-d) δ 6.83 (s, 2H), 3.01-2.94 (m, 2H), 2.93-2.86 (m, 2H), 2.29 (s, 6H), 2.24 (s, 3H), 1.95 (br s, 2H). $^{13}$C NMR (101 MHz, Chloroform-d) δ 143.55, 131.21, 129.75, 129.41, 51.25, 42.57, 20.58, 18.39. HRMS (ESI) Calculated for $C_{11}H_{18}N_2$: [M+H]⁺: 179.1543. found 179.1543.

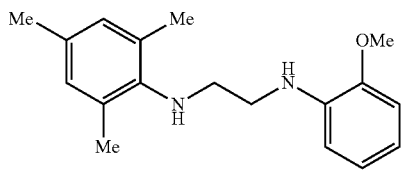 [SMILES: COc1ccccc1NCCNc1c(C)cc(C)cc1C]

Synthesis of N¹-mesityl-N²-(2-methoxyphenyl)ethane-1,2-diamine: In a nitrogen filled glovebox, BrettPhos palladacycle precatalyst (0.107 g, 0.118 mmol, 1 mol %), BrettPhos (63.4 mg, 0.118 mmol, 1 mol %), and sodium tert-butoxide (2.27 g, 23.6 mmol, 2 equiv.) were added to a reaction vial. N¹-mesitylethane-1,2-diamine (2.53 g, 14.2 mmol, 1.2 equiv.) and 2-chloroanisole (1.5 mL, 11.8 mmol, 1 equiv.) were added to a separate vial, dissolved in 12 mL dioxane, and the solution was subsequently added to the vial containing the catalyst. The vial was capped, and the reaction was stirred at 80° C. for 18 h. The vial was removed from the glove box, poured onto water (100 mL), and extracted with ethyl acetate (2×100 mL). The combined organic layers were dried over MgSO₄, filtered, and concentrated. Adsorption onto silica gel, purification via flash column chromatography (ISCO, 220 g, 10-27% EtOAc in hexanes), and concentration via rotary evaporation yielded the product as a clear oil which turned to a light pink oil (3.296 g, 98% yield). $^1$H NMR (400 MHz, Chloroform-d) δ 6.86 (td, J=7.6, 1.4 Hz, 1H), 6.81 (s, 2H), 6.78 (dd, J=7.9, 1.4 Hz, 1H), 6.70-6.67 (m, 1H), 6.67-6.62 (m, 1H), 3.84 (s, 3H), 3.34 (dd, J=6.6, 4.9 Hz, 2H), 3.28-3.16 (m, 2H), 2.24 (s, 6H), 2.22 (s, 3H). $^{13}$C NMR (101 MHz, Chloroform-d) δ 147.20, 143.24, 138.34, 131.54, 130.03, 129.64, 121.44, 116.86, 110.18, 109.67, 55.52, 47.92, 44.34, 20.73, 18.42. HRMS (ESI) Calculated for $C_{18}H_{24}N_2O$: [M+H]⁺: 285.1961. found 285.1966.

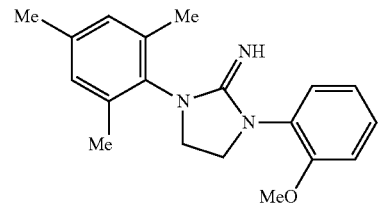 [SMILES: COc1ccccc1N1CCN(c2c(C)cc(C)cc2C)C1=N]

Synthesis of 1-mesityl-3-(2-methoxyphenyl)imidazolidin-2-imine: Caution! Cyanogen bromide is highly toxic. All waste should be disposed of as a basic solution. Care should be taken during workups as to avoid possible contact with deadly cyanide! The excess nitrogen stream from reactions should be passed through 1 M aqueous NaOH solution to trap any possible cyanide-containing byproducts. N¹-mesityl-N²-(2-methoxyphenyl)ethane-1,2 -diamine (3.2 g, 11.3 mmol, 1 equiv.) was added to a 25 mL round bottom flask equipped with a reflux condenser. The vessel was evacuated and backfilled with nitrogen three times, after which anhydrous ethanol (4 mL) was added. The solution is cooled in an ice bath, and subsequently a solution of BrCN (1.31 g, 12.4 mmol, 1.1 equiv.) in anhydrous ethanol (3 mL) is added dropwise. The vial is rinsed with an additional anhydrous ethanol (1 mL), which is also added to the diamine solution. The ice bath is removed, and the vessel is allowed to warm to room temperature, then heated to reflux (105° C.) for 19 h. The reaction was allowed to cool to room temperature, and 1 M aqueous NaOH (10 mL) was added to the reaction to quench the remaining cyanogen bromide. Mixture was stirred for 10 min, then poured onto 1 M aqueous NaOH solution (100 mL). The aqueous phase was extracted with CH₂Cl₂ (4×50 mL). The combined organic phases were washed with brine (1×150 mL), dried over MgSO₄, and concentrated in vacuo to yield a brown solid (4346-B, 3.48 g, 99% yield). $^1$H NMR (400 MHz, Chloroform-d) δ 7.37 (dd, J=8.0, 1.6 Hz, 1H), 7.19-7.12 (m, 1H), 6.94-6.88 (m, 4H), 4.55 (br s, 1H), 3.89-3.84 (m, 3H), 3.83 (s, 3H), 3.72-3.66 (m, 2H), 2.25 (s, 3H), 2.24 (s, 6H). $^{13}$C NMR (101 MHz, Chloroform-d) δ 158.61, 155.84, 137.90, 137.79, 133.37, 129.81, 129.42, 129.27, 128.29, 120.94, 112.24, 55.59, 47.46, 46.03, 20.97, 17.67. HRMS (ESI) Calculated for $C_{19}H_{23}N_3O$: [M+H]': 310.1914. found 310.1917.

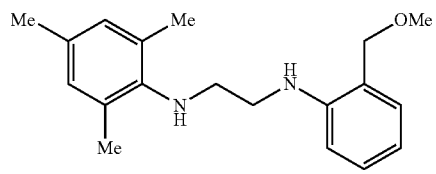 [SMILES: COCc1ccccc1NCCNc1c(C)cc(C)cc1C]

Synthesis of N¹-mesityl-N²-(2-(methoxymethyl)phenyl)ethane-1,2-diamine: In a nitrogen filled glovebox, Pd(OAc)₂ (25 mg, 0.111 mmol, 1 mol %), and Josiphos [(R), (S$_p$)—CyPF-t-Bu] (61.3 mg, 0.111 mmol, 1 mol %), were dissolved in DME (11 mL). N¹-mesitylethane-1,2-diamine (2.36 g, 13.3 mmol, 1.2 equiv.) and 1-bromo-2-(methoxymethyl)benzene (1.6 mL, 11.0 mmol, 1 equiv.), and sodium tert-butoxide (1.49 g, 15.5 mmol, 1.4 equiv.) were added to a separate vial. The catalyst and ligand solution was subsequently added to the vial containing the substrate. The vial was capped, and the reaction was stirred at 80° C. for 17 h. The vial was removed from the glove box, poured onto water (100 mL), and extracted with ethyl acetate (2×100 mL). The combined organic layers were dried over MgSO$_4$, filtered, and concentrated. Adsorption onto silica gel, purification via flash column chromatography (ISCO, 220 g, 10-20% EtOAc in hexanes), and concentration via rotary evaporation yielded the product as a thick light-brown oil (2.86 g, 87% yield). $^1$H NMR (400 MHz, Chloroform-d) δ 7.26-7.21 (m, 1H), 7.10 (dd, J=7.6, 1.6 Hz, 1H), 6.85 (s, 2H), 6.73-6.67 (m, 2H), 5.09 (br s, 1H), 4.49 (s, 2H), 3.42-3.36 (m, 2H), 3.34 (s, 3H), 3.25-3.20 (m, 2H), 2.29 (s, 6H), 2.25 (s, 3H). $^{13}$C NMR (101 MHz, Chloroform-d) δ 147.66, 143.12, 131.63, 130.10, 130.04, 129.57, 129.46, 122.03, 116.59, 110.45, 74.12, 57.45, 47.72, 43.91, 20.57, 18.23. HRMS (ESI) Calculated for C$_{17}$H$_{26}$N$_2$O: [M+H]$^+$: 299.2118. found 299.2119.

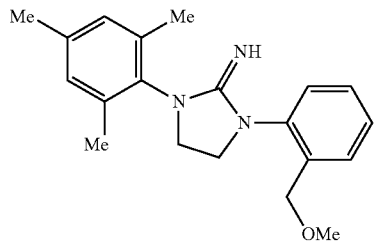 [SMILES: COCc1ccccc1N1CCN(c2c(C)cc(C)cc2C)C1=N]

Synthesis of 1-mesityl-3-(2-(methoxymethyl)phenyl)imidazolidin-2-imine: Caution! Cyanogen bromide is highly toxic. All waste should be disposed of as a basic solution. Care should be taken during workups as to avoid possible contact with deadly cyanide! The excess nitrogen stream from reactions should be passed through 1 M aqueous NaOH solution to trap any possible cyanide-containing byproducts. N$^1$-mesityl-N$^2$-(2-(methoxymethyl)phenyl)ethane-1,2-diamine (2.81 g, 9.42 mmol, 1 equiv.) was added to a 25 mL round bottom flask equipped with a reflux condenser. The vessel was evacuated and backfilled with nitrogen three times, after which anhydrous ethanol (4 mL) was added. Subsequently a solution of BrCN (1.10 g, 10.4 mmol, 1.1 equiv.) in anhydrous ethanol (3 mL) is added dropwise. The vial is rinsed with an additional anhydrous ethanol (1 mL), which is also added to the diamine solution. The reaction was heated to reflux (100° C.) for 15 h. The reaction was allowed to cool to room temperature, and 1 M aqueous NaOH (10 mL) was added to the reaction to quench the remaining cyanogen bromide. Mixture was stirred for 5 min, then poured onto 1 M aqueous NaOH solution (100 mL). The aqueous phase was extracted with CH$_2$Cl$_2$ (3×50 mL). The combined organic were dried over MgSO$_4$, and concentrated in vacuo to yield a yellow oil. Compared to other analogues, the crude product was not a single, clean species. The material was adsorbed onto basic alumina, purified via flash column chromatography (ISCO, 80 g basic alumina, 0-100% EtOAc in hexanes gradient), and concentrated via rotary evaporation yielded the product as an off-white solid (2.05 g, 67% yield). $^1$H NMR (400 MHz, Chloroform-d) δ 7.54-7.49 (m, 1H), 7.38-7.34 (m, 2H), 7.33-7.26 (m, 1H), 6.94 (d, J=0.7 Hz, 2H), 4.58 (br s, 2H), 4.02 (s, 1H), 3.95-3.81 (m, 2H), 3.73-3.64 (m, 2H), 3.42 (s, 3H), 2.36-2.25 (m, 9H). $^{13}$C NMR (101 MHz, Chloroform-d) δ 158.47, 139.67, 137.77, 136.85, 133.73, 129.55, 128.87, 127.20, 126.83, 71.18, 58.40, 48.76, 45.84, 20.97, 17.80. HRMS (ESI) Calculated for C$_{20}$H$_{25}$N$_3$O: [M+H]$^+$: 324.2070. found 324.2071.

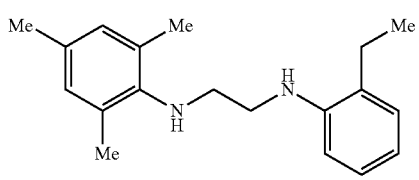 [SMILES: CCc1ccccc1NCCNc1c(C)cc(C)cc1C]

Synthesis of N$^1$-(2-ethylphenyl)-N$^2$-mesitylethane-1,2-diamine: In a nitrogen filled glovebox, Pd(OAc)$_2$ (26 mg, 0.116 mmol, 1 mol %), and Josiphos [(R), (S$_p$)—CyPF-t-Bu] (64.2 mg, 0.116 mmol, 1 mol %), were dissolved in DME (11 mL). N$^1$-mesitylethane-1,2-diamine (2.47 g, 13.9 mmol, 1.2 equiv.) and 1-bromo-2-ethylbenzene (1.6 mL, 11.6 mmol, 1 equiv.), and sodium tert-butoxide (1.56 g, 16.2 mmol, 1.4 equiv.) were added to a separate vial. The catalyst and ligand solution was subsequently added to the vial containing the substrate. The vial was capped, and the reaction was stirred at 80° C. for 17 h. The vial was removed from the glove box, poured onto water (100 mL), and extracted with ethyl acetate (2×100 mL). The combined organic layers were dried over MgSO$_4$, filtered, and concentrated. Adsorption onto silica gel, purification via flash column chromatography (EXP-14-AK9305, ISCO, 120 g gold silica, 0-30% EtOAc in hexanes gradient), and concentration via rotary evaporation yielded the product as a pale yellow oil (2.97 g, 91% yield). $^1$H NMR (400 MHz, Chloroform-d) δ 7.17 (td, J=7.8, 1.6 Hz, 1H), 7.15-7.12 (m, 1H), 6.88 (s, 2H), 6.77 (td, J=7.4, 1.2 Hz, 1H), 6.72-6.69 (m, 1H), 3.42-3.37 (m, 2H), 3.30-3.26 (m, 2H), 2.54 (q, J=7.5 Hz, 2H), 2.32 (d, J=0.7 Hz, 6H), 2.28 (s, 3H), 1.30 (t, J=7.5 Hz, 3H). $^{13}$C NMR (101 MHz, Chloroform-d) δ 145.70, 142.98, 131.92, 130.21, 129.57, 128.07, 127.98, 127.02, 117.46, 110.21, 47.79, 44.67, 23.95, 20.60, 18.28, 13.00. HRMS (ESI) Calculated for C$_{19}$H$_{26}$N$_2$: [M+H]$^+$: 283.2169. found 283.2169.

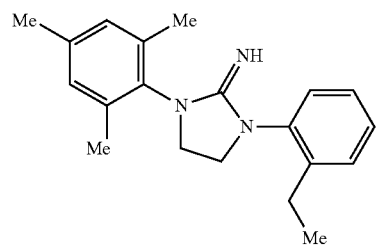 [SMILES: CCc1ccccc1N1CCN(c2c(C)cc(C)cc2C)C1=N]

Synthesis of 1-(2-ethylphenyl)-3-mesitylimidazolidin-2-imine: Caution! Cyanogen bromide is highly toxic. All waste should be disposed of as a basic solution. Care should be taken during workups as to avoid possible contact with deadly cyanide! The excess nitrogen stream from reactions should be passed through 1 M aqueous NaOH solution to trap any possible cyanide-containing byproducts. $N^1$-(2-ethylphenyl)-$N^2$-mesitylethane-1,2-diamine (2.97 g, 10.5 mmol, 1 equiv.) was added to a 25 mL round bottom flask equipped with a reflux condenser. The vessel was evacuated and backfilled with nitrogen three times. Subsequently a solution of BrCN (1.23 g, 11.6 mmol, 1.1 equiv.) in anhydrous ethanol (8 mL) was added. The reaction was heated to reflux (100° C.) for 15 h. The reaction was allowed to cool to room temperature, and 1 M aqueous NaOH (10 mL) was added to the reaction to quench the remaining cyanogen bromide. Mixture was stirred for 5 min, then poured onto 1 M aqueous NaOH solution (100 mL). The aqueous phase was extracted with $CH_2Cl_2$ (3×50 mL). The combined organic were dried over $MgSO_4$, and concentrated in vacuo to yield a yellow oil. The $^1H$ NMR spectrum looked clean, however extra peaks were present in the $^{13}C$ NMR spectrum. The material was adsorbed onto basic alumina, purified via flash column chromatography (ISCO, 80 g basic alumina, 0-93% EtOAc in hexanes gradient), and concentrated via rotary evaporation to yield a pale yellow oil (3.23 g, 77% yield), which still showed stray peaks in the $^{13}C$ NMR spectrum. NMR spectra at 50° C. were cleaner, indicating that the compound is clean, albeit with different conformational isomers at room temperature. Over several days, the oil solidified. $^1H$ NMR (400 MHz, Chloroform-d, 25° C.) δ 7.36-7.23 (m, 4H), 6.95 (s, 2H), 3.96 (br s, 1H), 3.86-3.76 (m, 2H), 3.75-3.62 (m, 2H), 2.78 (q, J=7.6 Hz, 2H), 2.30 (s, 6H), 2.29 (s, 3H), 1.28 (t, J=7.6 Hz, 3H). $^{13}C$ NMR (101 MHz, Chloroform-d, 50° C.) δ 158.70, 143.17, 139.58 (br), 137.65, 137.48, 134.20 (br), 129.47, 129.33, 127.57, 127.48, 127.04, 48.74, 45.77, 24.33, 20.87, 17.71, 14.66. HRMS (ESI) Calculated for $C_{20}H_{26}N_3$: $[M+H]^+$: 308.2121. found 308.2122.

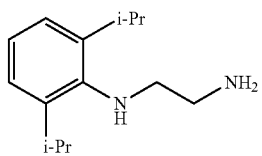 [SMILES: CC(C)c1cccc(C(C)C)c1NCCN]

Synthesis of $N^1$-(2,6-diisopropylphenyl)ethane-1,2-diamine: In a round-bottom flask, 2,6-di-iso-propylaniline (15 mL, 79.5 mmol, 2 equiv.) was added to toluene (60 mL). 2-bromoethylamine hydrobromide (8.15 g, 39.8 mmol, 1 equiv.) was added and the reaction was heated at reflux until completion. The reaction was allowed to cool to room temperature, resulting in the solidification of the solution. Water (240 mL), toluene (200 mL), and 50% w/w aqueous NaOH solution (80 mL) were added, and the aqueous phase was saturated with NaCl. The organic phase was separated, and the aqueous phase was extracted with additional toluene. The combined organic phases were washed with brine, dried over $Na_2SO_4$, filtered, and concentrated in vacuo. Adsorption onto silica gel, purification via flash column chromatography (ISCO, 330 g silica, 100% EtOAc followed by 9:1:0.1 DCM:MeOH:$Et_3N$ isocratic), and concentration via rotary evaporation yielded the product as a yellow oil (6.06 g, 69% yield). $^1H$ NMR (400 MHz, Chloroform-d) δ 7.12-7.01 (m, 3H), 3.32 (hept, J=6.9 Hz, 2H), 3.00-2.87 (m, 4H), 2.13 (br s, 2H), 1.24 (d, J=6.9 Hz, 12H). $^{13}C$ NMR (101 MHz, Chloroform-d) δ 143.26, 142.51, 123.69, 123.49, 54.25, 42.51, 27.57, 24.27. HRMS (ESI) Calculated for $C_{14}H_{24}N_2$: $[M+H]^+$: 221.2012. found 221.2012.

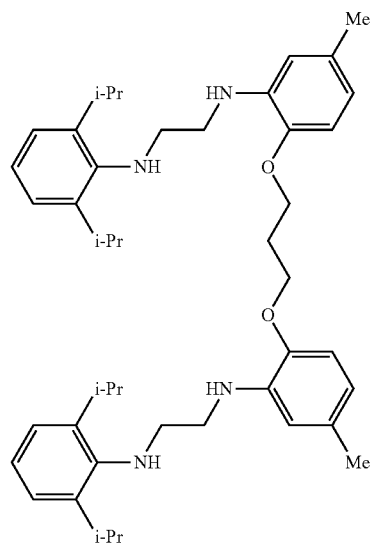 [SMILES: Cc1ccc(OCCCOc2ccc(C)cc2NCCNc2c(C(C)C)cccc2C(C)C)c(NCCNc2c(C(C)C)cccc2C(C)C)c1]

Synthesis of $N^1,N^{1'}$-((propane-1,3-diylbis(oxy))bis(5-methyl-2,1-phenylene))bis($N^2$-(2,6-diisopropylphenyl)ethane-1,2-diamine): In a nitrogen filled glovebox, $Pd(OAc)_2$ (11.4 mg, 0.051 mmol, 1 mol %), and Josiphos [(R),($S_p$)—CyPF-t-Bu] (28.1 mg, 0.051 mmol, 1 mol %), were dissolved in DME (5 mL). $N^1$-(2,6-diisopropylphenyl)ethane-1,2-diamine (2.46 g, 11.2 mmol, 2.2 equiv.) and 1,3-bis(2-bromo-4-methylphenoxy)propane (2.10 g, 5.07 mmol, 1 equiv.), and sodium tert-butoxide (1.36 g, 1.36 mmol, 2.8 equiv.) were added to a separate vial. The catalyst and ligand solution was subsequently added to the vial containing the substrate. The vial was capped, and the reaction was stirred at 80° C. for 15 h. The vial was removed from the glove box, poured onto water (100 mL), and extracted with ethyl acetate (3×50 mL). The combined organic layers were dried over $MgSO_4$, filtered, and concentrated. Adsorption onto silica gel, purification via flash column chromatography (ISCO, 220 g, 1-16% EtOAc in hexanes), and concentration via rotary evaporation yielded the product as a thick oil which partially solidified over several days (2.40 g, 68% yield). $^1H$ NMR (400 MHz, Chloroform-d) δ 7.16-7.00 (m, 6H), 6.66 (d, J=8.0 Hz, 2H), 6.49 (d, J=2.0 Hz, 2H), 6.44-6.37 (m, 2H), 4.58 (br s, 2H), 4.18 (t, J=6.2 Hz, 4H), 3.40 (t, J=5.8 Hz, 4H), 3.25 (hept, J=6.8 Hz, 4H), 3.12 (t, J=5.8 Hz, 4H), 2.30 (p, J=6.2 Hz, 2H), 2.24 (s, 6H), 1.19 (d, J=6.8 Hz, 24H). $^{13}$C NMR (101 MHz, Chloroform-d) δ 144.10, 142.84, 142.72, 137.85, 130.78, 123.97, 123.52, 116.87, 111.37, 110.71, 65.19, 50.62, 44.15, 29.64, 27.58, 24.25, 21.13. HRMS (ESI) Calculated for $C_{45}H_{64}N_4O_2$: [M+H]$^+$: 693.5102. found 693.5113.

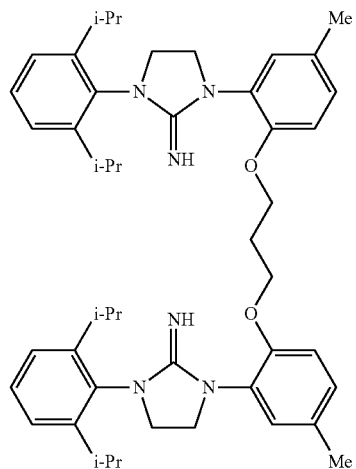 [SMILES: Cc1ccc(OCCCOc2ccc(C)cc2N2CCN(c3c(C(C)C)cccc3C(C)C)C2=N)c(N2CCN(c3c(C(C)C)cccc3C(C)C)C2=N)c1]

Synthesis of 3,3'-((propane-1,3-diylbis(oxy))bis(5-methyl-2,1-phenylene))bis(1-(2,6-diisopropylphenyl)imidazolidin-2-imine): Caution! Cyanogen bromide is highly toxic. All waste should be disposed of as a basic solution. Care should be taken during workups as to avoid possible contact with deadly cyanide! The excess nitrogen stream from reactions should be passed through 1 M aqueous NaOH solution to trap any possible cyanide-containing byproducts. $N^1,N^{1''}$-((propane-1,3-diylbis(oxy))bis(5-methyl-2,1-phenylene))bis($N^2$-(2,6-diisopropylphenyl)ethane-1,2-diamine) (2.23 g, 3.22 mmol, 1 equiv.) was added to a 50 mL round bottom flask equipped with a reflux condenser. The vessel was evacuated and backfilled with nitrogen three times Anhydrous ethanol (9 mL) was added, however all tetraamine did not dissolve. Subsequently a solution of BrCN (0.682 g, 6.44 mmol, 2 equiv.) in anhydrous ethanol (6 mL) was added. The vial containing the BrCN solution was washed with additional ethanol (2 mL), and this was added to the tetraamine mixture. The reaction was heated to reflux (95° C.) for 15 h. A small aliquot was analyzed via LC-MS, showing a mixture of starting material, monoaddition, and diaddition. A solution of BrCN (0.682 g, 6.44 mmol, 2 equiv.) in ethanol (5 mL) was added to the reaction, which was heated at reflux (105° C.) for a further 16 h. The reaction was allowed to cool to room temperature, and 1 M aqueous NaOH (20 mL) was added to the reaction to quench the remaining cyanogen bromide. Mixture was stirred for 5 min, then poured onto 1 M aqueous NaOH solution (150 mL). The aqueous phase was extracted with $CH_2Cl_2$ (1×100 mL, 2×50 mL). The combined organic were dried over $MgSO_4$, and concentrated in vacuo to yield an off-white solid (2.6 g, 97% yield) (3.23 g, 77% yield). Despite drying in vacuo for several days, the material contained one equivalent of hexane. $^1$H NMR (400 MHz, Chloroform-d) δ 7.34 (dd, J=8.2, 7.2 Hz, 2H), 7.29 (s, 2H), 7.20 (s, 4H), 6.98 (ddd, J=8.3, 2.3, 0.8 Hz, 2H), 6.86 (d, J=8.4 Hz, 2H), 4.24 (t, J=6.2 Hz, 4H), 4.15 (br s, 2H), 3.85 (dd, J=8.7, 6.4 Hz, 4H), 3.67 (dd, J=8.3, 6.8 Hz, 4H), 3.17 (hept, J=6.9 Hz, 4H), 2.33 (p, J=6.2 Hz, 3H), 2.28 (s, 6H), 1.25 (d, J=2.9 Hz, 12H), 1.24 (d, J=2.8 Hz, 12H). $^{13}$C NMR (101 MHz, Chloroform-d) δ 159.77, 152.72, 149.16, 133.76 (br), 130.73, 130.25, 129.64, 128.87, 128.10, 124.40, 113.08, 65.21, 48.48, 47.09, 29.59, 28.34, 24.59, 24.52, 20.53. HRMS (ESI) Calculated for $C_{47}H_{62}N_6O_2$: [M+H]$^+$: 743.5007. found 743.5009.

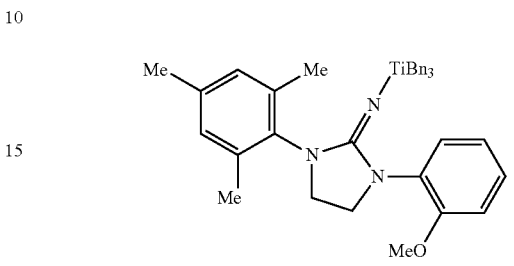

Synthesis of Tribenzyl((1-mesityl-3-(2-methoxyphenyl)imidazolidin-2-ylidene)amino)titanium: In a nitrogen-filled glovebox, a solution of 1-mesityl-3-(2-methoxyphenyl)imidazolidin-2-imine (0.150 g, 0.485 mmol, 1 equiv.) in benzene-d$^6$ (2 mL) was added to a vial containing a dark red solution of TiBn$_4$ (0.200 g, 0.485 mmol, 1 equiv.) in benzene-d$^6$ (2 mL) The solution was stirred at room temperature for 30 min, during which time the solution significantly lightened in color. All volatiles were removed in vacuo, yielding a thick oil. The oil was dissolved in toluene (1 ml). Hexanes (10 mL) was added to the stirring toluene solution, resulting in a hazy orange color. The vial was stored in a −30° C. freezer for 4 days, during which time orange crystals precipitated from solution. The solid was filtered, washed with cold (−30° C.) hexanes, and dried in vacuo to yield the product as orange crystals (0.158 g, 52% yield). $^1$H NMR (400 MHz, Benzene-d$_6$) δ 7.30 (dd, J=7.7, 1.7 Hz, 1H), 7.12-7.02 (m, 6H), 6.96 (ddd, J=8.2, 7.5, 1.7 Hz, 1H), 6.90-6.83 (m, 3H), 6.77 (td, J=7.6, 1.3 Hz, 1H), 6.71 (s, 2H), 6.57-6.52 (m, 6H), 6.50 (dd, J=8.3, 1.3 Hz, 1H), 3.55-3.43 (m, 2H), 3.33 (s, 3H), 3.17-3.07 (m, 2H), 2.23 (s, 6H), 2.01 (s, 3H), 1.99 (s, 6H). $^{13}$C NMR (101 MHz, Benzene-d$_6$) δ 155.73, 146.13, 145.23, 137.80, 137.24, 134.41, 130.73, 129.16, 128.89, 128.48, 128.45, 127.92, 121.72, 121.07, 111.67, 78.17, 54.95, 46.35, 45.02, 20.55, 17.60.

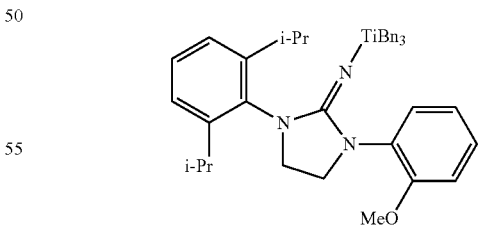

Synthesis of Tribenzyl((1-(2,6-diisopropylphenyl)-3-(2-methoxyphenyl)imidazolidin-2-ylidene)amino)titanium: In a nitrogen-filled glovebox, a solution of 1-(2,6-diisopropylphenyl)-3-(2-methoxyphenyl)imidazolidin-2-imine (0.150 g, 0.427 mmol, 1 equiv.) in toluene-d$^8$ (10 mL) was added dropwise over several minutes to a vial containing a dark red solution of TiBn$_4$ (0.176 g, 0.427 mmol, 1 equiv.) in toluene-d$^8$ (2 mL). The solution was stirred at room temperature for 1 h, during which time the solution significantly lightened in color. NMR shows a 3.5:1 ratio of tribenzyl:dibenzyl species. All volatiles were removed in vacuo, yielding a thick dark orange oil. The oil was dissolved in toluene (1 mL), and hexanes (10 mL) was added dropwise to the stirring toluene solution. The resulting dark orange solution was filtered through a 0.5 micron syringe filter and stored in a −30° C. freezer for 16 h. The resulting orange crystalline material was filtered, washed with cold hexanes, and dried in vacuo. NMR showed a 5.7:1 tribenzyl:dibenzyl ratio. The material was dissolved in toluene (2 mL), hexanes (10 mL) was added, and the solution was again subjected to a 0.5 micron syringe filtration. The resulting clear orange solution was stored in a −30° C. freezer for 16 h, resulting in the precipitation of an orange solid. The solid was filtered, washed with cold hexanes, and dried in vacuo to yield the product as an orange solid (0.150 g, 52% yield). Material still contains ~10% dibenzyl byproduct. $^1$H NMR (400 MHz, Benzene-$d_6$) δ 7.24 (dd, J=7.7, 1.7 Hz, 1H), 7.13-6.93 (m, 12H), 6.86 (t, J=7.3 Hz, 3H), 6.73 (td, J=7.6, 1.3 Hz, 1H), 6.57 (dd, J=8.2, 1.4 Hz, 6H), 6.47 (dd, J=8.3, 1.3 Hz, 1H), 3.52-3.46 (m, 2H), 3.34 (s, 3H), 3.36-3.24 (m, 2H), 2.00 (s, 6H), 1.30 (d, J=6.8 Hz, 6H), 1.16 (d, J=7.0 Hz, 6H). $^{13}$C NMR (101 MHz, Benzene-$d_6$) δ 155.89, 148.01, 147.33, 145.57, 134.43, 131.16, 129.09, 128.86, 128.79, 128.42, 127.77, 124.14, 121.66, 121.00, 111.50, 79.74, 54.91, 47.64, 46.35, 28.55, 24.81, 24.17.

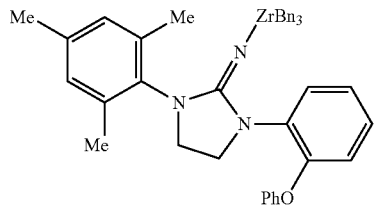

Synthesis of Tribenzyl((1-mesityl-3-(2-phenoxyphenyl)imidazolidin-2-ylidene)amino)zirconium: In a nitrogen-filled glovebox, a solution of 1-mesityl-3-(2-phenoxyphenyl)imidazolidin-2-imine (0.200 g, 0.538 mmol, 1 equiv.) in benzene-$d_6$ (3 mL) was added dropwise to a stirring solution of ZrBn$_4$ (0.245 g, 0.538 mmol, 1 equiv.) in benzene-$d_6$ (3 mL). The solution was stirred at room temperature for 1 h, resulting in a clear, yellow solution. All volatiles were removed in vacuo, yielding a thick oil. Hexane (15 mL) was added and the solution was stirred vigorously for 1 h, however the thick oil did not fully dissolve in the hexanes layer. The hexanes layer was decanted and stored in a −30° C. freezer for 3 h, yielding a yellow precipitate. The remaining thick oil was dissolved in toluene (1 mL). Hexane (15 mL) was added to the stirring toluene solution, resulting in the formation of a yellow precipitate. The suspension was stored in a −30° C. freezer for 3 h. The two batches of precipitated material were combined, filtered, washed with −30° C. hexane, and dried in vacuo to yield a yellow solid (0.300 g, 76% yield). $^1$H NMR (400 MHz, Benzene-$d_6$) δ 7.44-7.39 (m, 1H), 7.14-6.77 (m, 17H), 6.69 (s, 2H), 6.38-6.29 (m, 6H), 3.50-3.44 (m, 2H), 2.96-2.89 (m, 2H), 2.01 (s, 3H), 2.00 (s, 6H), 1.42 (s, 6H). $^{13}$C NMR (101 MHz, Benzene-$d_6$) δ 157.63, 151.98, 146.83, 142.62, 137.66, 137.29, 134.53, 132.41, 131.15, 129.72, 129.71, 129.10, 128.13, 126.79, 124.88, 122.78, 121.70, 121.18, 117.17, 61.54, 45.71, 44.50, 20.54, 17.45.

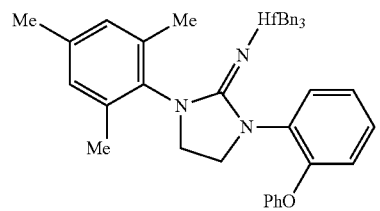

Synthesis of Tribenzyl((1-mesityl-3-(2-phenoxyphenyl)imidazolidin-2-ylidene)amino)hafnium: In a nitrogen-filled glovebox, a solution of 1-mesityl-3-(2-phenoxyphenyl)imidazolidin-2-imine (0.300 g, 0.808 mmol, 1 equiv.) in benzene-$d_6$ (4 mL) was added dropwise to a stirring solution of HfBn$_4$ (0.245 g, 0.538 mmol, 1 equiv.) in benzene-$d_6$ (4 mL). The solution was stirred at room temperature for 1 h, resulting in a clear, colorless solution. All volatiles were removed in vacuo, yielding a thick oil. Hexane (15 mL) was added and the solution was stirred vigorously for 1 h. The vial was placed in a −30° C. freezer for 4 h. The suspension was filtered, washed with −30° C. hexane, and dried in vacuo to yield an off-white solid (0.550 g, 83% yield). $^1$H NMR (400 MHz, Benzene-$d_6$) δ 7.31 (ddd, J=7.8, 1.5, 0.6 Hz, 1H), 7.13-6.78 (m, 17H), 6.69 (s, 2H), 6.46 (dd, J=8.2, 1.2 Hz, 6H), 3.52-3.42 (m, 2H), 2.98-2.87 (m, 2H), 2.01 (s, 3H), 1.98 (s, 6H), 1.27 (s, 6H). $^{13}$C NMR (101 MHz, Benzene-$d_6$) δ 157.70, 151.83, 149.97, 142.64, 137.65, 137.32, 134.46, 132.45, 131.08, 129.68, 129.20, 129.07, 128.05, 127.46, 124.99, 122.72, 122.15, 121.32, 117.01, 71.41, 45.44, 44.26, 20.54, 17.42.

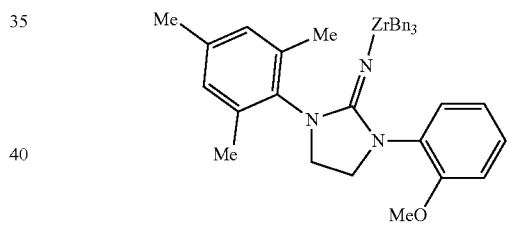

Synthesis of Tribenzyl((1-mesityl-3-(2-methoxyphenyl)imidazolidin-2-ylidene)amino)zirconium: In a nitrogen-filled glovebox, a solution of 1-mesityl-3-(2-methoxyphenyl)imidazolidin-2-imine (0.300 g, 0.970 mmol, 1 equiv.) in benzene-$d_6$ (4 mL) was added dropwise to a stirring solution of ZrBn$_4$ (0.442 g, 0.970 mmol, 1 equiv.) in benzene-$d_6$ (4 mL). The solution was stirred at room temperature for 1 h. All volatiles were removed in vacuo, yielding a thick oil. The oil was dissolved in toluene (2 mL). Hexane (15 mL) was added to the stirring toluene solution dropwise, resulting in the precipitation of a solid. The suspension was cooled in a −30° C. freezer for 16 h. The solid was filtered, washed with −30° C. hexane, and dried in vacuo to afford the product as a yellow solid (0.567 g, 87% yield). $^1$H NMR (400 MHz, Benzene-$d_6$) δ 7.31 (dd, J=7.7, 1.7 Hz, 1H), 7.04-6.96 (m, 7H), 6.89-6.79 (m, 4H), 6.76 (s, 2H), 6.54 (dd, J=8.3, 1.3 Hz, 1H), 6.29 (ddd, J=7.8, 1.6, 0.6 Hz, 6H), 3.53-3.39 (m, 2H), 3.35 (s, 3H), 3.19-3.07 (m, 2H), 2.23 (s, 6H), 2.05 (s, 3H), 1.34 (s, 6H). $^{13}$C NMR (101 MHz, Benzene-$d_6$) δ 156.05, 147.93, 142.73, 137.56, 137.34, 134.81, 130.89, 129.67, 129.57, 129.15, 128.39, 126.66, 121.44, 121.00, 111.83, 60.56, 54.98, 46.26, 44.73, 20.58, 17.60.

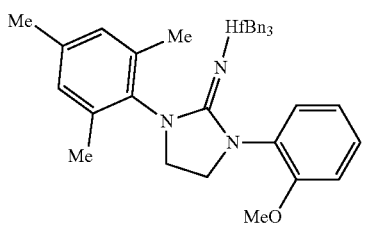

Synthesis of Tribenzyl((1-mesityl-3-(2-methoxyphenyl) imidazolidin-2-ylidene)amino)hafnium: In a nitrogen-filled glovebox, a solution of 1-mesityl-3-(2-methoxyphenyl)imidazolidin-2-imine (0.300 g, 0.970 mmol, 1 equiv.) in benzene-$d^6$ (4 mL) was added dropwise to a stirring solution of HfBn$_4$ (0.527 g, 0.970 mmol, 1 equiv.) in benzene-$d^6$ (4 mL). The solution was stirred at room temperature for 1 h. All volatiles were removed in vacuo, yielding a thick oil. The oil was dissolved in toluene (2 mL). Hexane (15 mL) was added to the stirring toluene solution dropwise, resulting in the precipitation of a solid. The suspension was cooled in a −30° C. freezer for 16 h. The solid was filtered, washed with −30° C. hexane, and dried in vacuo to afford the product as an off-white solid (0.626 g, 85% yield). $^1$H NMR (400 MHz, Benzene-$d_6$) δ 7.27 (dd, J=7.7, 1.7 Hz, 1H), 7.07-6.96 (m, 7H), 6.89-6.78 (m, 4H), 6.77-6.73 (m, 2H), 6.54 (dd, J=8.3, 1.3 Hz, 1H), 6.42 (ddd, J=7.8, 1.6, 0.7 Hz, 6H), 3.53-3.40 (m, 2H), 3.34 (s, 3H), 3.19-3.08 (m, 2H), 2.21 (d, J=0.6 Hz, 6H), 2.05 (s, 3H), 1.21 (s, 6H). $^{13}$C NMR (101 MHz, Benzene-$d_6$) δ 155.94, 151.11, 142.77, 137.53, 137.35, 134.76, 130.80, 129.48, 129.13, 129.10, 128.25, 127.39, 121.92, 121.02, 111.79, 70.76, 54.95, 45.98, 44.50, 20.58, 17.58.

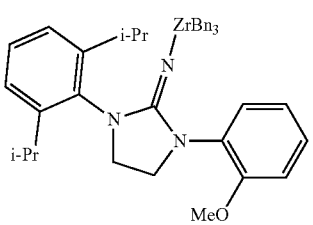

Synthesis of Tribenzyl((1-(2,6-diisopropylphenyl)-3-(2-methoxyphenyl)imidazolidin-2-ylidene)amino)zirconium: In a nitrogen-filled glovebox, a solution of 1-(2,6-diisopropylphenyl)-3-(2-methoxyphenyl)imidazolidin-2-imine (0.300 g, 0.854 mmol, 1 equiv.) in benzene-$d^6$ (4 mL) was added dropwise to a stirring solution of ZrBn$_4$ (0.389 g, 0.854 mmol, 1 equiv.) in benzene-$d^6$ (4 mL). The solution was stirred at room temperature for 1 h. All volatiles were removed in vacuo, yielding a thick oil. The oil was dissolved in toluene (2 mL). Hexane (15 mL) was added to the stirring toluene solution dropwise, resulting in the precipitation of a solid. The suspension was cooled in a −30° C. freezer for 16 h. The solid was filtered, washed with −30° C. hexane, and dried in vacuo to afford the product as a yellow solid (0.509 g, 83% yield). Contains <10% of a dibenzyl derivative, presumably LZrClBn$_2$. $^1$H NMR (400 MHz, Benzene-$d_6$) δ 7.30 (dd, J=7.7, 1.7 Hz, 1H), 7.15-6.92 (m, 10H), 6.87-6.76 (m, 4H), 6.52 (dd, J=8.3, 1.3 Hz, 1H), 6.35-6.27 (m, 6H), 3.49-3.42 (m, 2H), 3.36 (s, 3H), 3.35-3.31 (m, 2H), 3.25 (hept, J=7.2, 6.8 Hz, 2H), 1.34 (d, J=6.8 Hz, 6H), 1.31 (s, 6H), 1.15 (d, J=6.9 Hz, 6H). $^{13}$C NMR (101 MHz, Benzene-$d_6$) δ 156.10, 149.05, 148.21, 142.65, 134.84, 131.23, 129.64, 129.61, 128.84, 128.60, 126.85, 124.03, 121.52, 120.97, 111.70, 61.26, 54.95, 47.39, 46.31, 28.44, 24.96, 24.16.

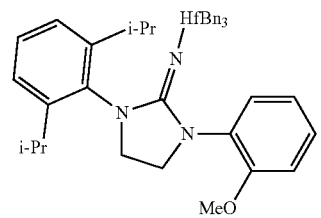

Synthesis of Tribenzyl((1-(2,6-diisopropylphenyl)-3-(2-methoxyphenyl)imidazolidin-2-ylidene)amino)hafnium: In a nitrogen-filled glovebox, a solution of 1-(2,6-diisopropylphenyl)-3-(2-methoxyphenyl)imidazolidin-2-imine (0.300 g, 0.854 mmol, 1 equiv.) in benzene-$d^6$ (4 mL) was added dropwise to a stirring solution of HfBn$_4$ (0.464 g, 0.854 mmol, 1 equiv.) in benzene-$d^6$ (4 mL). The solution was stirred at room temperature for 1 h. All volatiles were removed in vacuo, yielding a thick oil. The oil was dissolved in toluene (2 mL). Hexane (15 mL) was added to the stirring toluene solution dropwise, resulting in the precipitation of a solid. The suspension was cooled in a −30° C. freezer for 16 h. The solid was filtered, washed with −30° C. hexane, and dried in vacuo to afford the product as a white solid (0.535 g, 78% yield). Contains <10% of a dibenzyl derivative, presumably LZrClBn$_2$. $^1$H NMR (400 MHz, Benzene-$d_6$) δ 7.26 (dd, J=7.7, 1.7 Hz, 1H), 7.18-6.96 (m, 10H), 6.89-6.83 (m, 3H), 6.79 (td, J=7.6, 1.3 Hz, 1H), 6.52 (dd, J=8.3, 1.3 Hz, 1H), 6.43 (ddd, J=7.7, 1.5, 0.6 Hz, 6H), 3.51-3.43 (m, 2H), 3.35 (s, 3H), 3.39-3.30 (m, 2H), 3.23 (hept, J=7.0 Hz, 2H), 1.32 (d, J=6.8 Hz, 6H), 1.18 (s, 6H), 1.15 (d, J=6.9 Hz, 6H). $^{13}$C NMR (101 MHz, Benzene-$d_6$) δ 156.05, 152.33, 148.19, 142.79, 134.80, 131.21, 129.54, 129.08, 128.86, 128.52, 127.49, 124.04, 121.93, 121.00, 111.67, 71.82, 54.92, 47.18, 46.00, 28.43, 24.84, 24.26.

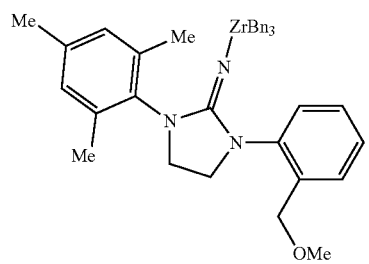

Synthesis of Tribenzyl((1-mesityl-3-(2-(methoxymethyl) phenyl)imidazolidin-2-ylidene)amino)zirconium: In a nitrogen-filled glovebox, a solution of 1-mesityl-3-(2-(methoxymethyl)phenyl)imidazolidin-2-imine (0.300 g, 0.928 mmol, 1 equiv.) in benzene-$d^6$ (4 mL) was added to a solution of ZrBn$_4$ (0.423 g, 0.928 mmol, 1 equiv.) in benzene-$d^6$ (4 ml). The solution was stirred at room temperature for 1 hour. As a small amount of solid material had precipitated, the solution was filtered and concentrated in vacuo to yield a thick yellow oil. The material was dissolved in toluene (2 mL). While stirring, hexanes (17 mL) was added, producing a cloudy yellow solution. The solution was cooled in a −30° C. freezer for 2 h, resulting in the separation of an oil. Vigorous shaking and stirring of the material resulted in the precipitation of a yellow solid, however some product still remained in the thick goo layer. The suspension was stored in a −30° C. freezer for 1 h. The material was filtered, washed with cold hexanes, and dried in vacuo to yield the product as a yellow solid (0.364 g, 57% yield). The material remaining in the thick goo was dissolved in toluene (1 mL). Hexanes (10 mL) was added to the stirring toluene solution, resulting in the formation of a hazy yellow solution. The vial was stored in a −30° C. freezer for 18 h, resulting in the precipitation of a yellow solid. The solid was filtered, washed with cold (−30° C.) hexanes, and dried in vacuo to afford an additional crop of product (0.108 g, 17% yield), which was spectroscopically identical to the first crop. Combined: 0.472 g, 74% yield. $^1$H NMR (400 MHz, Benzene-$d_6$) δ 7.46-7.41 (m, 1H), 7.10 (ddd, J=8.6, 6.2, 1.7 Hz, 1H), 7.06-7.01 (m, 2H), 7.00-6.94 (m, 6H), 6.87-6.81 (m, 3H), 6.75 (s, 2H), 6.26-6.21 (m, 6H), 4.60 (s, 2H), 3.36-3.27 (m, 2H), 3.22 (s, 3H), 3.13-3.02 (m, 2H), 2.23 (s, 6H), 2.05 (s, 3H), 1.28 (s, 6H). $^{13}$C NMR (101 MHz, Benzene-$d_6$) δ 147.43, 142.44, 139.31, 137.69, 137.43, 137.14, 134.64, 129.70, 129.64, 129.26, 128.74, 128.27, 127.60, 126.68, 121.60, 71.54, 60.65, 57.95, 47.63, 44.77, 20.59, 17.63.

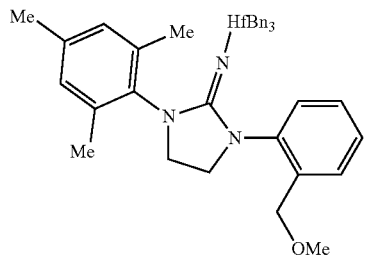

Synthesis of Tribenzyl((1-mesityl-3-(2-(methoxymethyl)phenyl)imidazolidin-2-ylidene)amino)hafnium: In a nitrogen-filled glovebox, a solution of 1-mesityl-3-(2-(methoxymethyl)phenyl)imidazolidin-2-imine (0.300 g, 0.928 mmol, 1 equiv.) in benzene-$d^6$ (4 mL) was added to a solution of HfBn$_4$ (0.504 g, 0.928 mmol, 1 equiv.) in benzene-$d^6$ (4 ml). The solution was stirred at room temperature for 1 hour. As a small amount of solid material had precipitated, the solution was filtered and concentrated in vacuo to yield a thick yellow oil. The material was mostly dissolved in toluene (2 mL). While stirring, hexanes (17 mL) was added, producing a cloudy off-white solution. The suspension was cooled in a −30° C. freezer for 1 h. The material was filtered, washed with cold hexanes, and dried in vacuo to yield the product as an off-white solid (0.677 g, 94% yield). $^1$H NMR (400 MHz, Benzene-$d_6$) δ 7.43-7.38 (m, 1H), 7.13-6.93 (m, 9H), 6.89-6.79 (m, 3H), 6.76 (s, 2H), 6.40-6.34 (m, 6H), 4.55 (s, 2H), 3.37-3.26 (m, 2H), 3.20 (s, 3H), 3.13-3.01 (m, 2H), 2.21 (s, 6H), 2.06 (s, 3H), 1.17 (s, 6H). $^{13}$C NMR (101 MHz, Benzene-$d_6$) δ 150.68, 142.67, 139.38, 137.66, 137.14, 137.11, 134.58, 129.78, 129.24, 129.09, 128.83, 128.09, 127.45, 127.40, 122.00, 71.64, 71.03, 58.06, 47.38, 44.55, 20.58, 17.60.

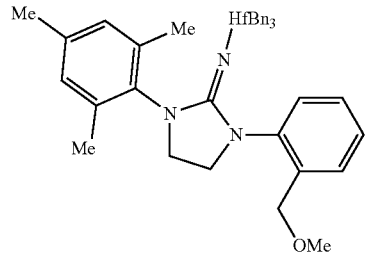

Synthesis of Tribenzyl((1-mesityl-3-(2-(methoxymethyl)phenyl)imidazolidin-2-ylidene)amino)hafnium: In a nitrogen-filled glovebox, a solution of 1-mesityl-3-(2-(methoxymethyl)phenyl)imidazolidin-2-imine (0.300 g, 0.928 mmol, 1 equiv.) in benzene-$d^6$ (4 mL) was added to a solution of HfBn$_4$ (0.504 g, 0.928 mmol, 1 equiv.) in benzene-$d^6$ (4 ml). The solution was stirred at room temperature for 1 hour. As a small amount of solid material had precipitated, the solution was filtered and concentrated in vacuo to yield a thick yellow oil. The material was mostly dissolved in toluene (2 mL). While stirring, hexanes (17 mL) was added, producing a cloudy off-white solution. The suspension was cooled in a −30° C. freezer for 1 h. The material was filtered, washed with cold hexanes, and dried in vacuo to yield the product as an off-white solid (0.677 g, 94% yield). $^1$H NMR (400 MHz, Benzene-$d_6$) δ 7.43-7.38 (m, 1H), 7.13-6.93 (m, 9H), 6.89-6.79 (m, 3H), 6.76 (s, 2H), 6.40-6.34 (m, 6H), 4.55 (s, 2H), 3.37-3.26 (m, 2H), 3.20 (s, 3H), 3.13-3.01 (m, 2H), 2.21 (s, 6H), 2.06 (s, 3H), 1.17 (s, 6H). $^{13}$C NMR (101 MHz, Benzene-$d_6$) δ 150.68, 142.67, 139.38, 137.66, 137.14, 137.11, 134.58, 129.78, 129.24, 129.09, 128.83, 128.09, 127.45, 127.40, 122.00, 71.64, 71.03, 58.06, 47.38, 44.55, 20.58, 17.60.

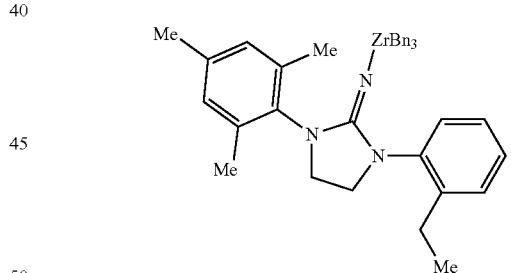

Synthesis of Tribenzyl((1-(2-ethylphenyl)-3-mesitylimidazolidin-2-ylidene)amino)zirconium: In a nitrogen-filled glovebox, a solution of 1-(2-ethylphenyl)-3-mesitylimidazolidin-2-imine (0.300 g, 0.976 mmol, 1 equiv.) in benzene-$d^6$ (4 mL) was added to a solution of ZrBn$_4$ (0.445 g, 0.976 mmol, 1 equiv.) in benzene-$d^6$ (4 ml). The solution was stirred at room temperature for 1 hour. The solution was passed through a syringe filter and concentrated in vacuo to yield a yellow oil. The oil was dissolved in toluene (2 mL). Hexane (17 mL) was added to the stirring toluene solution dropwise, producing a solution with some precipitate. The mixture was stored in a −30° C. freezer for 17 h, resulting in the precipitation of fine yellow crystals. The cold solution was stirred briefly to aid in the precipitation of additional material, then stored in a −30° C. freezer for 2 h. The mixture was filtered, washed with cold hexane, and dried in vacuo to yield the product as a yellow solid (0.552 g, 84% yield). $^1$H NMR (400 MHz, Benzene-d$_6$) δ 7.11-6.94 (m, 10H), 6.87-6.81 (m, 3H), 6.77-6.73 (m, 2H), 6.27-6.20 (m, 6H), 3.24-3.12 (m, 2H), 3.04 (dd, J=9.5, 6.8 Hz, 2H), 2.69 (q, J=7.6 Hz, 2H), 2.22 (s, 6H), 2.06 (s, 3H), 1.28 (s, 6H), 1.22 (t, J=7.6 Hz, 3H). $^{13}$C NMR (101 MHz, Benzene-d$_6$) δ 147.74, 142.79, 142.52, 139.21, 137.66, 137.14, 134.67, 129.68, 129.25, 129.09, 128.54, 127.95, 127.08, 126.67, 121.54, 60.61, 47.53, 44.66, 24.66, 20.59, 17.60, 14.81.

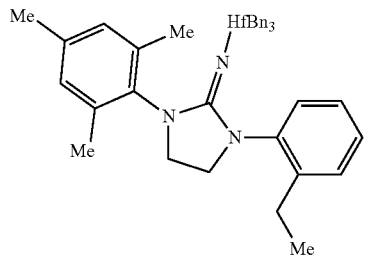

Synthesis of Tribenzyl((1-(2-ethylphenyl)-3-mesitylimidazolidin-2-ylidene)amino)hafnium: In a nitrogen-filled glovebox, a solution of 1-(2-ethylphenyl)-3-mesitylimidazolidin-2-imine (0.300 g, 0.976 mmol, 1 equiv.) in benzene-d$^6$ (4 mL) was added to a solution of HfBn$_4$ (0.530 g, 0.976 mmol, 1 equiv.) in benzene-d$^6$ (4 ml). The solution was stirred at room temperature for 1 hour. The solution was passed through a syringe filter and concentrated in vacuo to yield a pale yellow oil. The oil was dissolved in toluene (2 mL). Hexane (17 mL) was added to the stirring toluene solution dropwise, producing a solution with some precipitate. The mixture was stored in a −30° C. freezer for 17 h, resulting in the precipitation of a white powder. The cold solution was stirred briefly to aid in the precipitation of additional material, then stored in a −30° C. freezer for 2 h. The mixture was filtered, washed with cold hexane, and dried in vacuo to yield the product as a white powder (0.561 g, 76% yield). $^1$H NMR (400 MHz, Benzene-d$_6$) δ 7.12-6.92 (m, 10H), 6.89-6.82 (m, 3H), 6.76 (s, 2H), 6.43-6.28 (m, 6H), 3.21-3.14 (m, 2H), 3.09-2.99 (m, 2H), 2.67 (q, J=7.6 Hz, 2H), 2.20 (s, 6H), 2.06 (s, 3H), 1.21 (t, J=7.6 Hz, 3H), 1.15 (s, 6H). $^{13}$C NMR (101 MHz, Benzene-d$_6$) δ 151.03, 142.75, 142.58, 139.16, 137.63, 137.14, 134.61, 129.22, 129.11, 129.06, 128.55, 127.91, 127.40, 127.12, 122.01, 70.78, 47.33, 44.45, 24.65, 20.58, 17.56, 14.87.

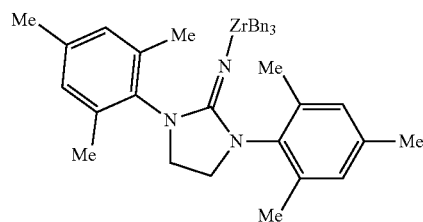

Synthesis of Tribenzyl((1,3-dimesitylimidazolidin-2-ylidene)amino)zirconium: In a nitrogen-filled glovebox, a solution of 1,3-dimesitylimidazolidin-2-imine (0.120 g, 0.373 mmol, 1 equiv.) in benzene-d$^6$ (1.5 mL) was added to a solution of ZrBn$_4$ (0.170 g, 0.373 mmol, 1 equiv.) in benzene-d$^6$ (1.5 ml). The solution was stirred at room temperature for 1 hour. The solution was concentrated in vacuo to yield a thick yellow oil. The oil was dissolved in toluene (0.75 mL), layered with hexane (6 mL), and stored in a −30° C. freezer, resulting in the precipitation of a solid. The material was filtered, washed with cold hexanes, and dried in vacuo to yield the product as a yellow solid (0.187 g, 73% yield). $^1$H NMR (400 MHz, Benzene-d$_6$) δ 6.97 (dd, J=8.1, 7.0 Hz, 6H), 6.87-6.80 (m, 3H), 6.77 (s, 4H), 6.27-6.15 (m, 6H), 3.09 (s, 4H), 2.24 (s, 12H), 2.05 (s, 6H), 1.26 (s, 6H). $^{13}$C NMR (101 MHz, Benzene-d$_6$) δ 146.75, 142.47, 137.64, 137.21, 134.53, 129.70, 129.25, 126.58, 121.49, 59.62, 44.50, 20.60, 17.62.

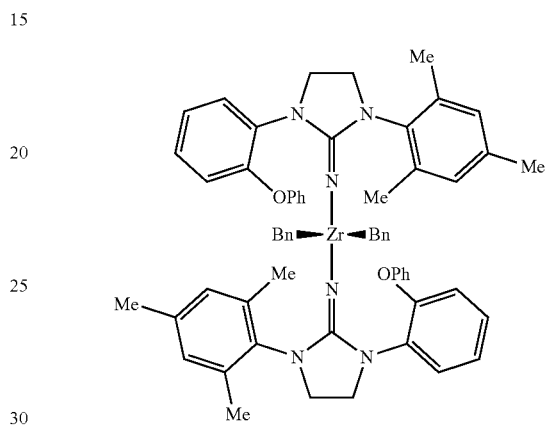

Synthesis of Dibenzyl[bis-((1-mesityl-3-(2-phenoxyphenyl)imidazolidin-2-ylidene)amino)]zirconium: In a nitrogen-filled glovebox, a solution of 1-mesityl-3-(2-phenoxyphenyl)imidazolidin-2-imine (50 mg, 0.135 mmol, 1 equiv.) in toluene-d$^8$ (2 mL) was added dropwise to a stirring solution of tribenzyl((1-mesityl-3-(2-phenoxyphenyl)imidazolidin-2-ylidene)amino)zirconium (99 mg, 0.135 mmol, 1 equiv.) in toluene-d$^8$ (2 mL). The reaction was allowed to stir 50° C. for 15 hours. The yellow solution was concentrated in vacuo, yielding a thick yellow oil. The material was redissolved in toluene (0.5 mL), layered with hexane (10 mL), and stored in a −30° C. freezer for 3 days. The material was filtered, washed with minimal −30° C. hexanes, and dried in vacuo to afford the product as an off-white solid (70 mg, 51% yield). NMR spectra were complex and showed evidence of multiple isomers, oligomers, or loss of molecular symmetry as apparent from the multiple mesityl methyl peaks.

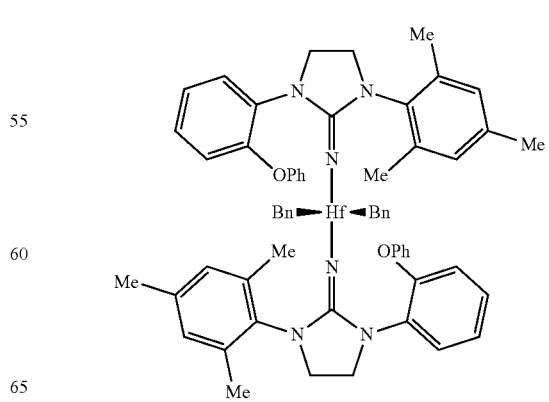

Synthesis of Dibenzyl[bis-((1-mesityl-3-(2-phenoxyphenyl)imidazolidin-2-ylidene)amino)]hafnium: In a nitrogen-filled glovebox, a solution of 1-mesityl-3-(2-phenoxyphenyl)imidazolidin-2-imine (50 mg, 0.135 mmol, 1 equiv.) in toluene-d$^8$ (2 mL) was added dropwise to a stirring solution of tribenzyl((1-mesityl-3-(2-phenoxyphenyl)imidazolidin-2-ylidene)amino)hafnium (111 mg, 0.135 mmol, 1 equiv.) in toluene-d$^8$ (2 mL). The reaction was allowed to stir 50° C. for 15 hours. The yellow solution was concentrated in vacuo, yielding a thick yellow oil. The material was redissolved in toluene (0.5 mL), layered with hexane (10 mL), and stored in a –30° C. freezer for 3 days. The material was filtered, washed with minimal –30° C. hexanes, and dried in vacuo to afford the product as an off-white solid. Yield was low so another crop was obtained by concentrating the filtrate in vacuo, layering with hexane (5 mL), and storing in a –30° C. for 16 h. The material was filtered, washed with minimal –30° C. hexanes, and dried in vacuo to afford the product as an off-white solid. Combined yield 55 mg, 37%. NMR spectra were complex and showed evidence of multiple isomers, oligomers, or loss of molecular symmetry as apparent from the multiple mesityl methyl peaks.

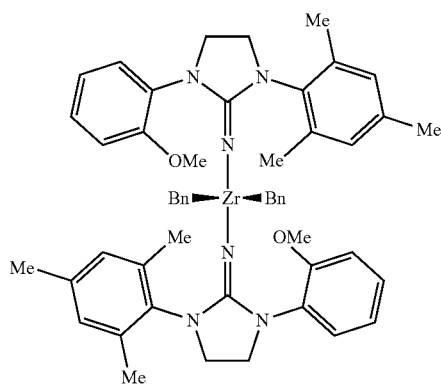

Synthesis of Dibenzyl(bis(1-mesityl-3-(2-methoxyphenyl)imidazolidin-2-ylidene)amino)zirconium: In a nitrogen-filled glovebox, a solution of 1-mesityl-3-(2-methoxyphenyl)imidazolidin-2-imine (46 mg, 0.149 mmol, 1 equiv.) in toluene-d$^8$ (0.5 mL) was added dropwise to a stirring solution of tribenzyl((1-mesityl-3-(2-methoxyphenyl)imidazolidin-2-ylidene)amino)zirconium (100 mg, 0.149 mmol, 1 equiv.) in toluene-d$^8$ (0.5 mL) at 100° C. The ligand solution vial was rinsed with toluene-d$^8$ (0.5 mL), and this was also added to the stirring reaction The reaction was allowed to stir 100° C. for 62 hours. The solution was allowed to cool to room temperature and concentrated in vacuo, yielding a thick oil. The material was dissolved in toluene (0.3 mL), layered with hexane (3 mL), and stored in a –30° C. freezer for 2 days, resulting in the precipitation of a powder. The material was filtered, washed with minimal –30° C. hexanes, and dried in vacuo to afford the product as an orange solid (63 mg, 48% yield). NMR spectra were complex and showed evidence of multiple isomers, oligomers, or loss of molecular symmetry as apparent from the multiple mesityl methyl peaks.

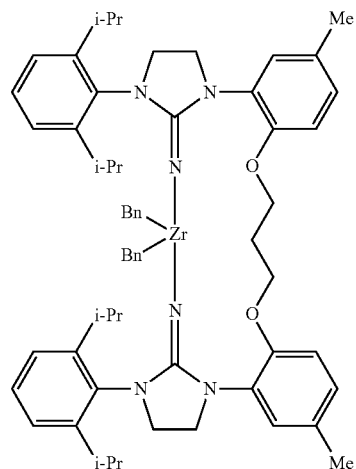

Synthesis of Dibenzyl(3,3'-((propane-1,3-diylbis(oxy))bis(5-methyl-2,1-phenylene))bis(1-(2,6-diisopropylphenyl)imidazolidin-2-amino)zirconium: In a nitrogen-filled glovebox, a solution of ZrBn$_4$ (55 mg, 0.121 mmol, 1 equiv.) in toluene-d$^8$ (2 mL) was added dropwise over several minutes to a stirring solution of 3,3'-((propane-1,3-diylbis(oxy))bis(5-methyl-2,1-phenylene))bis(1-(2,6-diisopropylphenyl)imidazolidin-2-imine) (100 mg, 0.121 mmol, 1 equiv.) in toluene-d$^8$ (2 mL) at 100° C. The solution was allowed to stir at 100° C. for 18 h. The reaction was stirred at 100° C. for an additional 18 h, however little change was observed from the previous spectrum. The solution was passed through a syringe filter, and all volatiles were removed in vacuo to yield a thick oil. The oil was dissolved in toluene (0.3 mL), layered with hexane (3 mL), and stored in a –30 C freezer for 2 days. The precipitated solid was filtered, washed with cold hexane, and dried in vacuo to yield the product as a beige solid (65 mg, 53% yield). NMR spectra were complex and showed evidence of multiple isomers, oligomers, or loss of molecular symmetry.

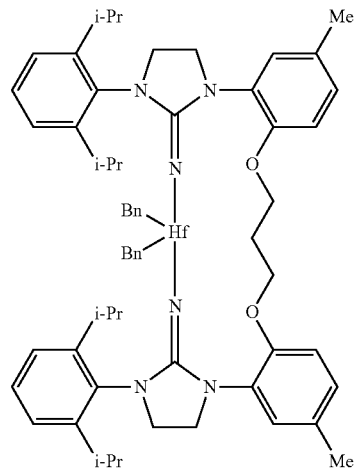

Synthesis of Dibenzyl(3,3'-((propane-1,3-diylbis(oxy))bis(5-methyl-2,1-phenylene))bis(1-(2,6-diisopropylphenyl)

imidazolidin-2-amino)hafnium: In a nitrogen-filled glovebox, a solution of 3,3'-((propane-1,3-diylbis(oxy))bis(5-methyl-2,1-phenylene))bis(1-(2,6-diisopropylphenyl)imidazolidin-2-imine) (0.500 g, 0.603 mmol, 1 equiv.) in toluene (2.5 mL) was added to a solution of HfBn$_4$ (0.327 g, 0.603 mmol, 1 equiv.) in toluene (2.5 mL). Soon after addition, a powder precipitated from solution. The reaction was stirred at room temperature for 90 h. The suspension was filtered, washed with toluene (4×5 mL), and concentrated in vacuo to yield a thick brown oil. The oil was dissolved in toluene (2 mL), layered with hexanes (18 mL), and stored in a −30° C. freezer for 18 h, resulting in the precipitation of a solid. The material was filtered, washed with cold hexanes, and dried in vacuo to yield the product as a white solid (0.386 g, 58% yield). NMR spectra were complex and showed evidence of multiple isomers, oligomers, or loss of molecular symmetry.

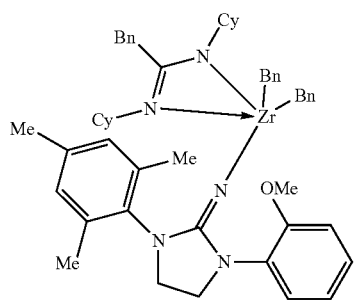

Synthesis of Dibenyl(1-mesityl-3-(2-methoxyphenyl)imidazolidin-2-ylidene)amino))(cyclohexyl(1-(cyclohexylimino)-2-phenylethyl)amido)zirconium: In a nitrogen-filled glovebox, a solution of DCC (31 mg, 0.149 mmol, 1 equiv.) in benzene-d$^6$ (0.7 mL) was added to a solution of tribenzyl((1-mesityl-3-(2-methoxyphenyl)imidazolidin-2-ylidene)amino)zirconium (100 mg, 0.147 mmol, 1 equiv.) in benzene-d$^6$ (0.7 mL). The reaction was stirred at room temperature for 2 h. Multiple isomers appear to be present, however there is a clear major isomer (>80%). All volatiles were removed in vacuo, yielding a thick oil. The material was dissolved in toluene (0.5 mL), layered with hexanes (4 mL) and stored in a −30° C. freezer for 64 hours, yielding a crystalline solid. The material was filtered, washed with cold (−30° C.) hexanes, and dried in vacuo to yield the product as a pale yellow solid (84.5 mg, 65% yield). $^1$H NMR (400 MHz, Benzene-d$_6$) δ 7.84 (dd, J=7.8, 1.8 Hz, 1H), 7.25-6.83 (m, 17H), 6.75 (s, 2H), 6.55 (dd, J=8.2, 1.4 Hz, 1H), 3.67-3.59 (m, 2H), 3.45 (s, 2H), 3.37 (s, 3H), 3.24-3.16 (m, 2H), 2.90 (tt, J=10.8, 4.4 Hz, 2H), 2.25 (s, 6H), 2.25 (d, J=10.3 Hz, 2H), 2.06 (s, 3H), 1.80 (d, J=10.3 Hz, 2H), 1.61-0.92 (m, 20H). $^{13}$C NMR (101 MHz, Benzene-d$_6$) δ 176.37, 154.93, 147.80, 145.71, 137.04, 136.86, 136.21, 135.06, 130.24, 129.06, 128.87, 128.62, 127.99, 127.86, 127.28, 126.80, 126.30, 120.71, 119.95, 111.52, 66.28, 56.73, 54.63, 45.96, 44.73, 34.83, 31.17, 25.96, 25.37, 20.62, 18.23.

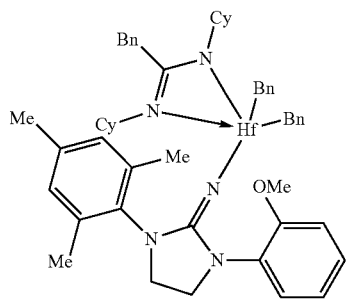

Synthesis of Dibenzyl(1-mesityl-3-(2-methoxyphenyl)imidazolidin-2-ylidene)amino))(cyclohexyl(1-(cyclohexylimino)-2-phenylethyl)amido)hafnium: In a nitrogen-filled glovebox, a solution of DCC (27 mg, 0.132 mmol, 1 equiv.) in benzene-d$^6$ (0.7 mL) was added to a solution of tribenzyl ((1-mesityl-3-(2-methoxyphenyl)imidazolidin-2-ylidene) amino)hafnium (100 mg, 0.132 mmol, 1 equiv.) in benzene-d$^6$ (0.7 mL). The reaction was stirred at room temperature for 17 h. All volatiles were removed in vacuo, yielding a thick oil. The material was dissolved in toluene (0.4 mL), layered with hexanes (4 mL) and stored in a −30° C. freezer for 17 hours, resulting in the precipitation of a solid. The material was filtered, washed with cold (−30° C.) hexanes, and dried in vacuo to yield the product as a white solid (65 mg, 51% yield). $^1$H NMR (400 MHz, Benzene-d$_6$) δ 7.79 (dd, J=7.7, 1.8 Hz, 1H), 7.28-7.22 (m, 4H), 7.18-7.05 (m, 6H), 7.03-6.94 (m, 4H), 6.93-6.86 (m, 3H), 6.75 (s, 2H), 6.55 (dd, J=8.2, 1.4 Hz, 1H), 3.68-3.59 (m, 2H), 3.41 (s, 2H), 3.36 (s, 3H), 3.24-3.15 (m, 2H), 3.05 (ddd, J=10.9, 6.6, 4.3 Hz, 2H), 2.23 (s, 6H), 2.07 (s, 3H), 1.96 (d, J=11.2 Hz, 2H), 1.58 (d, J=11.2 Hz, 2H), 1.56-0.88 (m, 20H). $^{13}$C NMR (101 MHz, Benzene-d$_6$) δ 176.26, 154.91, 149.02, 148.43, 137.09, 136.69, 135.91, 135.08, 130.24, 129.02, 128.98, 128.67, 127.93, 127.75, 127.54, 126.66, 126.40, 120.77, 120.16, 111.43, 74.07, 56.52, 54.61, 45.71, 44.48, 34.66, 31.39, 25.93, 25.28, 20.65, 18.22.

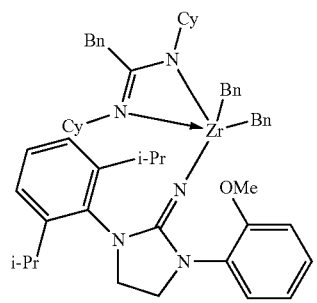

Synthesis of Dibenzyl((1-(2,6-diisopropylphenyl)-3-(2-methoxyphenyl)imidazolidin-2-ylidene)amino)(cyclohexyl (1-(cyclohexylimino)-2-phenylethyl)amido)zirconium: In a nitrogen-filled glovebox, a solution of DCC (29 mg, 0.140 mmol, 1 equiv.) in benzene-d$^6$ (0.7 mL) was added to a solution of tribenzyl((1-(2,6-diisopropylphenyl)-3-(2-methoxyphenyl)imidazolidin-2-ylidene)amino)zirconium (100 mg, 0.140 mmol, 1 equiv.) in benzene-d$^6$ (0.7 mL). The reaction was stirred at room temperature for 17 h. All volatiles were removed in vacuo, yielding a thick oil. The material was dissolved in toluene (0.4 mL), layered with hexanes (4 mL) and stored in a −30° C. freezer for 15 hours, resulting in the precipitation of a solid. The material was filtered, washed with cold (−30° C.) hexanes, and dried in vacuo to yield the product as a white solid (88 mg, 68% yield). $^1$H NMR (400 MHz, Benzene-d$_6$) δ 7.73 (dd, J=7.7, 1.8 Hz, 1H), 7.27-6.78 (m, 20H), 6.51 (dd, J=8.2, 1.4 Hz, 1H), 3.65-3.58 (m, 2H), 3.53-3.42 (m, 4H), 3.41 (s, 2H), 3.36 (s, 3H), 2.83 (tt, J=11.1, 4.0 Hz, 2H), 2.16 (d, J=10.4 Hz, 2H), 1.94 (d, J=10.4 Hz, 2H), 1.38 (d, J=6.8 Hz, 6H), 1.14 (d, J=6.8 Hz, 6H), 1.55-0.88 (m, 20H). $^{13}$C NMR (101 MHz, Benzene-d$_6$) δ 175.85, 155.03, 148.07, 147.84, 147.00, 136.18, 135.36, 130.33, 130.04, 128.91, 128.57, 128.47, 128.05, 127.40, 127.28, 126.28, 124.02, 121.00, 120.20, 111.30, 65.67, 56.68, 54.67, 47.86, 46.33, 34.53, 31.53, 28.37, 25.95, 25.69, 25.36, 23.80.

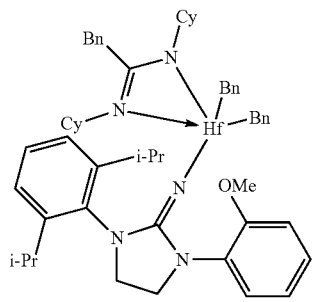

Synthesis of Dibenzyl((1-(2,6-diisopropylphenyl)-3-(2-methoxyphenyl)imidazolidin-2-ylidene)amino)(cyclohexyl(1-(cyclohexylimino)-2-phenylethyl)amido)hafnium: In a nitrogen-filled glovebox, a solution of DCC (26 mg, 0.125 mmol, 1 equiv.) in benzene-d$^6$ (0.7 mL) was added to a solution of tribenzyl((1-(2,6-diisopropylphenyl)-3-(2-methoxyphenyl)imidazolidin-2-ylidene)amino)hafnium (100 mg, 0.125 mmol, 1 equiv.) in benzene-d$^6$ (0.7 mL). The reaction was stirred at room temperature for 17 h. All volatiles were removed in vacuo, yielding a thick oil. The material was dissolved in toluene (0.4 mL), layered with hexanes (4 mL) and stored in a −30° C. freezer for 17 hours, resulting in the precipitation of a solid. The material was filtered, washed with cold (−30° C.) hexanes, and dried in vacuo to yield the product as a white solid (87 mg, 69% yield). $^1$H NMR (400 MHz, Benzene-d$_6$) δ 7.63 (dd, J=7.7, 1.8 Hz, 1H), 7.26 (dd, J=8.1, 7.1 Hz, 4H), 7.21-7.04 (m, 10H), 7.02-6.88 (m, 5H), 6.84 (td, J=7.6, 1.4 Hz, 1H), 6.51 (dd, J=8.2, 1.3 Hz, 1H), 3.72-3.57 (m, 2H), 3.51-3.41 (m, 4H), 3.39 (s, 2H), 3.36 (s, 3H), 2.97 (tt, J=11.1, 4.1 Hz, 2H), 1.84 (d, J=11.4 Hz, 2H), 1.71 (d, J=11.4 Hz, 2H), 1.36 (d, J=6.8 Hz, 6H), 1.15 (d, J=6.8 Hz, 6H), 1.53-0.89 (m, 20H). $^{13}$C NMR (101 MHz, Benzene-d$_6$) δ 175.45, 155.23, 150.50, 148.61, 148.17, 135.90, 135.42, 130.54, 130.18, 128.91, 128.59, 128.31, 128.06, 127.76, 127.72, 126.36, 123.95, 121.15, 120.37, 111.23, 73.80, 56.47, 54.71, 45.99, 34.33, 31.70, 28.33, 25.92, 25.63, 25.32, 23.80.

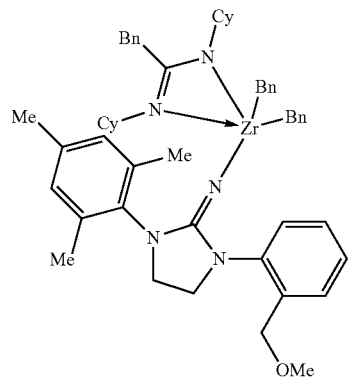

Synthesis of Dibenzyl((1-mesityl-3-(2-(methoxymethyl)phenyl)imidazolidin-2-ylidene)amino)(cyclohexyl(1-(cyclohexylimino)-2-phenylethyl)amido)zirconium: In a nitrogen-filled glovebox, a solution of DCC (30 mg, 0.146 mmol, 1 equiv.) in benzene-d$^6$ (0.7 mL) was added to a solution of tribenzyl((1-mesityl-3-(2-(methoxymethyl)phenyl)imidazolidin-2-ylidene)amino)zirconium (100 mg, 0.146 mmol, 1 equiv.) in benzene-d$^6$ (0.7 mL). The reaction was stirred at room temperature for 18 h. All volatiles were removed in vacuo, yielding a thick oil. Hexamethyldisiloxane (4 mL) was added, and the mixture was vigorously stirred for 3 h. The resulting suspension was stored in a −30° C. freezer for 16 h, resulting in the precipitation of a yellow solid. The material was filtered, washed with cold (−30° C.) hexanes, and dried in vacuo to yield the product as a yellow solid (42 mg, 32% yield). Material contained approximately 0.3 equiv. of hexamethyldisiloxane. $^1$H NMR (400 MHz, Benzene-d$_6$) δ 7.38 (d, J=6.9 Hz, 1H), 7.32 (d, J=7.7 Hz, 1H), 7.24-7.06 (m, 11H), 7.03-6.96 (m, 4H), 6.89 (t, J=7.2 Hz, 2H), 6.77 (s, 2H), 4.62 (s, 2H), 3.46-3.40 (m, 4H), 3.25 (s, 3H), 3.19-3.12 (m, 2H), 2.94-2.82 (m, 2H), 2.28 (s, 6H), 2.13 (d, J=10.4 Hz, 2H), 2.08 (s, 3H), 1.83 (d, J=10.5 Hz, 2H), 1.63-0.87 (m, 20H). $^{13}$C NMR (101 MHz, Benzene-d$_6$) δ 176.30, 148.64, 145.46, 140.25, 137.01, 136.85, 136.27, 135.58, 134.96, 130.23, 129.22, 128.61, 128.56, 127.92 (2 carbons), 127.09, 126.72, 126.29, 126.12, 119.85, 72.22, 66.14, 58.30, 56.77, 47.84, 44.75, 34.76, 31.40, 25.90, 25.33, 20.62, 18.31.

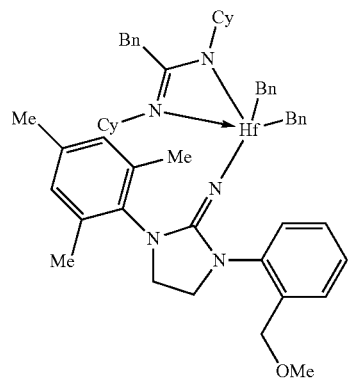

Synthesis of Dibenzyl((1-mesityl-3-(2-(methoxymethyl)phenyl)imidazolidin-2-ylidene)amino)(cyclohexyl(1-(cyclohexylimino)-2-phenylethyl)amido)hafnium: In a nitrogen-filled glovebox, a solution of DCC (27 mg, 0.129 mmol, 1 equiv.) in benzene-d$^6$ (0.7 mL) was added to a solution of tribenzyl((1-mesityl-3-(2-(methoxymethyl)phenyl)imidazo-lidin-2-ylidene)amino)hafnium (CS-255) (100 mg, 0.129 mmol, 1 equiv.) in benzene-d$^6$ (0.7 mL). The reaction was stirred at room temperature for 18 h. All volatiles were removed in vacuo, yielding a thick oil. The material was dissolved in toluene (0.2 mL) and hexanes (4 mL) was added dropwise. The vial was stored in a −30° C. freezer for 6 days, resulting in the precipitation of a white powder. The material was filtered, washed with cold (−30° C.) hexanes, and dried in vacuo to yield the product as a white solid (63 mg, 50% yield). $^1$H NMR (400 MHz, Benzene-d$_6$) δ 7.36 (dd, J=7.7, 1.6 Hz, 1H), 7.28-7.20 (m, 5H), 7.17-7.06 (m, 8H), 7.01-6.94 (m, 3H), 6.88 (t, J=7.3 Hz, 2H), 6.78 (s, 2H), 4.59 (s, 2H), 3.50-3.38 (m, 4H), 3.27 (s, 3H), 3.16 (t, J=7.9 Hz, 2H), 3.09-2.95 (m, 2H), 2.27 (s, 6H), 2.09 (s, 3H), 1.84 (d, J=11.3 Hz, 2H), 1.61 (d, J=11.3 Hz, 2H), 1.56-0.84 (m, 20H). $^{13}$C NMR (101 MHz, Benzene-d$_6$) δ 175.98, 149.51, 148.55, 140.36, 136.92 (2 carbons), 136.05, 135.22, 135.07, 130.27, 129.19, 128.62 (2 carbons), 127.92, 127.60, 127.33, 126.38, 126.35, 125.83, 119.98, 73.06, 72.49, 58.46, 56.58, 47.51, 44.52, 34.66, 31.69, 25.88, 25.28, 20.63, 18.28.

Polymerization results are presented in Tables 2-24, below. In these tables, "Metal" refers to the metal-containing precursor that reacts with the ligand to form the metal-ligand complex; "Metal (μmol)" refers to the amount of the metal-containing precursor in micromoles; "Co-catalyst" refers to the identity of the co-catalyst, which is either tetrakis(pentafluorophenyl)borate(1-)amine ("RIBS-2") or tris(pentafluorophenyl)borane (FAB); "Co-Catalyst (μmol)" refers to the amount of the co-catalyst in micromoles; "Ligand (μmol)" refers to the amount of ligand in micromoles; "L:M" is the molar ratio of ligand to metal; "MMAO (μmol)" refers to the amount of modified methylalumoxane in micromoles; "octene (mol %)" refers to the amount of octene expressed in mole percent based to the total moles of ethylene and octene; "Mn" refers to the number average molecular weight in grams/mole; "Mw" refers to the weight average molecular weight in grams/mole; "MWD" is the molecular weight dispersity (ratio of weight average molecular weight to number average molecular weight).

TABLE 2

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| Zr(Bn)$_4$ | 0.1 | RIBS-II | 0.15 | 0.1 | 1:1 | 0.5 | 7.9 | 287 | 27469 | 95.71 |
| Zr(Bn)$_4$ | 0.1 | RIBS-II | 0.15 | 0.1 | 1:1 | 0.5 | 7.7 | 240 | 16043 | 66.85 |
| Zr(Bn)$_4$ | 0.1 | RIBS-II | 0.15 | 0.1 | 1:1 | 0.5 | 8.3 | 223 | 9821 | 44.04 |
| Zr(Bn)$_4$ | 0.1 | RIBS-II | 0.15 | 0.1 | 1:1 | 0.5 | 9.9 | 239 | 2311 | 9.67 |
| Hf(Bn)$_4$ | 0.1 | RIBS-II | 0.15 | 0.1 | 1:1 | 0.5 | 10.0 | 4085 | 251255 | 61.51 |
| Hf(Bn)$_4$ | 0.1 | RIBS-II | 0.15 | 0.1 | 1:1 | 0.5 | 12.3 | 3429 | 105746 | 30.84 |
| Zr(Bn)$_4$ | 0.1 | RIBS-II | 0.15 | 0.2 | 2:1 | 0.5 | 7.7 | 213 | 47859 | 224.69 |
| Zr(Bn)$_4$ | 0.1 | RIBS-II | 0.15 | 0.2 | 2:1 | 0.5 | 7.7 | 211 | 44240 | 209.67 |
| Controls | | | | | | | | | | |
| Zr(Bn)$_4$ | 0.1 | RIBS-II | 0.15 | | | 0.5 | 5.0 | 4408 | 277379 | 62.93 |
| Zr(Bn)$_4$ | 0.1 | RIBS-II | 0.15 | | | 0.5 | 5.0 | 4162 | 298918 | 71.82 |

TABLE 3

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| Hf(Bn)$_4$ | 0.1 | RIBS-II | 0.15 | 0.1 | 1:1 | 0.5 | 15.3 | 2339 | 50399 | 21.55 |
| Hf(Bn)$_4$ | 0.1 | RIBS-II | 0.15 | 0.1 | 1:1 | 0.5 | 14.9 | 2495 | 71116 | 28.50 |
| Zr(Bn)$_4$ | 0.1 | RIBS-II | 0.15 | 0.1 | 1:1 | 0.5 | 7.1 | 1570 | 10407 | 6.63 |
| Zr(Bn)$_4$ | 0.1 | RIBS-II | 0.15 | 0.1 | 1:1 | 0.5 | 6.9 | 14.81 | 8209 | 5.54 |
| Hf(Bn)$_4$ | 0.1 | RIBS-II | 0.15 | 0.2 | 2:1 | 0.5 | 5.4 | 3152 | 25721 | 8.16 |
| Hf(Bn)$_4$ | 0.1 | RIBS-II | 0.15 | 0.2 | 2:1 | 0.5 | 5.5 | 2853 | 14477 | 5.07 |

TABLE 3-continued

Ligand = [2,6-diisopropylphenyl imidazolidin-2-imine with 2,6-diisopropylphenyl, NH]

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| Zr(Bn)$_4$ | 0.1 | RIBS-II | 0.15 | 0.2 | 2:1 | 0.5 | 6.7 | 1569 | 7821 | 4.98 |
| Zr(Bn)$_4$ | 0.1 | RIBS-II | 0.15 | 0.2 | 2:1 | 0.5 | 6.1 | 1668 | 7751 | 4.65 |
| Controls | | | | | | | | | | |
| Zr(Bn)$_4$ | 0.1 | RIBS-II | 0.15 | | | 0.5 | 4.4 | 6851 | 253328 | 36.98 |
| Zr(Bn)$_4$ | 0.1 | RIBS-II | 0.15 | | | 0.5 | 4.8 | 3980 | 267407 | 67.19 |

TABLE 4

Ligand = [1,3-bis(2,4,6-trimethylphenyl)-1H-imidazol-2(3H)-imine]

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| Hf(Bn)$_4$ | 0.1 | RIBS-II | 0.15 | 0.1 | 1:1 | 0.5 | | 3685 | 186766 | 50.68 |
| Hf(Bn)$_4$ | 0.1 | RIBS-II | 0.15 | 0.1 | 1:1 | 0.5 | | 5972 | 306225 | 51.28 |
| Hf(Bn)$_4$ | 0.1 | RIBS-II | 0.15 | 0.1 | 1:1 | 0.5 | 7.8 | 835 | 52180 | 62.49 |
| Hf(Bn)$_4$ | 0.1 | RIBS-II | 0.15 | 0.1 | 1:1 | 0.5 | 7.3 | 860 | 33942 | 39.47 |
| Zr(Bn)$_4$ | 0.1 | RIBS-II | 0.15 | 0.2 | 2:1 | 0.5 | 5.9 | 692 | 57701 | 83.38 |
| Zr(Bn)$_4$ | 0.1 | RIBS-II | 0.15 | 0.2 | 2:1 | 0.5 | 6.5 | 704 | 62612 | 88.94 |
| Controls | | | | | | | | | | |
| Zr(Bn)$_4$ | 0.1 | RIBS-II | 0.15 | | | 0.5 | 4.4 | 6851 | 253328 | 36.98 |
| Zr(Bn)$_4$ | 0.1 | RIBS-II | 0.15 | | | 0.5 | 4.8 | 3980 | 267407 | 67.19 |

TABLE 5

Ligand = [1,3-bis(2,6-diisopropylphenyl)-1H-imidazol-2(3H)-imine]

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| Hf(Bn)$_4$ | 0.1 | RIBS-II | 0.15 | 0.2 | 2:1 | 0.503 | 7.9 | 1789 | 4650 | 2.6 |
| Hf(Bn)$_4$ | 0.1 | RIBS-II | 0.15 | 0.2 | 2:1 | 0.503 | 10.2 | 1702 | 4587 | 2.17 |

TABLE 5-continued

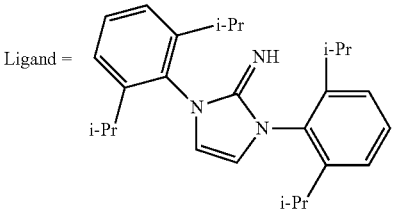 [SMILES: CC(C)c1cccc(C(C)C)c1-n1ccn(-c2c(C(C)C)cccc2C(C)C)c1=N]

Ligand =

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| Hf(Bn)$_4$ | 0.1 | RIBS-II | 0.15 | 0.1 | 1:1 | 0.503 | 13.5 | 1735 | 22732 | 13.1 |
| Hf(Bn)$_4$ | 0.1 | RIBS-II | 0.15 | 0.1 | 1:1 | 0.503 | 17.4 | 2106 | 25935 | 12.31 |
| Zr(Bn)$_4$ | 0.1 | RIBS-II | 0.15 | 0.1 | 1:1 | 0.503 | 7.4 | 1213 | 7865 | 6.48 |
| Zr(Bn)$_4$ | 0.1 | RIBS-II | 0.15 | 0.1 | 1:1 | 0.503 | 8.8 | 1160 | 6778 | 5.84 |
| Zr(Bn)$_4$ | 0.1 | RIBS-II | 0.15 | 0.2 | 2:1 | 0.503 | 16.8 | 1127 | 2715 | 2.41 |
| Zr(Bn)$_4$ | 0.1 | RIBS-II | 0.15 | 0.2 | 2:1 | 0.503 | 22.9 | 1088 | 2443 | 2.25 |
| Controls | | | | | | | | | | |
| Zr(Bn)$_4$ | 0.1 | RIBS-II | 0.15 | | | 0.503 | 4.5 | 4323 | 288214 | 66.67 |
| Zr(Bn)$_4$ | 0.1 | RIBS-II | 0.15 | | | 0.503 | 4.1 | 6348 | 315797 | 49.75 |

TABLE 6

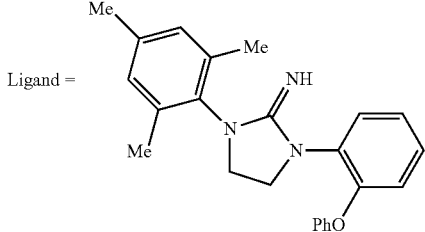 [SMILES: Cc1cc(C)c(N2CCN(c3ccccc3Oc3ccccc3)C2=N)c(C)c1]

Ligand =

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| Zr(Bn)$_4$ | 0.1 | RIBS-II | 0.15 | 0.1 | 1:1 | 0.503 | 6.0 | 1263 | 54011 | 42.76 |
| Zr(Bn)$_4$ | 0.1 | RIBS-II | 0.15 | 0.1 | 1:1 | 0.503 | 6.6 | 1290 | 72808 | 56.44 |
| Controls | | | | | | | | | | |
| Zr(Bn)$_4$ | 0.1 | RIBS-II | 0.15 | | | 0.503 | 4.5 | 4323 | 288214 | 66.67 |
| Zr(Bn)$_4$ | 0.1 | RIBS-II | 0.15 | | | 0.503 | 4.1 | 6348 | 315797 | 49.75 |

TABLE 7

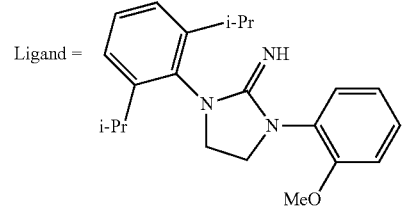 [SMILES: COc1ccccc1N1CCN(c2c(C(C)C)cccc2C(C)C)C1=N]

Ligand =

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| Zr(Bn)$_4$ | 0.1 | RIBS-II | 0.15 | 0.1 | 1:1 | 0.5 | 4.5 | 3810 | 226248 | 59.38 |
| Zr(Bn)$_4$ | 0.1 | RIBS-II | 0.15 | 0.1 | 1:1 | 0.5 | 4.4 | 3565 | 234785 | 65.86 |
| Controls | | | | | | | | | | |
| Zr(Bn)$_4$ | 0.1 | RIBS-II | 0.15 | | | 0.5 | 5.0 | 4886 | 280795 | 57.47 |
| Zr(Bn)$_4$ | 0.1 | RIBS-II | 0.15 | | | 0.5 | 4.6 | 6980 | 286837 | 41.09 |

TABLE 8

Ligand = [2-methoxyphenyl / mesityl imidazolidin-2-imine]

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| Zr(Bn)$_4$ | 0.1 | RIBS-II | 0.15 | 0.1 | 1:1 | 0.5 | 3.8 | 7357 | 354560 | 48.19 |
| Zr(Bn)$_4$ | 0.1 | RIBS-II | 0.15 | 0.1 | 1:1 | 0.5 | 4.8 | 4522 | 407757 | 90.17 |
| Controls | | | | | | | | | | |
| Zr(Bn)$_4$ | 0.1 | RIBS-II | 0.15 | | | 0.5 | 5.0 | 4886 | 280795 | 57.47 |
| Zr(Bn)$_4$ | 0.1 | RIBS-II | 0.15 | | | 0.5 | 4.6 | 6980 | 286837 | 41.09 |

TABLE 9

Ligand = [2-(methoxymethyl)phenyl / mesityl imidazolidin-2-imine]

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| Zr(Bn)$_4$ | 0.1 | RIBS-II | 0.15 | 0.1 | 1:1 | 0.503 | 5.1 | 1556 | 107204 | 69.90 |
| Zr(Bn)$_4$ | 0.1 | RIBS-II | 0.15 | 0.1 | 1:1 | 0.503 | 4.9 | 1554 | 90890 | 58.55 |
| Controls | | | | | | | | | | |
| Zr(Bn)$_4$ | 0.1 | RIBS-II | 0.15 | | | 0.503 | 6.3 | 2424 | 208984 | 86.21 |
| Zr(Bn)$_4$ | 0.1 | RIBS-II | 0.15 | | | 0.503 | 5.2 | 3784 | 349977 | 92.49 |

TABLE 10

Ligand = [2-methylphenyl / mesityl imidazolidin-2-imine]

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| Zr(Bn)$_4$ | 0.1 | RIBS-II | 0.15 | 0.1 | 1:1 | 0.503 | 6.9 | 824 | 34664 | 42.07 |
| Zr(Bn)$_4$ | 0.1 | RIBS-II | 0.15 | 0.1 | 1:1 | 0.503 | 6.9 | 908 | 28262 | 31.13 |
| Controls | | | | | | | | | | |
| Zr(Bn)$_4$ | 0.1 | RIBS-II | 0.15 | | | 0.503 | 4.2 | 4803 | 348156 | 72.49 |
| Zr(Bn)$_4$ | 0.1 | RIBS-II | 0.15 | | | 0.503 | 4.2 | 4071 | 351160 | 86.26 |

TABLE 11

Ligand = [structure: 1-(2,4,6-trimethylphenyl)-3-(2-methoxyphenyl)imidazolidin-2-imine]

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| Ti(Bn)$_4$ | 0.1 | FAB | 0.5 | 0.1 | 1:1 | 0.5 | 6.8 | 17220 | 164371 | 9.55 |
| Ti(Bn)$_4$ | 0.1 | FAB | 0.5 | 0.1 | 1:1 | 0.5 | 5.5 | 16017 | 185601 | 11.59 |
| Ti(Bn)$_4$ | 0.1 | FAB | 0.5 | 0.1 | 1:1 | 0.5 | 5.5 | 18717 | 184411 | 9.85 |
| Ti(Bn)$_4$ | 0.1 | RIBS-II | 0.15 | 0.1 | 1:1 | 0.5 | 8.2 | 6246 | 271385 | 43.45 |
| Ti(Bn)$_4$ | 0.1 | RIBS-II | 0.15 | 0.1 | 1:1 | 0.5 | 7.7 | 6484 | 296060 | 45.66 |
| Ti(Bn)$_4$ | 0.1 | RIBS-II | 0.15 | 0.1 | 1:1 | 0.5 | 8.0 | 6277 | 260791 | 41.55 |

TABLE 12

Ligand = [structure: 1-(2,6-diisopropylphenyl)-3-(2-methoxyphenyl)imidazolidin-2-imine]

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| Ti(Bn)$_4$ | 0.1 | FAB | 0.5 | 0.1 | 1:1 | 0.5 | 5.6 | 16455 | 134161 | 8.15 |
| Ti(Bn)$_4$ | 0.1 | FAB | 0.5 | 0.1 | 1:1 | 0.5 | 5.5 | 14540 | 140411 | 9.66 |
| Ti(Bn)$_4$ | 0.1 | FAB | 0.5 | 0.1 | 1:1 | 0.5 | 5.6 | 24904 | 148376 | 5.96 |
| Ti(Bn)$_4$ | 0.1 | RIBS-II | 0.15 | 0.1 | 1:1 | 0.5 | 5.9 | 10136 | 314116 | 30.99 |
| Ti(Bn)$_4$ | 0.1 | RIBS-II | 0.15 | 0.1 | 1:1 | 0.5 | 5.2 | 15281 | 362714 | 23.74 |
| Ti(Bn)$_4$ | 0.1 | RIBS-II | 0.15 | 0.1 | 1:1 | 0.5 | 7.5 | 6629 | 312771 | 47.18 |

TABLE 13

Ligand = [structure: 1-(2,4,6-trimethylphenyl)-3-(2-phenoxyphenyl)imidazolidin-2-imine]

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| Zr(Bn)$_4$ | 0.1 | RIBS-II | 0.15 | 0.1 | 1:1 | 0.5 | 5.5 | 2009 | 139890 | 69.63 |
| Zr(Bn)$_4$ | 0.1 | RIBS-II | 0.15 | 0.1 | 1:1 | 0.5 | 6.3 | 2071 | 151688 | 73.24 |

TABLE 14

Ligand = [structure: 1-(2,4,6-trimethylphenyl)-3-(2-methoxyphenyl)imidazolidin-2-imine]

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| Zr(Bn)$_4$ | 0.1 | RIBS-II | 0.15 | 0.1 | 1:1 | 0.5 | 4.6 | 4770 | 330464 | 69.28 |
| Zr(Bn)$_4$ | 0.1 | RIBS-II | 0.15 | 0.1 | 1:1 | 0.5 | 4.7 | 4550 | 307832 | 67.66 |
| Zr(Bn)$_4$ | 0.1 | RIBS-II | 0.15 | 0.1 | 1:1 | 0.5 | 4.7 | 4553 | 338179 | 74.28 |
| Zr(Bn)$_4$ | 0.1 | RIBS-II | 0.15 | 0.1 | 1:1 | 0.5 | 4.1 | 4666 | 317379 | 68.02 |
| Zr(Bn)$_4$ | 0.1 | RIBS-II | 0.15 | 0.1 | 1:1 | 0.5 | 4.4 | 4855 | 306114 | 63.05 |
| Controls | | | | | | | | | | |
| Zr(Bn)$_4$ | 0.1 | RIBS-II | 0.15 | | | 0.5 | 3.5 | 9812 | 342470 | 34.90 |
| Zr(Bn)$_4$ | 0.1 | RIBS-II | 0.15 | | | 0.5 | 4.3 | 6466 | 292247 | 45.2 |
| Zr(Bn)$_4$ | 0.1 | RIBS-II | 0.15 | | | 0.5 | 3.3 | 10238 | 324267 | 31.67 |
| Zr(Bn)$_4$ | 0.1 | RIBS-II | 0.15 | | | 0.5 | 4.0 | 5831 | 317540 | 54.46 |

TABLE 15

Ligand = [structure: 1-(2,6-diisopropylphenyl)-3-(2-methoxyphenyl)imidazolidin-2-imine]

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| Zr(Bn)$_4$ | 0.1 | RIBS-II | 0.15 | 0.1 | 1:1 | 0.5 | 4.7 | 3071 | 172521 | 56.18 |
| Zr(Bn)$_4$ | 0.1 | RIBS-II | 0.15 | 0.1 | 1:1 | 0.5 | 4.6 | 3155 | 167132 | 52.97 |
| Zr(Bn)$_4$ | 0.1 | RIBS-II | 0.15 | 0.1 | 1:1 | 0.5 | 4.6 | 3174 | 189859 | 59.82 |
| Zr(Bn)$_4$ | 0.1 | RIBS-II | 0.15 | 0.1 | 1:1 | 0.5 | 4.3 | 3168 | 157421 | 49.69 |
| Zr(Bn)$_4$ | 0.1 | RIBS-II | 0.15 | 0.1 | 1:1 | 0.5 | 4.3 | 3099 | 155668 | 50.23 |
| Controls | | | | | | | | | | |
| Zr(Bn)$_4$ | 0.1 | RIBS-II | 0.15 | | | 0.5 | 3.5 | 9812 | 342470 | 34.90 |
| Zr(Bn)$_4$ | 0.1 | RIBS-II | 0.15 | | | 0.5 | 4.3 | 6466 | 292247 | 45.20 |
| Zr(Bn)$_4$ | 0.1 | RIBS-II | 0.15 | | | 0.5 | 3.3 | 10238 | 324267 | 31.67 |
| Zr(Bn)$_4$ | 0.1 | RIBS-II | 0.15 | | | 0.5 | 4.0 | 5831 | 317540 | 54.46 |

TABLE 16

Ligand = [structure: imidazolidin-2-imine with N-mesityl and N-(2-methoxymethyl)phenyl substituents]

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| Zr(Bn)$_4$ | 0.1 | RIBS-II | 0.15 | 0.1 | 1:1 | 0.503 | 4.6 | 1908 | 120613 | 63.21 |
| Zr(Bn)$_4$ | 0.1 | RIBS-II | 0.15 | 0.1 | 1:1 | 0.503 | 5.2 | 1576 | 110406 | 70.05 |
| Controls | | | | | | | | | | |
| Zr(Bn)$_4$ | 0.1 | RIBS-II | 0.15 | | | 0.503 | 6.3 | 2424 | 208984 | 86.21 |
| Zr(Bn)$_4$ | 0.1 | RIBS-II | 0.15 | | | 0.503 | 5.2 | 3784 | 349977 | 92.49 |

TABLE 17

Ligand = [structure: imidazolidin-2-imine with N-mesityl and N-(2-methylphenyl) substituents]

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| Zr(Bn)$_4$ | 0.1 | RIBS-II | 0.15 | 0.1 | 1:1 | 0.5 | 8.1 | 904 | 29330 | 32.44 |
| Zr(Bn)$_4$ | 0.1 | RIBS-II | 0.15 | 0.1 | 1:1 | 0.5 | 6.9 | 981 | 31533 | 32.14 |
| Zr(Bn)$_4$ | 0.1 | RIBS-II | 0.15 | 0.1 | 1:1 | 0.5 | 8.8 | 782 | 8299 | 10.61 |

TABLE 18

Ligand = [structure: imidazolidin-2-imine with N-mesityl and N-(2-methylphenyl) substituents]

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| Hf(Bn)$_4$ | 0.1 | RIBS-II | 0.15 | 0.1 | 1:1 | 0.5 | 14.4 | 2950 | 91585 | 31.05 |
| Hf(Bn)$_4$ | 0.1 | RIBS-II | 0.15 | 0.1 | 1:1 | 0.5 | 14.9 | 2814 | 56648 | 20.13 |

TABLE 19
Metal-Ligand Complex =
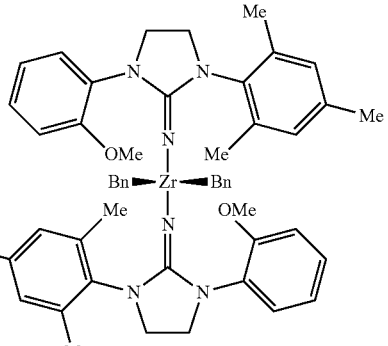
| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| — | 0.1 | RIBS-II | 0.15 | — | — | 0.5 | 14.4 | 2950 | 91585 | 31.05 |
| — | 0.1 | RIBS-II | 0.15 | — | — | 0.5 | 14.9 | 2814 | 56648 | 20.13 |
TABLE 20
Metal-Ligand Complex =
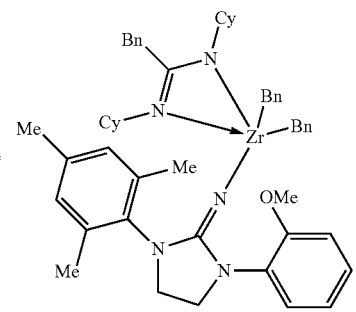
| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| — | 0.1 | RIBS-II | 0.15 | — | — | 0.5 | 1.5 | 41534 | 396801 | 9.55 |
| — | 0.1 | RIBS-II | 0.15 | — | — | 0.5 | 1.2 | 17700 | 309752 | 17.50 |
| — | 0.1 | RIBS-II | 0.15 | — | — | 0.5 | 1.0 | 43240 | 430695 | 9.96 |
| Controls | | | | | | | | | | |
| Zr(Bn)$_4$ | 0.1 | RIBS-II | 0.15 | | | 0.5 | 3.7 | 9108 | 295644 | 32.46 |
| Zr(Bn)$_4$ | 0.1 | RIBS-II | 0.15 | | | 0.5 | 3.8 | 10039 | 276226 | 27.52 |

TABLE 21
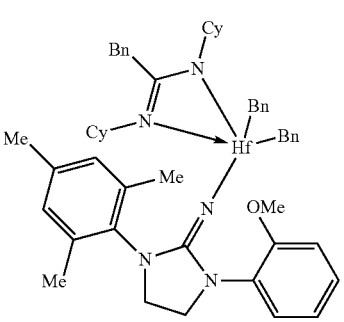
Metal-Ligand Complex =
| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| — | 0.1 | RIBS-II | 0.15 | — | — | 0.5 | | 75931 | 239754 | 3.16 |
| — | 0.1 | RIBS-II | 0.15 | — | — | 0.5 | | 65892 | 257734 | 3.91 |
| — | 0.1 | RIBS-II | 0.15 | — | — | 0.5 | | 55711 | 228602 | 4.10 |
| Controls | | | | | | | | | | |
| Zr(Bn)$_4$ | 0.1 | RIBS-II | 0.15 | | | 0.5 | | 5139 | 367603 | 71.53 |
| Zr(Bn)$_4$ | 0.1 | RIBS-II | 0.15 | | | 0.5 | | 4854 | 353604 | 72.85 |
TABLE 22
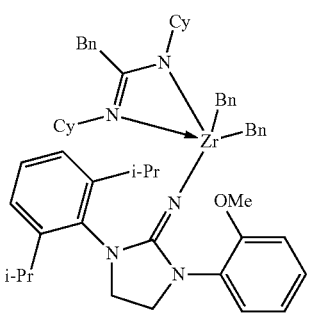
Metal-Ligand Complex =
| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| — | 0.1 | RIBS-II | 0.15 | — | — | 0.5 | | 7644 | 241494 | 31.59 |
| — | 0.1 | RIBS-II | 0.15 | — | — | 0.5 | | 54563 | 254407 | 4.66 |
| Controls | | | | | | | | | | |
| Zr(Bn)$_4$ | 0.1 | RIBS-II | 0.15 | | | 0.5 | | 5139 | 367603 | 71.53 |
| Zr(Bn)$_4$ | 0.1 | RIBS-II | 0.15 | | | 0.5 | | 4854 | 353604 | 72.85 |

TABLE 23

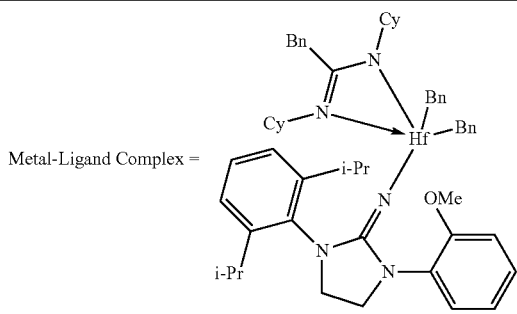

Metal-Ligand Complex =

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| — | 0.1 | RIBS-II | 0.15 | — | — | 0.5 |  | 82507 | 229368 | 2.78 |
|  |  |  |  | Controls |  |  |  |  |  |  |
| Zr(Bn)$_4$ | 0.1 | RIBS-II | 0.15 |  |  | 0.5 |  | 5139 | 367603 | 71.53 |
| Zr(Bn)$_4$ | 0.1 | RIBS-II | 0.15 |  |  | 0.5 |  | 4854 | 353604 | 72.85 |

TABLE 24

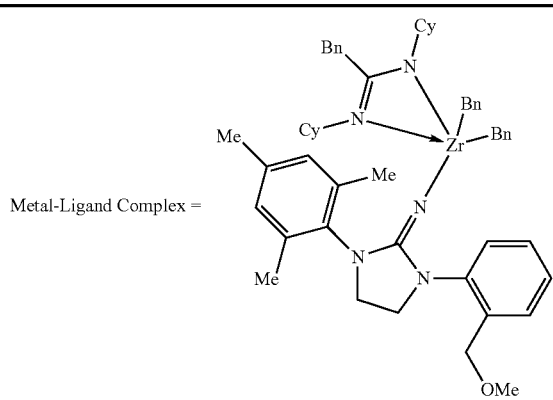

Metal-Ligand Complex =

| Metal | Metal (μmol) | Co-catalyst | Co-catalyst (μmol) | Ligand (μmol) | L:M | MMAO (μmol) | Octene (mol %) | Mn | Mw | MWD |
|---|---|---|---|---|---|---|---|---|---|---|
| — | 0.1 | RIBS-II | 0.15 | — | — | 0.5 | 1.4 | 25355 | 468225 | 18.47 |
| — | 0.1 | RIBS-II | 0.15 | — | — | 0.5 | 1.4 | 57110 | 422197 | 7.39 |
| — | 0.1 | RIBS-II | 0.15 | — | — | 0.5 | 1.3 | 24212 | 379072 | 15.66 |
| — | 0.1 | RIBS-II | 0.15 | — | — | 0.5 | 2.1 | 16427 | 488105 | 29.71 |
| — | 0.1 | RIBS-II | 0.15 | — | — | 0.5 | 2.0 | 15796 | 529514 | 33.52 |
| — | 0.1 | RIBS-II | 0.15 | — | — | 0.5 | 1.9 | 19901 | 475700 | 23.90 |

The invention claimed is:

1. A metal-ligand complex of formula (I):

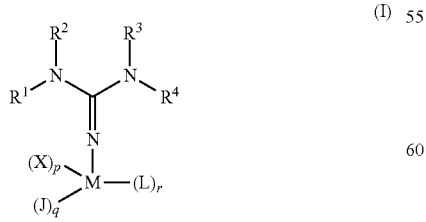

wherein

J is a monoanionic moiety selected from $(R^K)(R^L)(R^X)$ P=N—, $(R^K)(R^L)C=N—$, $(R^K)((R^L)(R^X)N)C=N—$, $(R^K)(R^L)B—O—$, $R^KO—$, $R^KS—$, $R^KS(O)—$, $(R^K)(R^L)N—$, $(R^KN=C(R^L)—N(R^X))—$, $(R^K)(R^L)NO—$, $R^KC(O)O—$, $R^KC(O)NH—$, and $(R^K)(R^L)P—$, wherein each $R^K$, $R^L$, and $R^X$ is independently is hydrogen, (C$_1$-C$_{40}$)hydrocarbyl-, ((C$_1$-C$_{15}$)hydrocarbyl)$_3$Si—, ((C$_1$-C$_{15}$)hydrocarbyl)$_2$N—, or (C$_1$-C$_{40}$)heterohydrocarbyl-; provided that wne J is $(R^K)(R^L)P—$ or $(R^K)(R^L)N—$, $R^K$ and $R^L$ are optionally taken together to form (C$_2$-C$_{40}$)hydrocarbylene or (C$_1$-C$_{40}$)heterohydrocarbylene, or $R^K$ and $R^L$ are optionally taken together to form a group double bonded to P—, or one of $R^K$ and $R^L$ is optionally taken together with one of $R^1$, $R^2$, $R^3$, $R^4$, or L to form a (C$_2$-C$_{40}$)hydrocarbylene or (C$_1$-C$_{40}$)heterohydrocarbylene, or one of $R^K$ and $R^L$ is optionally covalently bonded to X; and provided that when J is $R^KO—$ or $R^KS—$, $R^K$ is optionally taken together with one of $R^1$, $R^2$, $R^3$, $R^4$, or L to form a $(C_1$-$C_{40})$heterohydrocarbylene, or $R^K$ is optionally covalently bonded to X;

L is independently at each occurrence halogen, hydrogen, $((C_1$-$C_{40})$hydrocarbyl)C(O)N(H)—, $((C_1$-$C_{40})$hydrocarbyl)C(O)N(H)(C_1$-$C_{20})$hydrocarbyl-, $((C_1$-$C_{40})$hydrocarbyl)C(O)O—, $(C_1$-$C_{40})$hydrocarbyl-, $(C_1$-$C_{40})$heterohydrocarbyl-, $R^K(R^L)N$—, $R^LO$—, $R^LS$—, or $R^K(R^L)P$—, wherein each of $R^K$ and $R^L$ independently is as defined above; and each occurrence of L is a monoanionic moiety that is bonded to M;

M is a metal of any one of Groups 3, 4, 5, and 6 of a Periodic Table of the Elements, the metal being in a formal oxidation state of +2, +3, +4, +5, or +6;

$R^1$, $R^2$, $R^3$, and $R^4$ are independently at each occurrence hydrogen, $(C_1$-$C_{40})$hydrocarbyl-, $((C_1$-$C_{40})$hydrocarbyl)O—, $((C_1$-$C_{40})$hydrocarbyl)S—, $((C_1$-$C_{40})$hydrocarbyl)_3Si$—, or $(C_1$-$C_{40})$heterohydrocarbyl-;

X is a neutral Lewis base group selected from $R^XN(R^K)(R^L)$, $R^X=N(R^K)$, $R^KO(R^L)$, $R^KS(R^L)$, and $R^XP(R^K)(R^L)$, wherein each of $R^K$, $R^L$, and $R^X$ independently is as defined above;

p is 0, 1, 2, or 3, and q is 0 or 1, provided that the sum of p and q is at least 1;

r is 2 or 3;

two occurrences of L are optionally taken together to form a $(C_2$-$C_{40})$hydrocarbylene or $(C_1$-$C_{40})$heterohydrocarbylene, or $(R^D)_2C=C(R^D)$—$C(R^D)=C(R^D)_2$, wherein each $R^D$ independently is H, unsubstituted $(C_1$-$C_6)$alkyl, phenyl, or naphthyl;

J and one of $R^1$, $R^2$, $R^3$, and $R^4$ are optionally taken together to form $(C_2$-$C_{40})$hydrocarbylene or $(C_1$-$C_{40})$heterohydrocarbylene;

one occurrence of L and one of $R^1$, $R^2$, $R^3$, and $R^4$ are optionally taken together to form $(C_2$-$C_{40})$hydrocarbylene or $(C_1$-$C_{40})$heterohydrocarbylene;

one occurrence of X and one of $R^1$, $R^2$, $R^3$, and $R^4$ are optionally taken together to form $(C_1$-$C_{40})$heterohydrocarbylene;

any two of $R^1$, $R^2$, $R^3$, and $R^4$ are optionally taken together to form a $(C_2$-$C_{40})$hydrocarbylene or $(C_1$-$C_{40})$heterohydrocarbylene;

X and J are optionally taken together to form a monoanionic bidentate moiety X-J, provided that when X-J is bound to M to form a fragment having the structure

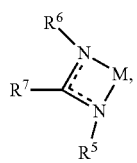

then $R^5$, $R^6$, and $R^7$ are each independently hydrogen, $(C_1$-$C_{40})$hydrocarbyl-, $((C_1$-$C_{40})$hydrocarbyl)O—, $((C_1$-$C_{40})$hydrocarbyl)S—, $((C_1$-$C_{40})$hydrocarbyl)_3Si$—, or $(C_1$-$C_{40})$heterohydrocarbyl-; one of $R^5$, $R^6$, or $R^7$ is optionally taken together with one of $R^1$, $R^2$, $R^3$, $R^4$, or L to form a $(C_2$-$C_{40})$hydrocarbylene or (C1-C40)heteohydrocarbylene; and provided that when X-J is bound to M via an anionic nitrogen and a Lewis base nitrogen, X-J and M form a four-membered metallocycle or a six-membered metallocycle; and each of the above-mentioned $(C_1$-$C_{40})$hydrocarbyl, $(C_1$-$C_{40})$heterohydrocarbyl, $(C_2$-$C_{40})$hydrocarbylene, and $(C_1$-$C_{40})$heterohydrocarbylene independently is the same or different and is unsubstituted or substituted with one or more substituents $R^S$ selected from halogen, unsubstituted $(C_1$-$C_{18})$hydrocarbyl, $F_3C$—, $FCH_2O$—, $F_2HCO$—, $F_3CO$—, oxo, $R_3Si$—, RO—, RS—, RS(O)—, $RS(O)_2$—, $R_2P$—, $R_2N$—, $R_2C=N$—, NC—, RC(O)O—, ROC(O)—, RC(O)N(R)—, or $R_2NC(O)$—, wherein each R independently is an unsubstituted $(C_1$-$C_{18})$hydrocarbyl.

2. The metal-ligand complex of claim 1, wherein M is Ti, Zr, or Hf.

3. The metal-ligand complex of claim 1, wherein one of $R^1$ and $R^2$ and one of $R^3$ and $R^4$ are taken together to form

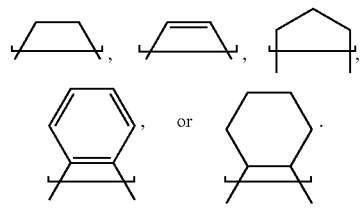

4. The metal-ligand complex of claim 1, having formula (II)

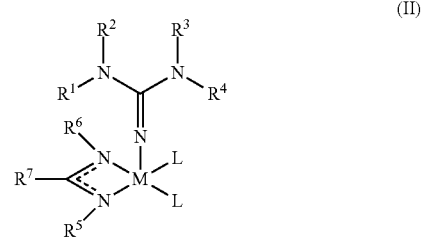

wherein

L, M, $R^1$, $R^2$, $R^3$, and $R^4$ are as defined in claim 1;

$R^5$, $R^6$, and $R^7$ are each independently hydrogen, $(C_1$-$C_{40})$hydrocarbyl-, $((C_1$-$C_{40})$hydrocarbyl)O—, $((C_1$-$C_{40})$hydrocarbyl)S—, $((C_1$-$C_{40})$hydrocarbyl)_3Si$—, or $(C_1$-$C_{40})$heterohydrocarbyl-;

one occurrence of L and any one of $R^1$, $R^2$, $R^3$, or $R^4$ are optionally taken together to form $(C_2$-$C_{40})$hydrocarbylene or $(C_1$-$C_{40})$heterohydrocarbylene;

any two of $R^1$, $R^2$, $R^3$, or $R^4$ are optionally taken together to form a $(C_2$-$C_{40})$hydrocarbylene or $(C_1$-$C_{40})$heterohydrocarbylene;

one of $R^5$, $R^6$, or $R^7$ is optionally taken together with one of $R^1$, $R^2$, $R^3$, $R^4$, or L to form a $(C_2$-$C_{40})$hydrocarbylene or $(C_1$-$C_{40})$heterohydrocarbylene; and the two occurrences of L are optionally taken together to form a $(C_2$-$C_{40})$hydrocarbylene or $(C_1$-$C_{40})$heterohydrocarbylene, or $(R^D)_2C=C(R^D)$—$C(R^D)=C(R^D)_2$, wherein each $R^D$ independently is H, unsubstituted $(C_1$-$C_6)$alkyl, phenyl, or naphthyl.

5. The metal-ligand complex of claim 4, selected from the group consisting of

107
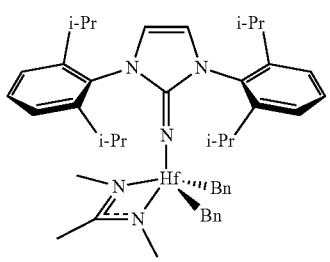
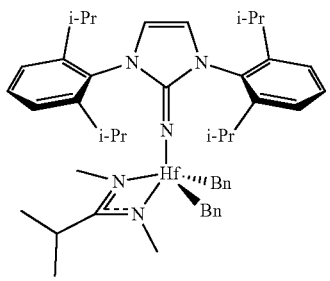
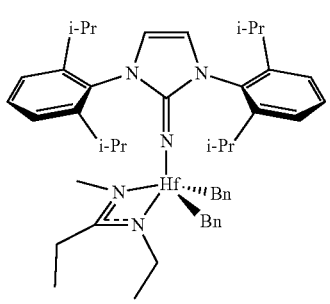
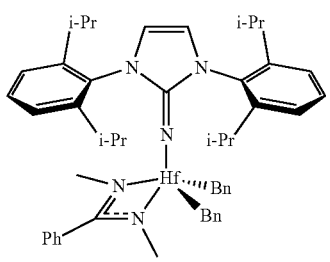
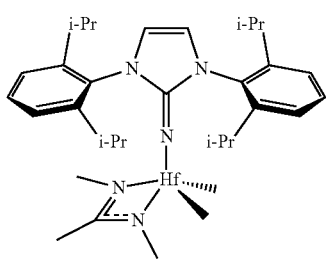
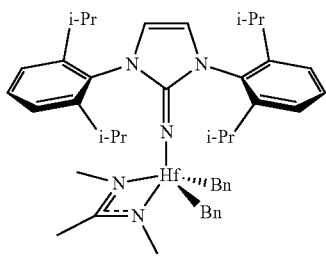
108
-continued
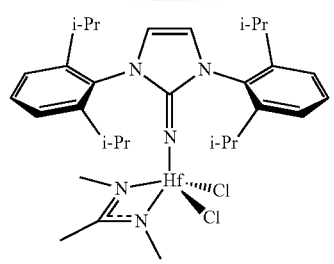
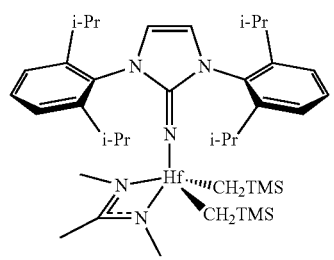
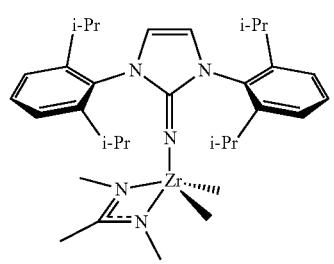
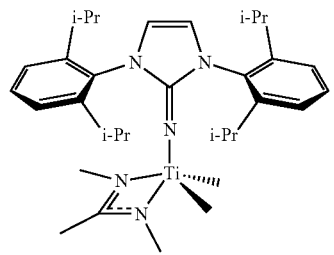
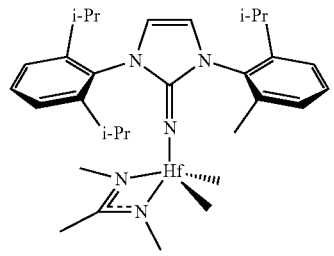
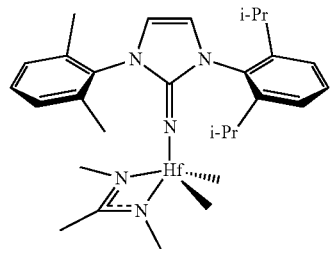

109
-continued
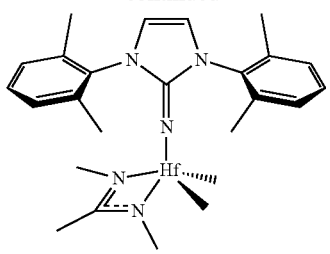
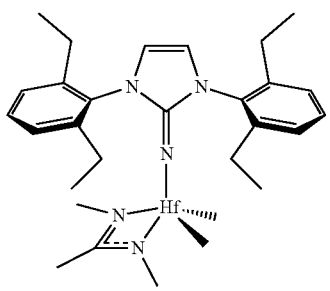
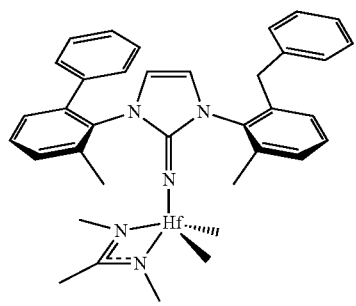
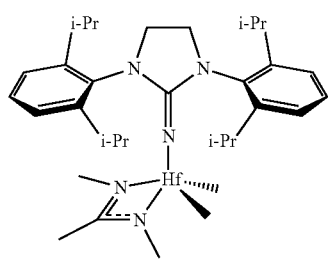
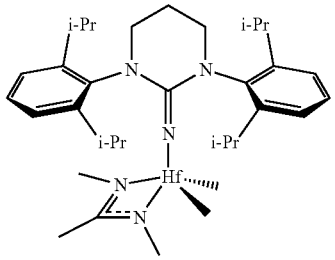
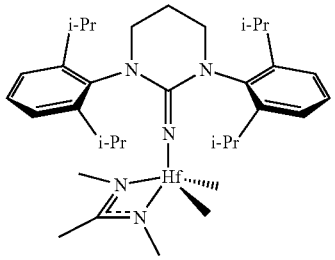
110
-continued
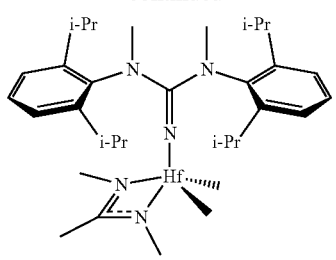
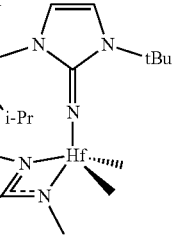
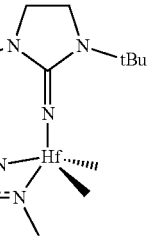
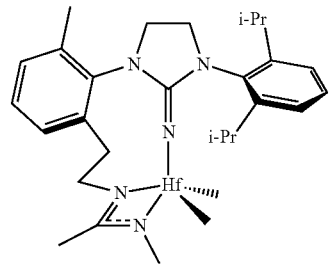
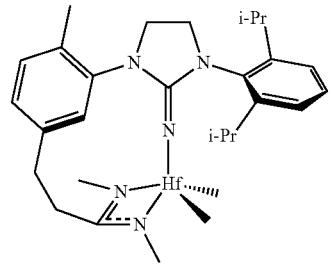
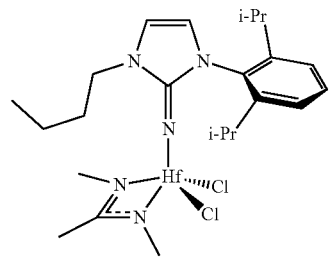

-continued

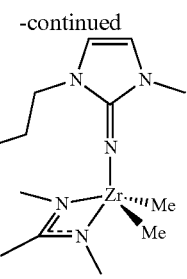

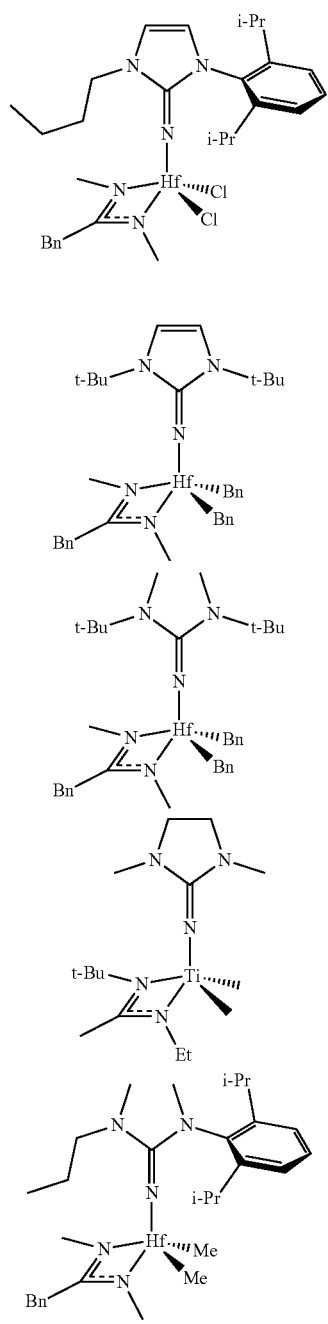

and combinations thereof.

6. The metal-ligand complex of claim 1, having formula (III)

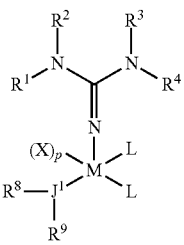

(III)

wherein
L, M, p, $R^1$, $R^2$, $R^3$, $R^4$, and X are as defined in claim 1;
$J^1$ is N or P;
$R^8$ and $R^9$ are each independently hydrogen, $(C_1-C_{40})$hydrocarbyl-, $((C_1-C_{40})$hydrocarbyl)O—, $((C_1-C_{40})$hydrocarbyl)S—, $((C_1-C_{15})$hydrocarbyl)$_3$Si—, or $(C_1-C_{40})$heterohydrocarbyl-;
one occurrence of L and any one of $R^1$, $R^2$, $R^3$, or $R^4$ are optionally taken together to form $(C_2-C_{40})$hydrocarbylene or $(C_1-C_{40})$heterohydrocarbylene;
the two occurrences of L are optionally taken together to form a $(C_2-C_{40})$hydrocarbylene or $(C_1-C_{40})$heterohydrocarbylene, or $(R^D)_2C=C(R^D)—C(R^D)=C(R^D)_2$, wherein each $R^D$ independently is H, unsubstituted $(C_1-C_6)$alkyl, phenyl, or naphthyl;
any two of $R^1$, $R^2$, $R^3$, or $R^4$ optionally are taken together to form a $(C_2-C_{40})$hydrocarbylene or $(C_1-C_{40})$heterohydrocarbylene;
$R^8$ and $R^9$ are optionally taken together to form $(C_2-C_{40})$hydrocarbylene or $(C_1-C_{40})$heterohydrocarbylene, if $J^1$ is P;
$R^8$ and $R^9$ are optionally taken together to form a group double bonded to $J^1$, if $J^1$ is P;
one of $R^8$ and $R^9$ is optionally taken together with one of $R^1$, $R^2$, $R^3$, $R^4$, or L to form a $(C_2-C_{40})$hydrocarbylene or $(C_1-C_{40})$heterohydrocarbylene;
one of $R^8$ and $R^9$ is optionally covalently bonded to X; and
X and any one of $R^1$, $R^2$, $R^3$, or $R^4$ are optionally taken together to form $(C_1-C_{40})$heterohydrocarbylene.

7. The metal-ligand complex of claim 6, selected from the group consisting of

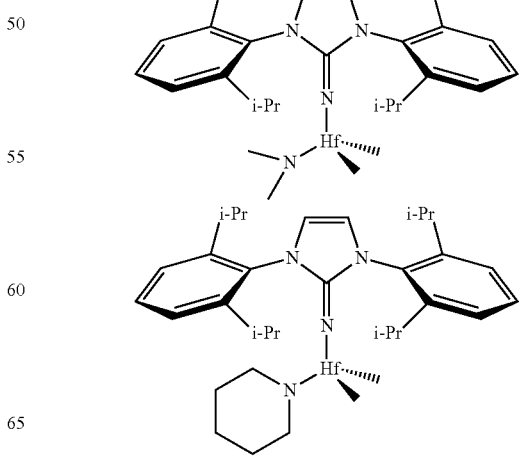

113
-continued
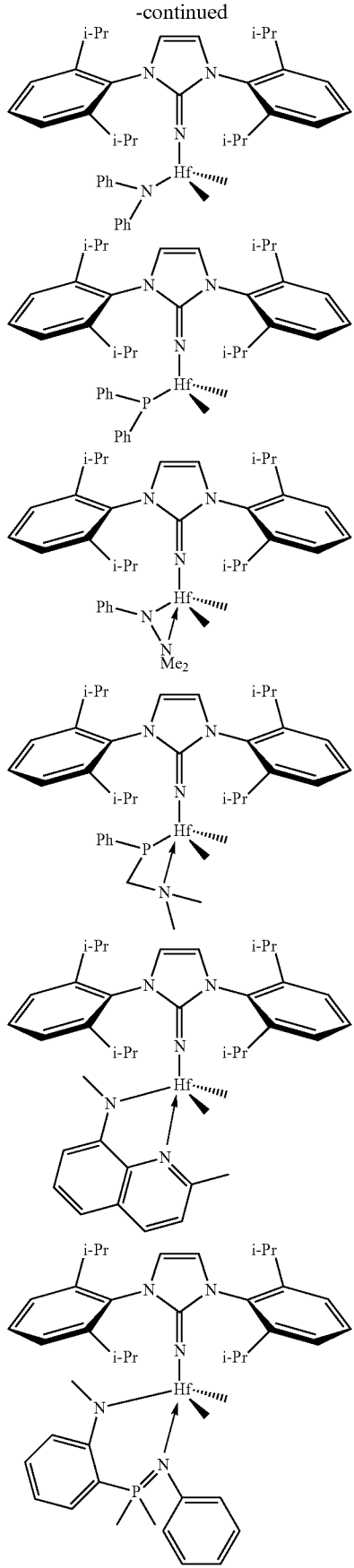
114
-continued
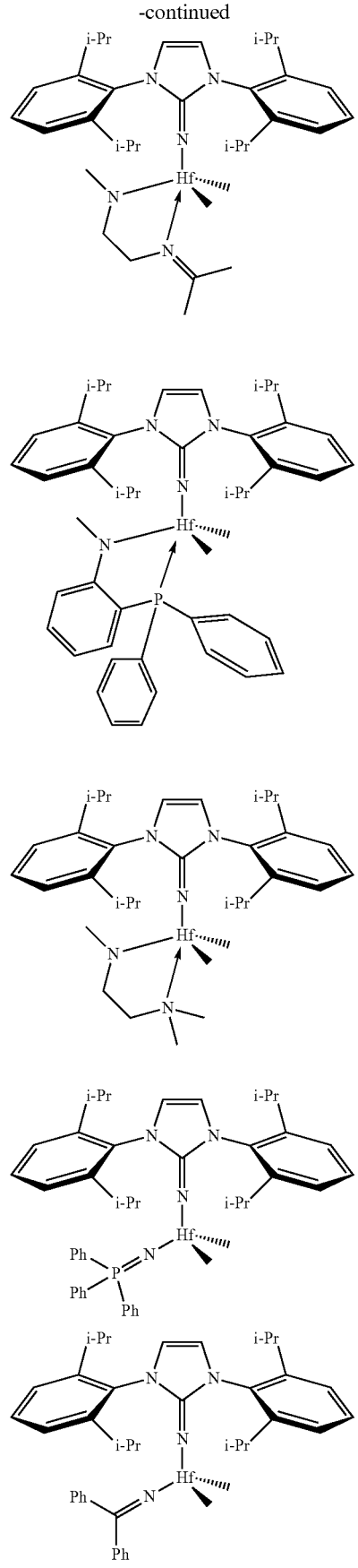

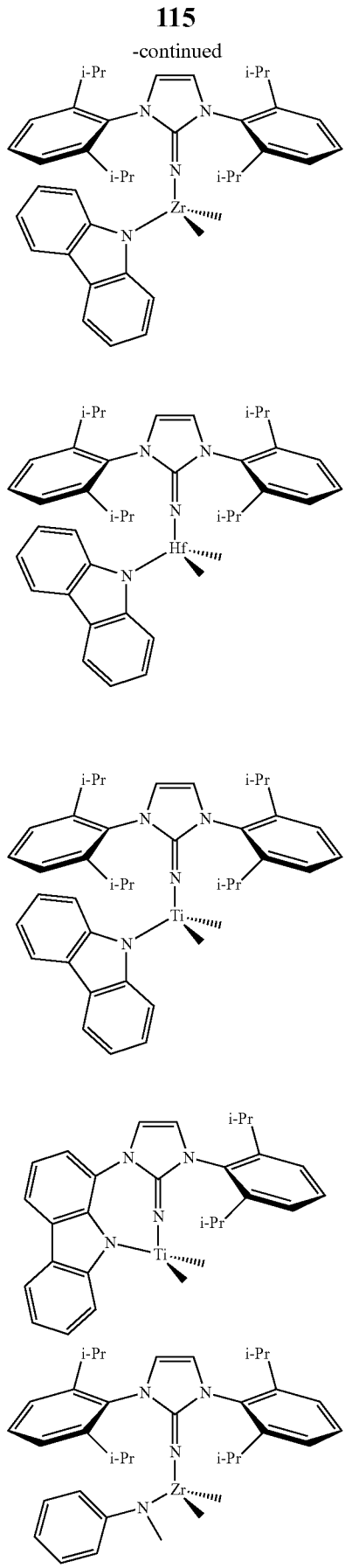

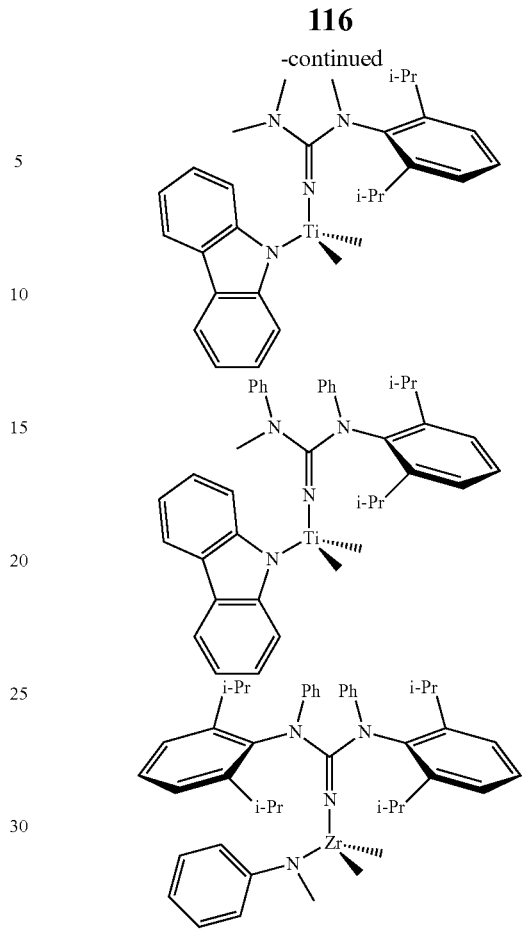

and combinations thereof.

8. The metal-ligand complex of claim 1, having formula (IV)

$$\text{(IV)}$$

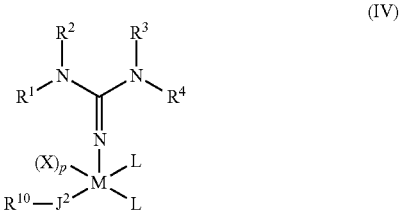

wherein

L, M, p, $R^1$, $R^2$, $R^3$, $R^4$, and X are as defined in claim 1;
$J^2$ is O or S; and
$R^{10}$ is $(C_1-C_{40})$hydrocarbyl-, $((C_1-C_{15})$hydrocarbyl$)_3$Si—, or $(C_1-C_{40})$heterohydrocarbyl-;
one occurrence of L and any one of $R^1$, $R^2$, $R^3$, or $R^4$ are optionally taken together to form $(C_2-C_{40})$hydrocarbylene or $(C_1-C_{40})$heterohydrocarbylene;
any two of $R^1$, $R^2$, $R^3$, or $R^4$ optionally are taken together to form a $(C_2-C_{40})$hydrocarbylene or $(C_1-C_{40})$heterohydrocarbylene;
X and any one of $R^1$, $R^2$, $R^3$, or $R^4$ are optionally taken together to form $(C_1-C_{40})$heterohydrocarbylene; and
$R^{10}$ is optionally taken together with one of $R^1$, $R^2$, $R^3$, $R^4$, or L to form a $(C_1-C_{40})$heterohydrocarbylene; and
$R^{10}$ is optionally covalently bonded to X.

9. The metal-ligand complex of claim 8, selected from the group consisting of 117
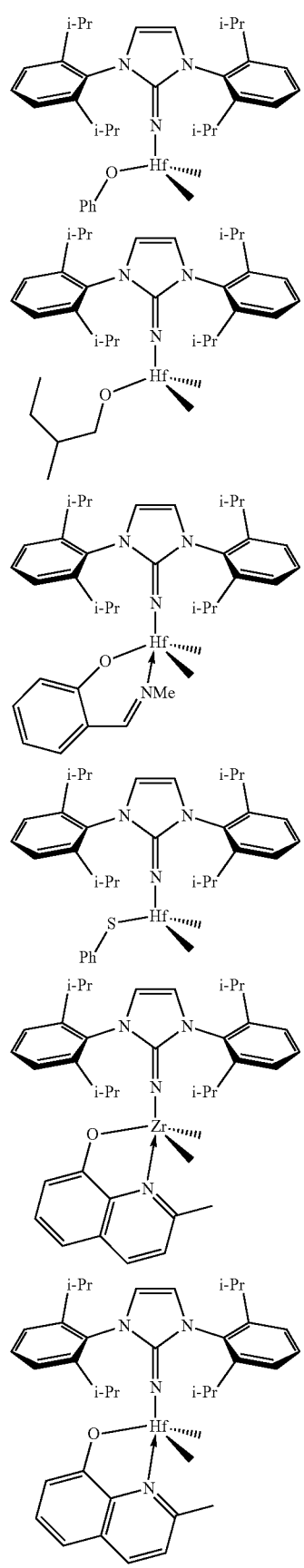
118
-continued
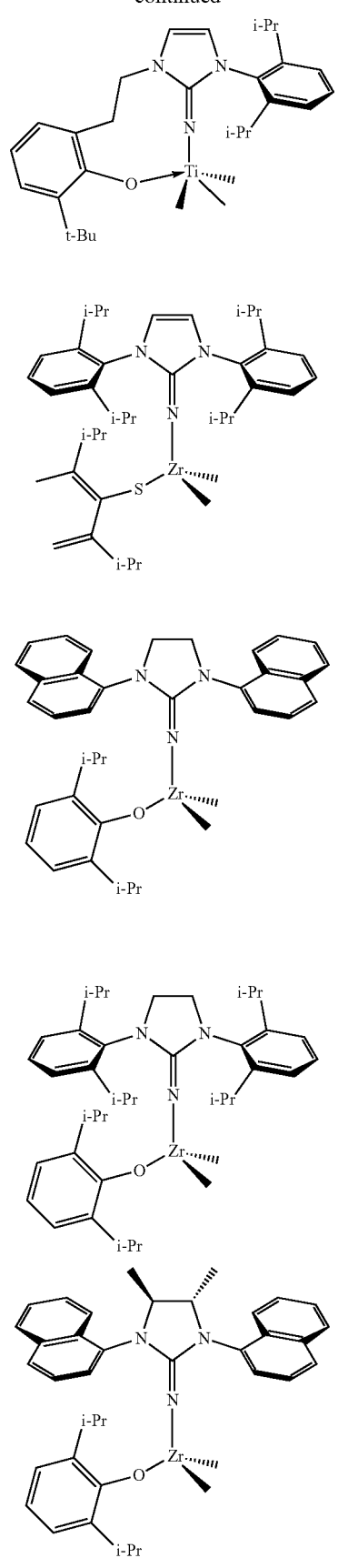

-continued

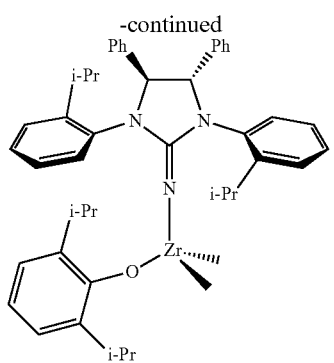

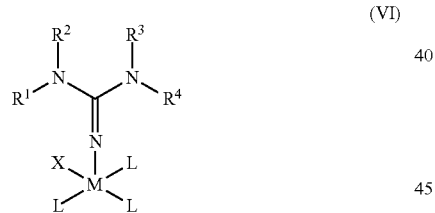

and combinations thereof.

10. The metal-ligand complex claim 1, having formula (VI)

$$\begin{array}{c} R^2 \quad R^3 \\ R^1\text{-N} \quad \text{N-}R^4 \\ \text{N} \\ X\text{-M-}L \\ L \quad L \end{array} \quad \text{(VI)}$$

wherein

L, M, $R^1$, $R^2$, $R^3$, $R^4$, and X are as defined for formula (I);

two occurrences of L are optionally taken together to form a $(C_2\text{-}C_{40})$hydrocarbylene or $(C_1\text{-}C_{40})$heterohydrocarbylene, or $(R^D)_2C=C(R^D)-C(R^D)=C(R^D)_2$, wherein each $R^D$ independently is H, unsubstituted $(C_1\text{-}C_6)$ alkyl, phenyl, or naphthyl;

one occurrence of L and one of $R^1$, $R^2$, $R^3$, or $R^4$ are optionally taken together to form $(C_2\text{-}C_{40})$hydrocarbylene or $(C_1\text{-}C_{40})$heterohydrocarbylene;

X and one of $R^1$, $R^2$, $R^3$, or $R^4$ are optionally taken together to form $(C_1\text{-}C_{40})$heterohydrocarbylene; and any two of $R^1$, $R^2$, $R^3$, or $R^4$ are optionally taken together to form a $(C_2\text{-}C_{40})$hydrocarbylene or $(C_1\text{-}C_{40})$heterohydrocarbylene.

11. The metal ligand complex of claim 10, selected from the group consisting of

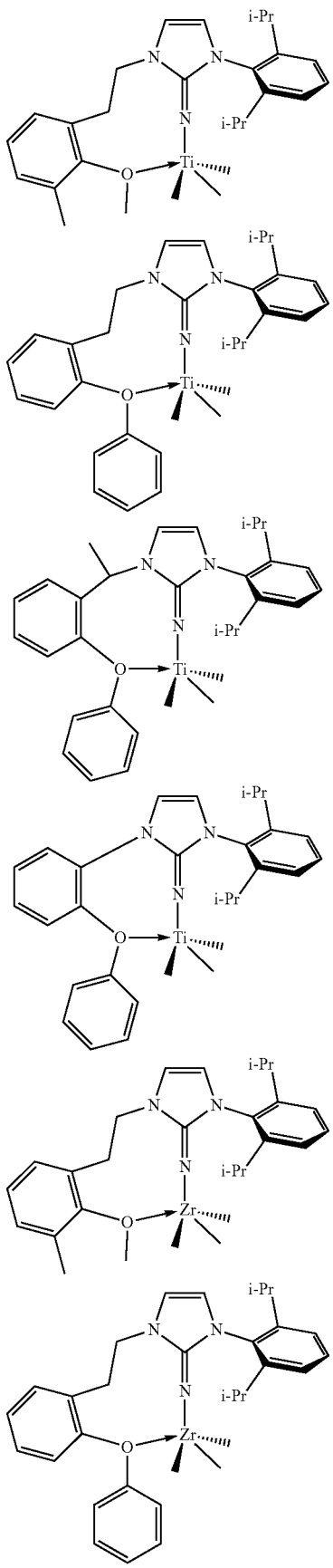

121
-continued
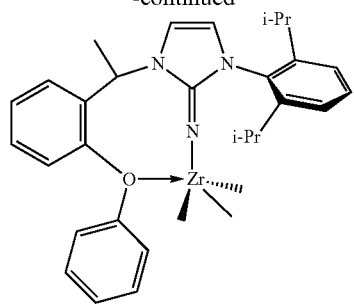
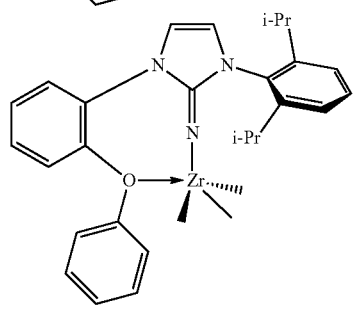
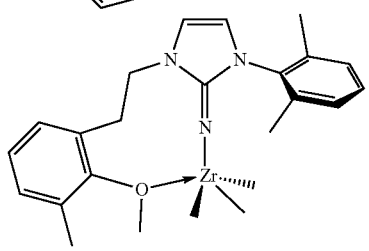
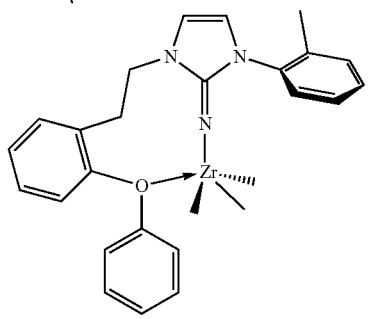
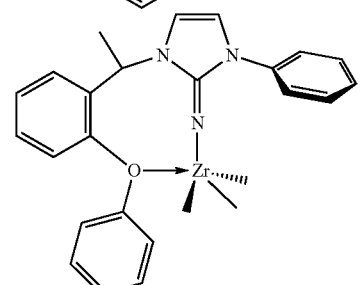
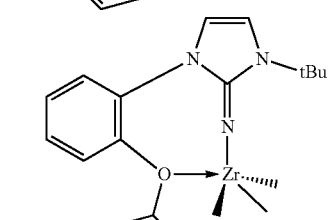
122
-continued
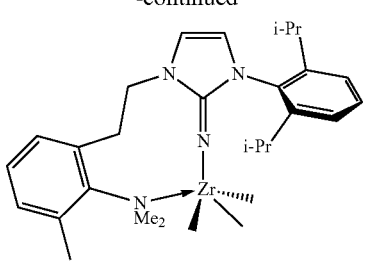
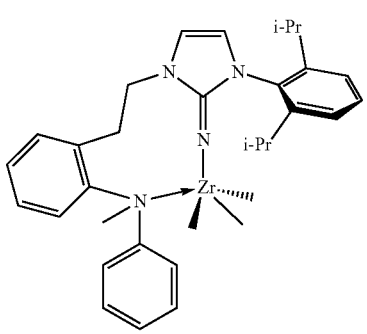
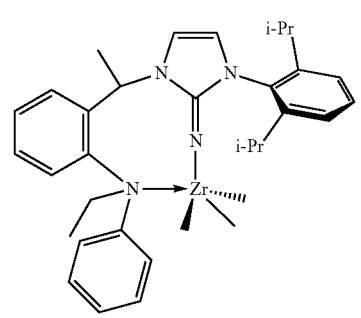
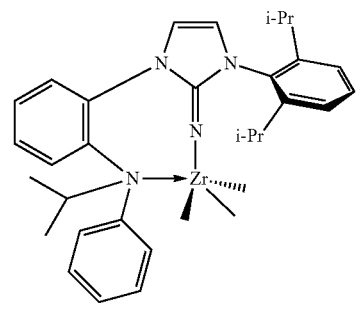
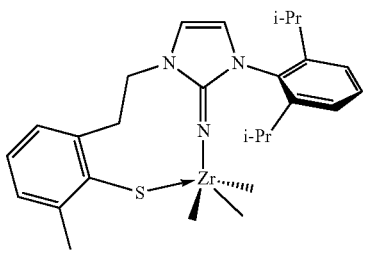

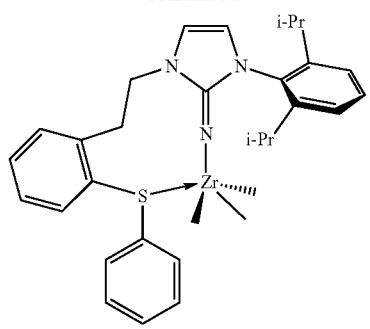
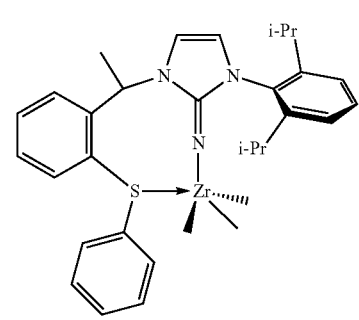
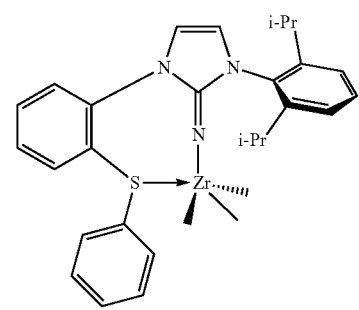
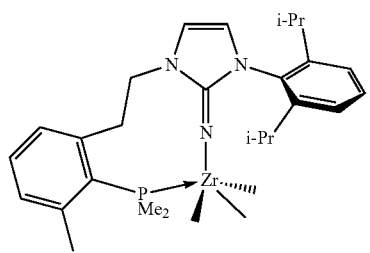
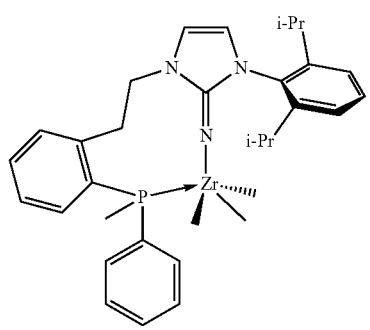
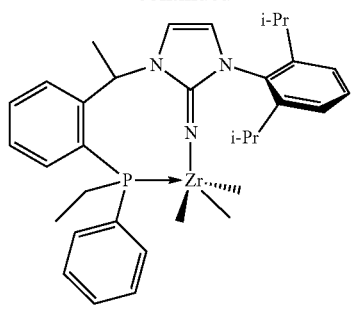
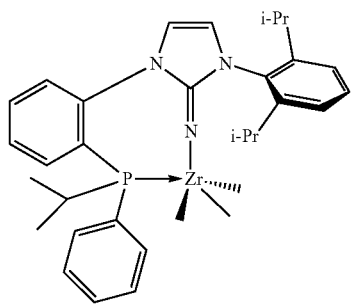
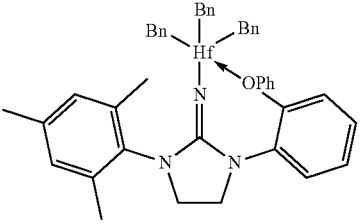
and combinations thereof.
12. The metal-ligand complex of claim 1, selected from the group consisting of
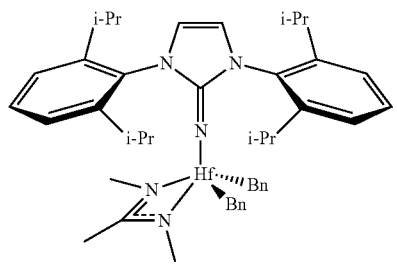
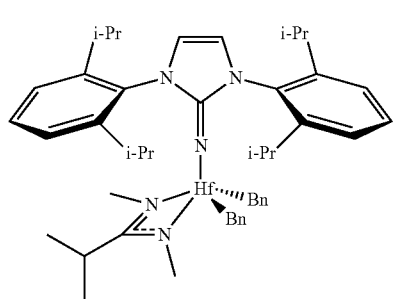

125
-continued
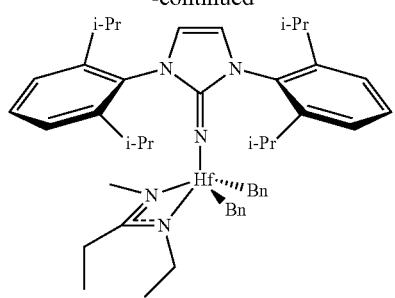
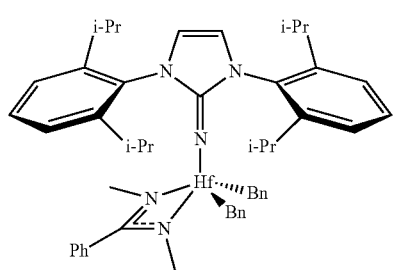
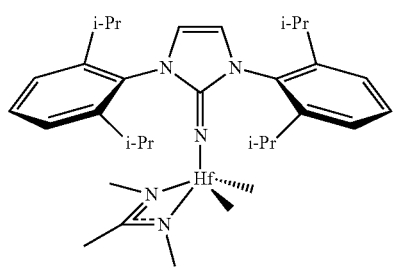
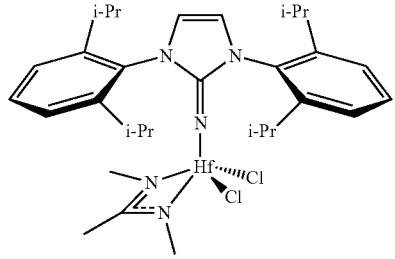
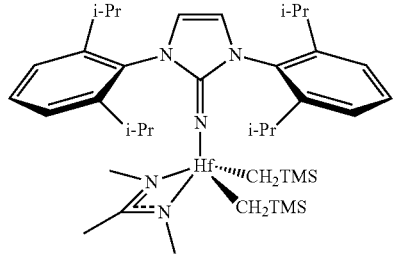
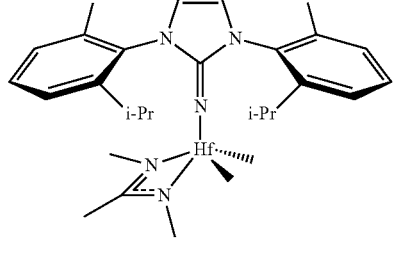
126
-continued
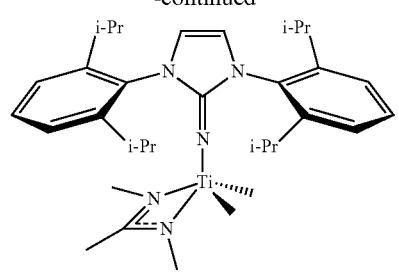
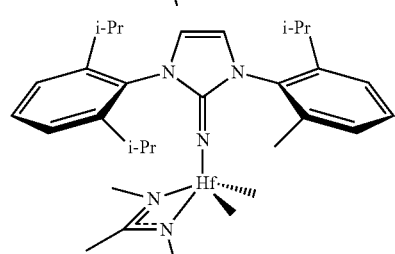
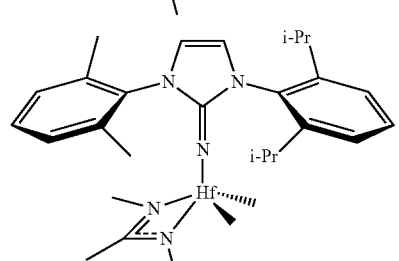
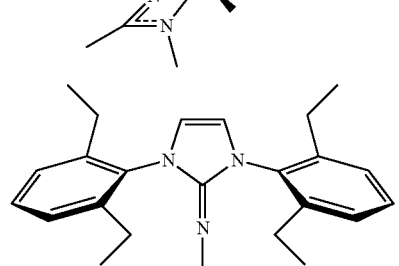
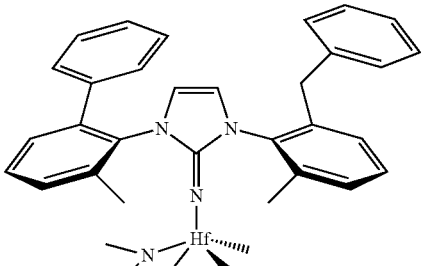
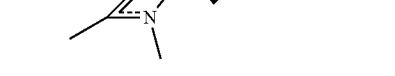

127
-continued
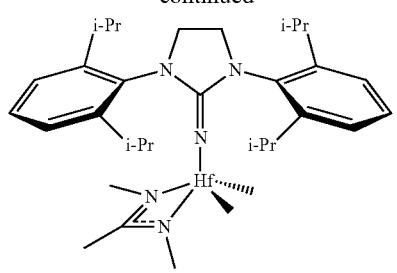
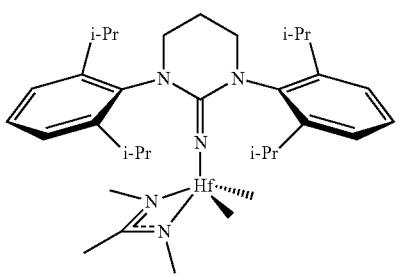
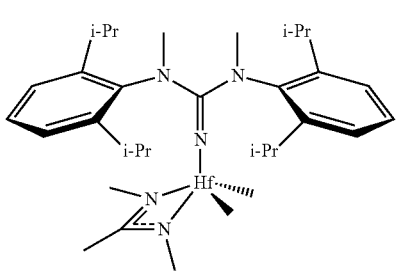
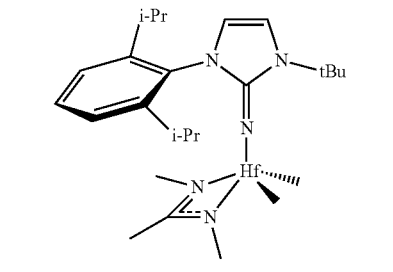
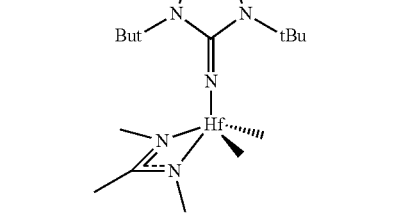
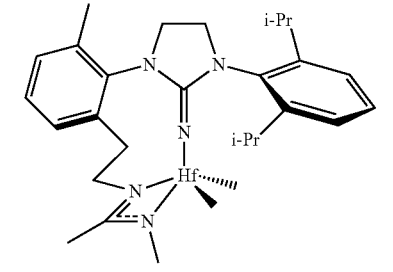
128
-continued
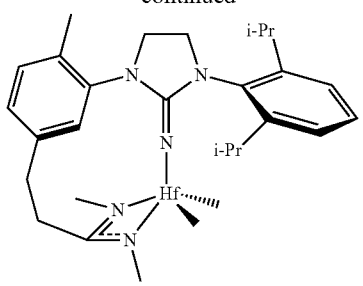
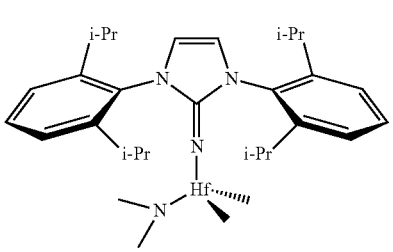
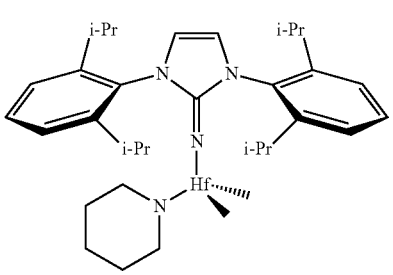
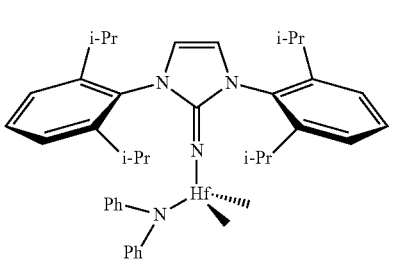
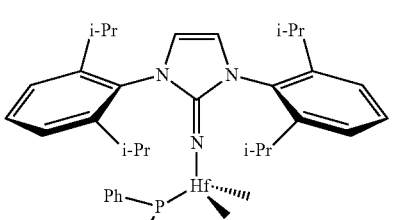
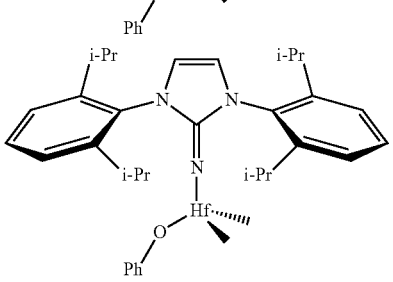

129
-continued
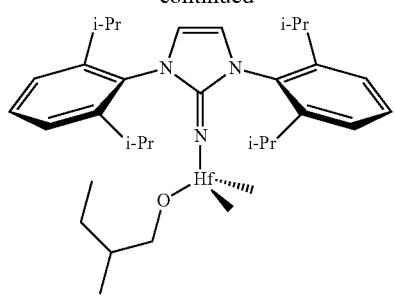
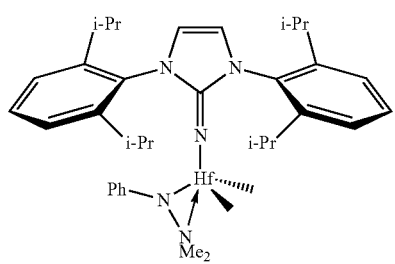
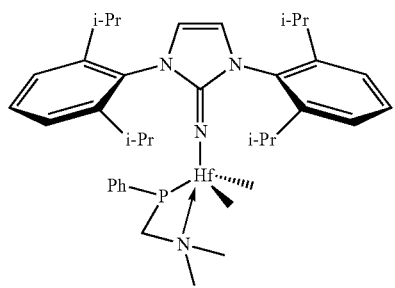
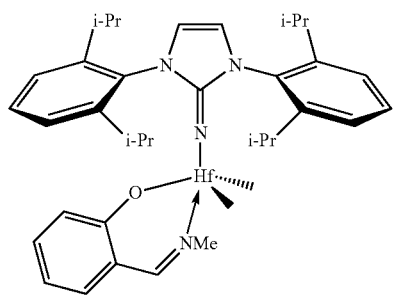
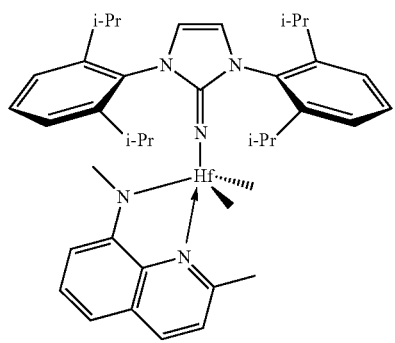
130
-continued
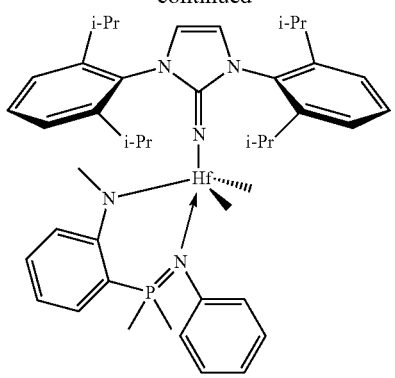
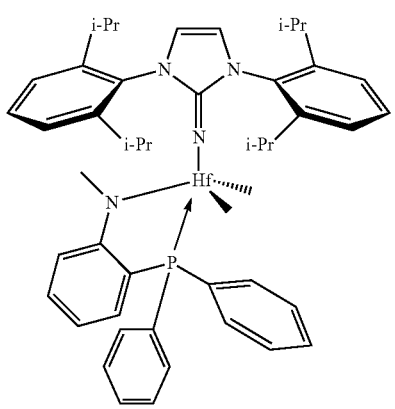
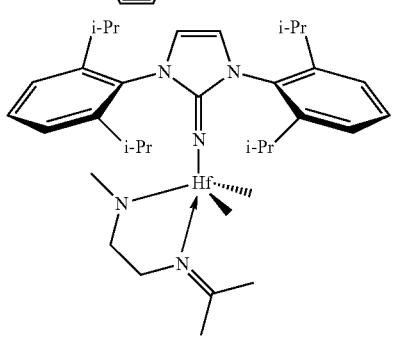
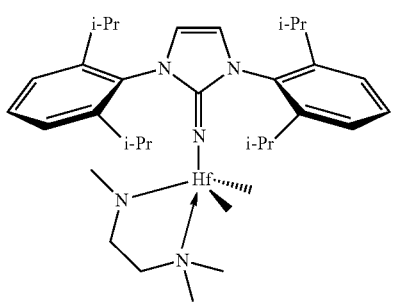
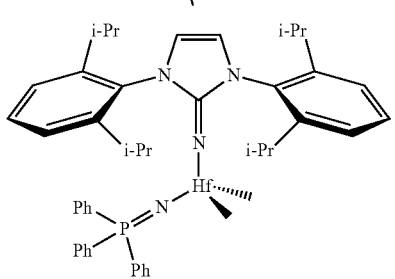

131
-continued
132
-continued
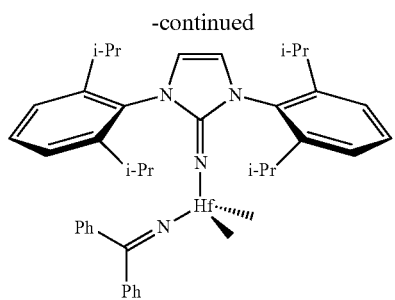
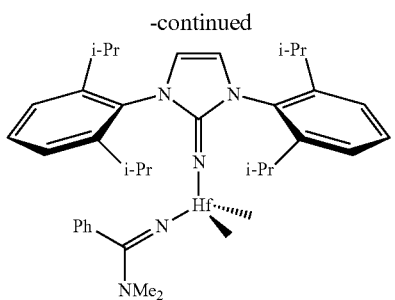

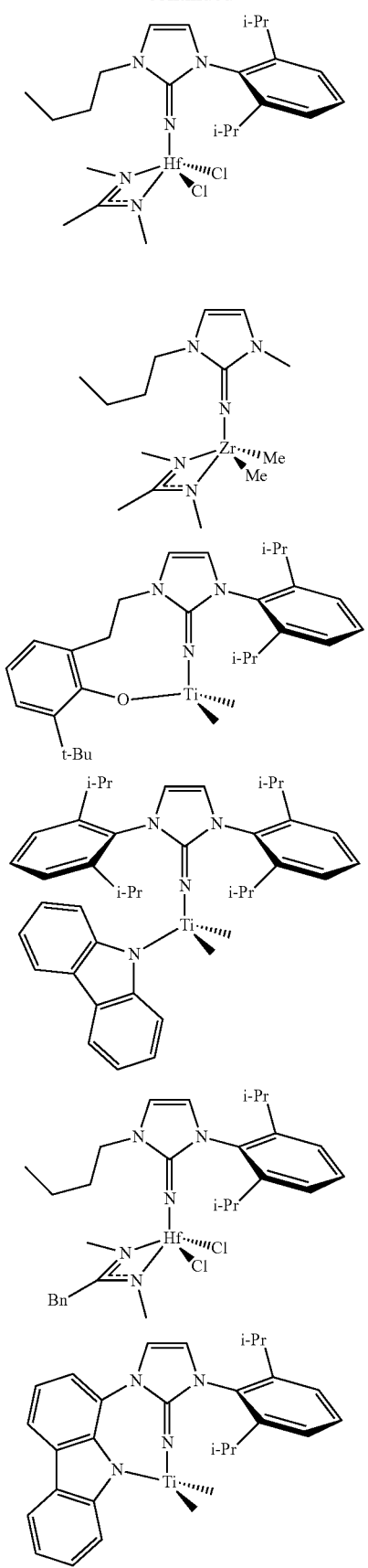
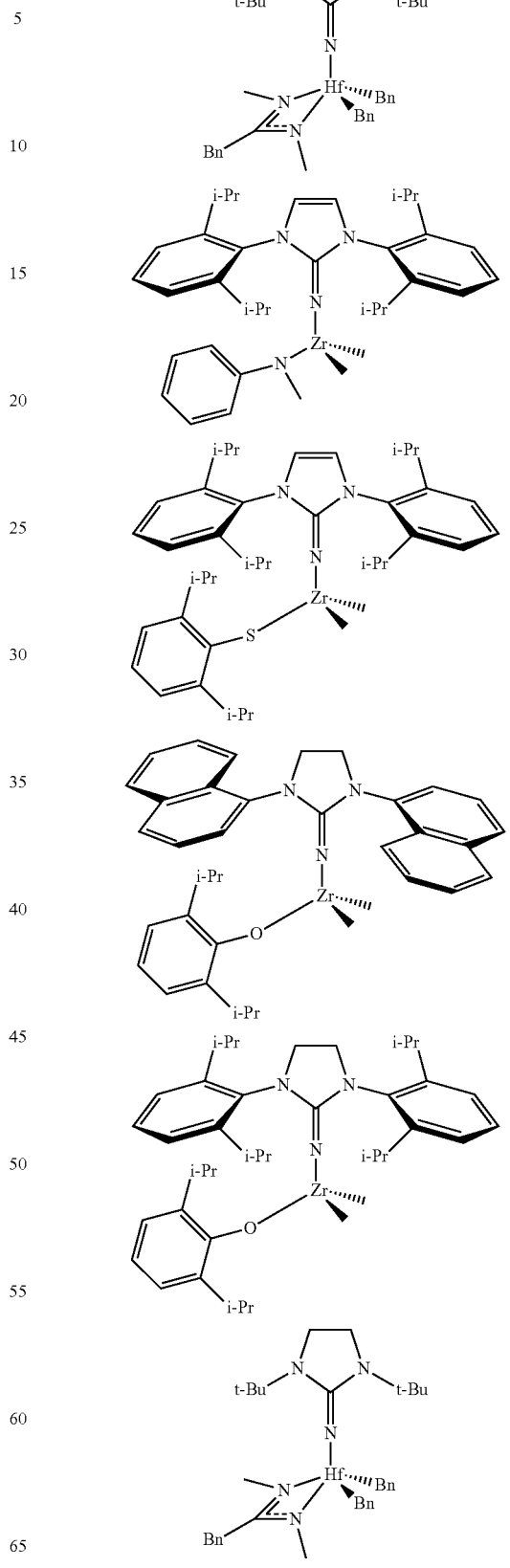

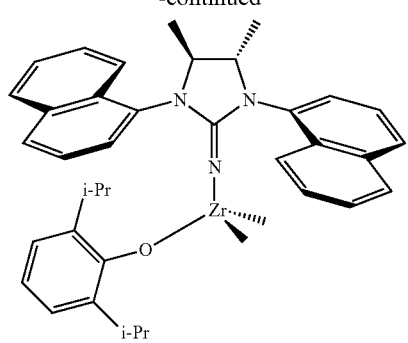

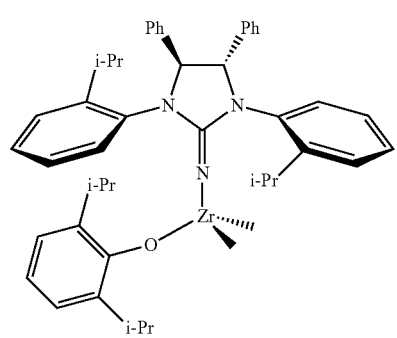

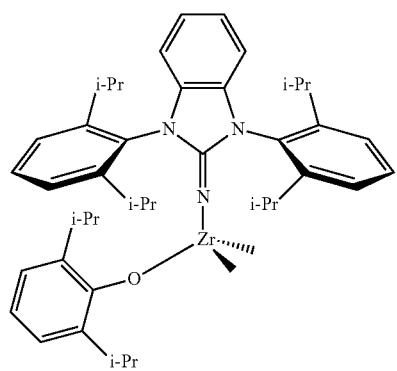

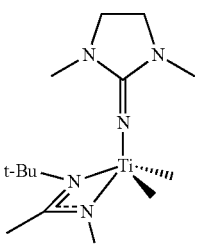

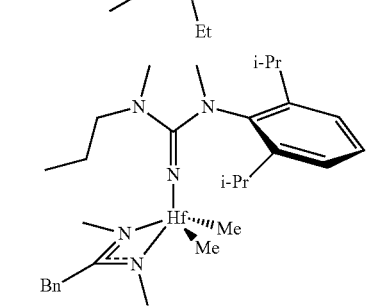

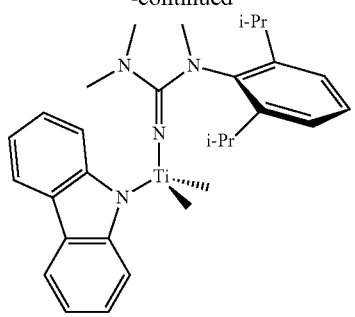

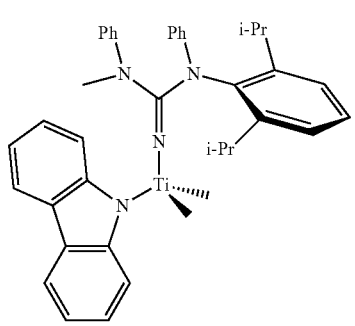

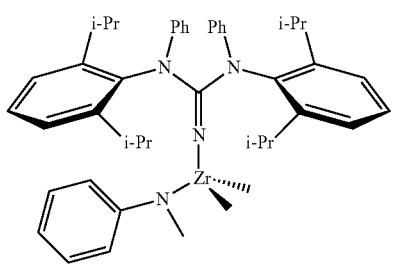

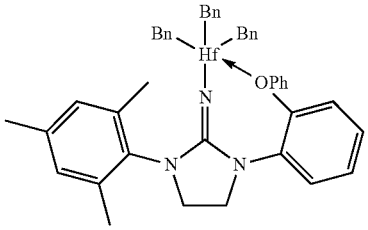

or a combination thereof.

13. A catalyst comprising, or comprising the reaction product of, one or more metal-ligand complexes of claim 1, and one or more activating cocatalysts, wherein a ratio of total number of moles of the one or more metal-ligand complexes to total number of moles of the one or more activating cocatalyst is 1:10,000 to 100:1.

14. A process for preparing a polyolefin, the process comprising contacting at least one polymerizable olefin with the catalyst of claim 13 under conditions sufficient to polymerize at least some of the at least one polymerizable olefin, thereby producing a polyolefin.

15. The process of claim 14, wherein the at least one polymerizable olefin comprises ethylene and octene.

16. A metal-ligand complex having formula (V)

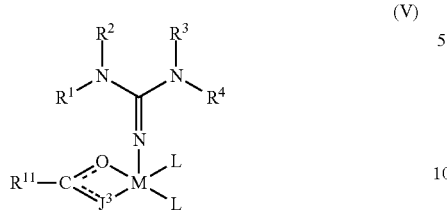

(V)

wherein
- L is independently at each occurance halogen, hydrogen, $((C_1\text{-}C_{40})\text{hydrocarbyl})C(O)N(H)—$, $((C_1\text{-}C_{40})\text{hydrocarbyl})C(O)N(H)(C_1\text{-}C_{20})\text{hydrcarbyl-}$, $((C_1\text{-}C_{40})\text{hydrocarbyl})C(O)O—$, $((C_1\text{-}C_{40})\text{hydrocarbyl-}$, or $(C_1\text{-}C_{40})\text{heterohydrocarbyl-}$; and each occurrence of L is a monoanionic moeity that is bonded to M;
- M is a metal of any one of Groups 3, 4, 5, and 6 of a Periodic Table of the Elements, the metal being in a formal oxidation state of +2, +3, +4, +5, +6;
- $R^1$, $R^2$, $R^3$, and $R^4$ are independently at each occurrence hydrogen, $(C_1\text{-}C_{40})\text{hydrocarbyl-}$, $((C_1\text{-}C_{40})\text{hydrocarbly})O—$, $((C_1\text{-}C_{40})\text{hydrocarbyl})S—$, $((C_1\text{-}C_{40})\text{hydrocarbyl})_3Si—$, or $(C_1\text{-}C_{40})\text{heterohydrocarbyl-}$;
- $J^3$ is O or $NR^{12}$;
- $R^{11}$ and $R^{12}$ are each independently hydrogen, $(C_1\text{-}C_{40})$ hydrocarbyl-, $((C_1\text{-}C_{40})\text{hydrocarbyl})O—$, $((C_1\text{-}C_{40})\text{hydrocarbyl})S—$, $((C_1\text{-}C_{40})\text{hydrocarbyl})_3Si—$, or $(C_1\text{-}C_{40})\text{heterohydrocarbyl-}$;
- $R^{11}$ and $R^{12}$ are optionally taken together to form $(C_2\text{-}C_{40})\text{hydrocarbylene}$ or $(C_1\text{-}C_{40})\text{heterohydrocarbylene}$;
- one of $R^{11}$ and $R^{12}$ is optionally taken together with one of $R^1$, $R^2$, $R^3$, $R^4$, or L to form a $(C_2\text{-}C_{40})\text{hydrocarbylene}$ or $(C_1\text{-}C_{40})\text{heterohydrocarbylene}$;
- two occurrences of L are optionally taken together to form a $(C_2\text{-}C_{40})\text{hydrocarbylene}$ or $(C_1\text{-}C_{40})\text{heterohydrocarbylene}$, or $(R^D)_2C=C(R^D)—C(R^D)=C(R^D)_2$, wherein each $R^D$ independently is H, unsubstituted $(C_1\text{-}C_6)$ alkyl, phenyl, or naphthyl;
- one occurrence of L and one of $R^1$, $R^2$, $R^3$, or $R^4$ are optionally taken together to form $(C_2\text{-}C_{40})\text{hydrocarbylene}$ or $(C_1\text{-}C_{40})\text{heterohydrocarbylene}$; and
- any two of $R^1$, $R^2$, $R^3$, or $R^4$ are optionally taken together to form a $(C_2\text{-}C_{40})\text{hydrocarbylene}$ or $(C_1\text{-}C_{40})\text{heterohydrocarbylene}$.

17. The metal-ligand complex of claim 16, selected from the group consisting of

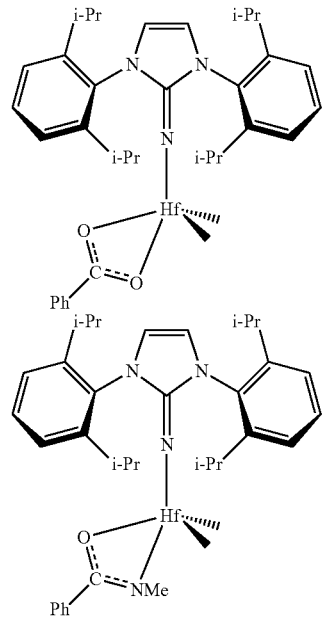

and combinations thereof.

* * * * *